(12) United States Patent
Hyde et al.

(10) Patent No.: US 8,876,688 B2
(45) Date of Patent: Nov. 4, 2014

(54) COMBINATION TREATMENT MODIFICATION METHODS AND SYSTEMS

(75) Inventors: Roderick A. Hyde, Redmond, WA (US); Muriel Y. Ishikawa, Livermore, CA (US); Eric C. Leuthhardt, St. Louis, MO (US); Royce A. Levien, Lexington, MA (US); Robert W. Lord, Seattle, WA (US); Mark A. Malamud, Seattle, WA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 1069 days.

(21) Appl. No.: 12/157,160

(22) Filed: Jun. 6, 2008

(65) Prior Publication Data

US 2009/0271008 A1    Oct. 29, 2009

Related U.S. Application Data

(63) Continuation-in-part of application No. 12/150,122, filed on Apr. 24, 2008, and a continuation-in-part of application No. 12/152,266, filed on May 13, 2008, now abandoned, and a continuation-in-part of application No. 12/154,275, filed on May 21, 2008, now Pat. No. 7,974,787, and a continuation-in-part of application No. 12/156,440, filed on May 30, 2008, and a continuation-in-part of application No. 12/156,949, filed on Jun. 5, 2008.

(51) Int. Cl.
*G05B 13/00* (2006.01)
*G06F 19/00* (2011.01)

(52) U.S. Cl.
CPC ............ *G06F 19/324* (2013.01); *G06F 19/363* (2013.01)
USPC .................... 600/21; 128/897; 705/2; 700/28

(58) Field of Classification Search
USPC .................................. 600/21; 128/897; 705/2
See application file for complete search history.

(56) References Cited

U.S. PATENT DOCUMENTS

| | | |
|---|---|---|
| 3,036,568 A | 5/1962 | Stark |
| 4,570,640 A | 2/1986 | Barsa |
| 4,734,585 A | 3/1988 | Owers |

(Continued)

FOREIGN PATENT DOCUMENTS

| | | |
|---|---|---|
| WO | WO 03/048789 A2 | 6/2003 |
| WO | WO 2006/048417 A1 | 5/2006 |
| WO | WO2007/016241 | 2/2007 |
| WO | WO 2007/141373 A2 | 12/2007 |

OTHER PUBLICATIONS

Webpage of Merriam-Webster's online dictionary—Definition of Alter.*

(Continued)

*Primary Examiner* — Christine Matthews
*Assistant Examiner* — Joshua D Lannu

(57) ABSTRACT

Methods, computer program products, and systems are described that include accepting at least one indication of bioactive agent use by an individual and/or modifying an artificial sensory experience to alter at least one effect of the bioactive agent.

34 Claims, 43 Drawing Sheets

(56) References Cited

U.S. PATENT DOCUMENTS

| | | | |
|---|---|---|---|
| 4,755,043 A | 7/1988 | Carter | |
| 4,962,491 A | 10/1990 | Schaeffer | |
| 4,973,149 A | 11/1990 | Hutchinson | |
| 4,974,729 A | 12/1990 | Steinnagel | |
| 5,099,463 A | 3/1992 | Lloyd et al. | |
| 5,135,752 A | 8/1992 | Snipes | |
| 5,200,891 A | 4/1993 | Kehr et al. | |
| 5,277,188 A | 1/1994 | Selker | |
| 5,348,268 A | 9/1994 | Klein | |
| 5,408,443 A | 4/1995 | Weinberger | |
| 5,463,564 A | 10/1995 | Agrafiotis et al. | |
| 5,508,042 A | 4/1996 | Oshlack et al. | |
| 5,577,981 A | 11/1996 | Jarvik | |
| 5,610,674 A | 3/1997 | Martin | |
| 5,645,072 A | 7/1997 | Thrall et al. | |
| 5,671,752 A | 9/1997 | Sinderby et al. | |
| 5,722,754 A | 3/1998 | Langner | |
| 5,724,983 A | 3/1998 | Selker et al. | |
| 5,725,472 A | 3/1998 | Weathers | |
| 5,822,726 A | 10/1998 | Taylor et al. | |
| 5,845,255 A | 12/1998 | Mayaud | |
| 5,846,086 A | 12/1998 | Bizzi et al. | |
| 5,891,049 A | 4/1999 | Cyrus et al. | |
| 5,919,141 A | 7/1999 | Money et al. | |
| 6,053,866 A | 4/2000 | McLeod | |
| 6,067,523 A | 5/2000 | Bair et al. | |
| 6,102,846 A | 8/2000 | Patton et al. | |
| 6,149,586 A | 11/2000 | Elkind | |
| 6,152,563 A | 11/2000 | Hutchinson et al. | |
| 6,168,562 B1 | 1/2001 | Miller et al. | |
| 6,186,145 B1 | 2/2001 | Brown | |
| 6,198,953 B1 | 3/2001 | Webster et al. | |
| 6,282,458 B1 | 8/2001 | Murayama et al. | |
| 6,314,384 B1 | 11/2001 | Goetz | |
| 6,315,719 B1 | 11/2001 | Rode et al. | |
| 6,334,778 B1 | 1/2002 | Brown | |
| 6,368,111 B2 | 4/2002 | Legarda | |
| 6,383,135 B1 | 5/2002 | Chikovani et al. | |
| 6,390,453 B1 | 5/2002 | Frederickson et al. | |
| 6,397,080 B1 | 5/2002 | Viktorsson et al. | |
| 6,421,650 B1 | 7/2002 | Goetz et al. | |
| 6,425,764 B1 | 7/2002 | Lamson | |
| 6,448,030 B1 | 9/2002 | Rust et al. | |
| 6,487,520 B1 | 11/2002 | Kurtzberg et al. | |
| 6,542,858 B1 | 4/2003 | Grass et al. | |
| 6,561,811 B2 | 5/2003 | Rapoza et al. | |
| 6,565,359 B2 | 5/2003 | Calhoun et al. | |
| 6,631,291 B2 | 10/2003 | Viertiö-Oja et al. | |
| 6,647,358 B2 | 11/2003 | Grass et al. | |
| 6,702,767 B1 * | 3/2004 | Douglas et al. | 601/15 |
| 6,723,527 B2 | 4/2004 | Pettit et al. | |
| 6,807,492 B2 | 10/2004 | Oren et al. | |
| 6,826,498 B2 | 11/2004 | Birkner et al. | |
| 6,832,178 B1 | 12/2004 | Fernandez et al. | |
| 6,852,069 B2 | 2/2005 | Park | |
| 6,886,653 B1 | 5/2005 | Bellehumeur | |
| 6,909,359 B1 | 6/2005 | McGovern | |
| 6,947,790 B2 | 9/2005 | Gevins et al. | |
| 6,952,695 B1 | 10/2005 | Trinks et al. | |
| 6,968,375 B1 | 11/2005 | Brown | |
| 6,997,880 B2 | 2/2006 | Carlebach et al. | |
| 7,002,476 B2 | 2/2006 | Rapchak | |
| 7,033,025 B2 | 4/2006 | Winterbotham | |
| 7,039,878 B2 | 5/2006 | Auer et al. | |
| 7,044,911 B2 | 5/2006 | Drinan et al. | |
| 7,049,103 B2 | 5/2006 | Ishiguro et al. | |
| 7,076,437 B1 | 7/2006 | Levy | |
| 7,084,874 B2 | 8/2006 | Kurzweil | |
| 7,144,680 B2 | 12/2006 | Park et al. | |
| 7,148,208 B2 | 12/2006 | Barkan et al. | |
| 7,161,579 B2 | 1/2007 | Daniel | |
| 7,177,675 B2 | 2/2007 | Suffin et al. | |
| 7,197,492 B2 | 3/2007 | Sullivan | |
| 7,198,044 B2 | 4/2007 | Trueba | |
| 7,226,164 B2 | 6/2007 | Abourizk et al. | |
| 7,229,288 B2 | 6/2007 | Stuart et al. | |
| 7,245,956 B2 | 7/2007 | Matthews et al. | |
| 7,272,431 B2 | 9/2007 | McGrath | |
| 7,294,107 B2 | 11/2007 | Simon et al. | |
| 7,353,065 B2 | 4/2008 | Morrell | |
| 7,461,651 B2 | 12/2008 | Brown | |
| 7,513,622 B2 | 4/2009 | Khaderi | |
| 7,575,865 B2 | 8/2009 | Leamon et al. | |
| 7,623,927 B2 | 11/2009 | Rezai | |
| 7,890,340 B2 | 2/2011 | Abraham-Fuchs et al. | |
| 8,150,629 B2 | 4/2012 | Geerts et al. | |
| 2001/0001144 A1 | 5/2001 | Kapp | |
| 2001/0010541 A1 | 8/2001 | Fernandez et al. | |
| 2002/0091546 A1 | 7/2002 | Christakis et al. | |
| 2002/0103428 A1 | 8/2002 | deCharms | |
| 2002/0103429 A1 | 8/2002 | deCharms | |
| 2002/0128061 A1 | 9/2002 | Blanco | |
| 2003/0036683 A1 | 2/2003 | Kehr et al. | |
| 2003/0144884 A1 | 7/2003 | Mayaud | |
| 2003/0214630 A1 | 11/2003 | Winterbotham | |
| 2003/0225362 A1 | 12/2003 | Currie et al. | |
| 2004/0024287 A1 | 2/2004 | Patton et al. | |
| 2004/0024616 A1 | 2/2004 | Spector et al. | |
| 2004/0078027 A1 | 4/2004 | Shachar | |
| 2004/0078239 A1 | 4/2004 | Dacosta | |
| 2004/0092809 A1 | 5/2004 | DeCharms | |
| 2004/0123667 A1 | 7/2004 | McGrath | |
| 2004/0127778 A1 | 7/2004 | Lambert et al. | |
| 2004/0172285 A1 | 9/2004 | Gibson | |
| 2004/0196184 A1 | 10/2004 | Hollander et al. | |
| 2005/0021372 A1 | 1/2005 | Mikkelsen et al. | |
| 2005/0054942 A1 | 3/2005 | Melker et al. | |
| 2005/0065813 A1 | 3/2005 | Mishelevich et al. | |
| 2005/0086077 A1 | 4/2005 | Forman | |
| 2005/0124851 A1 | 6/2005 | Patton et al. | |
| 2005/0124878 A1 | 6/2005 | Sharony | |
| 2005/0165115 A1 | 7/2005 | Murphy et al. | |
| 2005/0197654 A1 | 9/2005 | Edman et al. | |
| 2005/0240084 A1 | 10/2005 | Morice et al. | |
| 2005/0277911 A1 | 12/2005 | Stewart et al. | |
| 2006/0031099 A1 | 2/2006 | Vitello et al. | |
| 2006/0058694 A1 | 3/2006 | Clark et al. | |
| 2006/0059145 A1 | 3/2006 | Henschke et al. | |
| 2006/0062852 A1 | 3/2006 | Holmes | |
| 2006/0084877 A1 | 4/2006 | Ujhazy et al. | |
| 2006/0111644 A1 | 5/2006 | Guttag et al. | |
| 2006/0161408 A1 | 7/2006 | Bachman et al. | |
| 2006/0161456 A1 | 7/2006 | Baker et al. | |
| 2006/0183980 A1 | 8/2006 | Yang | |
| 2006/0235724 A1 | 10/2006 | Rosenthal | |
| 2006/0241718 A1 | 10/2006 | Tyler et al. | |
| 2006/0247489 A1 | 11/2006 | Carbis et al. | |
| 2006/0252761 A1 | 11/2006 | Davis et al. | |
| 2006/0265253 A1 | 11/2006 | Rao et al. | |
| 2007/0016265 A1 | 1/2007 | Davoodi et al. | |
| 2007/0067186 A1 | 3/2007 | Brenner et al. | |
| 2007/0072821 A1 | 3/2007 | Iakoubova et al. | |
| 2007/0088404 A1 | 4/2007 | Wyler et al. | |
| 2007/0112277 A1 | 5/2007 | Fischer et al. | |
| 2007/0112624 A1 | 5/2007 | Jung et al. | |
| 2007/0123783 A1 | 5/2007 | Chang | |
| 2007/0136093 A1 | 6/2007 | Rankin et al. | |
| 2007/0167853 A1 | 7/2007 | Melker et al. | |
| 2007/0172814 A1 | 7/2007 | Li | |
| 2007/0179534 A1 * | 8/2007 | Firlik et al. | 607/3 |
| 2007/0191704 A1 | 8/2007 | DeCharms | |
| 2008/0045832 A1 | 2/2008 | McGrath | |
| 2008/0046286 A1 | 2/2008 | Halsted | |
| 2008/0097167 A1 | 4/2008 | Yudkovitch et al. | |
| 2008/0125978 A1 | 5/2008 | Robson et al. | |
| 2008/0132383 A1 | 6/2008 | Einav et al. | |
| 2008/0139870 A1 | 6/2008 | Gliner et al. | |
| 2008/0139902 A1 | 6/2008 | Kotulla et al. | |
| 2008/0167571 A1 | 7/2008 | Gevins | |
| 2008/0172044 A1 | 7/2008 | Shelton | |
| 2008/0177197 A1 | 7/2008 | Lee et al. | |
| 2008/0212847 A1 | 9/2008 | Davies et al. | |
| 2008/0221847 A1 | 9/2008 | Fenetteau | |
| 2008/0226730 A1 | 9/2008 | Schmitke et al. | |

(56) References Cited

U.S. PATENT DOCUMENTS

| | | |
|---|---|---|
| 2008/0242947 A1 | 10/2008 | Jung et al. |
| 2008/0243544 A1 | 10/2008 | Cafer |
| 2008/0267447 A1 | 10/2008 | Kelusky et al. |
| 2008/0275731 A1 | 11/2008 | Rao et al. |
| 2008/0278682 A1 | 11/2008 | Huxlin et al. |
| 2008/0305518 A1 | 12/2008 | Klausen et al. |
| 2009/0171697 A1 | 7/2009 | Glauser et al. |
| 2009/0306741 A1 | 12/2009 | Hogle et al. |
| 2009/0312817 A1 | 12/2009 | Hogle et al. |
| 2010/0015184 A1 | 1/2010 | Tuel |
| 2010/0094202 A1 | 4/2010 | Edginton et al. |
| 2010/0163027 A1 | 7/2010 | Hyde et al. |
| 2010/0168525 A1 | 7/2010 | Hyde et al. |
| 2010/0168602 A1 | 7/2010 | Hyde et al. |
| 2010/0324874 A9 | 12/2010 | Bangs et al. |

OTHER PUBLICATIONS

Barrientos, Ruth M. et al.; "Memory for context is impaired by injecting anisomycin into dorsal hippocampus following context exploration"; Behavioural Brain Research; bearing a date of Aug. 21, 2002; pp. 299-306; vol. 134, Issues 1-2; Elsevier Science B.V. (abstract only).

Grollman, Arthur P ; "Inhibitors of Protein Biosynthesis"; The Journal of Biological Chemistry; bearing a date of Jul. 10, 1967; pp. 3266-3233; vol. 242, No. 13.

Hunter G. Hoffman, et al., Analgesic Effects of Opioids and Immersive Virtual Reality Distraction: Evidence from Subjective and Functional Brain Image Assessments, Anesthesia & Analgesia, 2007, pp. 1776-1783, vol. 105, Published in: US.

D. Shaw, et al., Anxiolytic Effects of Lavender Oil Inhalation on Open-Field Behaviour in Rats, Phytomedicine, Mar. 19, 2007, pp. 613-620, vol. 14.

Barbara Ortutay, Brain-Reading Headset to Sell for $299, Feb. 20, 2008, Publisher: Associated Press, Published in: US.

Sandra L. Siedliecki, et al., Efect of Music on Power, Pain, Depression, and Disability, Journal of Advanced Nursing, Jan. 13, 2006, pp. 553-562, vol. 54, Publisher: Blackwell Publishing, Published in: US.

Maura Paul-Labrador, et al., Effects of a Randomized Controlled Trail of Transcendental Meditation on Components of the Metabolic Syndrome in Subjects With Coronary Heart Disease, Arch Intern Med, Jun. 12, 2006, pp. 1218-1224, vol. 166, Publisher: American Medical Society, Published in: US.

Igor Knez, Effects of Colour of Light on Nonvisual Psychological Processes, Jun. 2001, pp. 201-208, vol. 21, No. 2, Publisher: Journal of Environmental Psychology, Published in: US.

E. Glenn Schellenberg, et al., Exposure to Music and Cognitive Performance: Tests of Children and Adults, Psychology of Music, 2007, pp. 5-19, vol. 35, Published in: Canada.

Russell N. Carney, et al., Mnemonic Instruction, With a Focus on Transfer, Dec. 2000, pp. 783-790, vol. 92, Publisher: Journal of Educational Psychology, Published in: US.

M.R. Basso, Jr., Neurobiological Relationships Between Ambient Lighting and the Startle Response to Acoustic Stress in Humans, Sep. 2001, pp. 147-157, vol. 110, No. 3-4, Publisher: International Journal of Neuroscience, Published in: US.

Neda Gould, et al., Performance on a Virtual Reality Spatial Memory Navigation Task in Depressed Patients, American Journal of Psychiatry, Mar. 10, 2007, pp. 516-519, vol. 165, Published in: US.

Something in the Way He Moves, The Economist, Sep. 27, 2007, Publisher: http://www.economist.com/science/PrinterFriendly.cfm?story_id=9861412, Published in: US.

Raymond W. Lam, et al., The Can-SAD Study: A Randomized Controlled Trial of the Effectiveness of Light Therapy and Fluoxetine in Patients With, May 2006, pp. 805-812, vol. 163, Publisher: American Journal of Psychiatry, Published in: US.

Elizabeth Von Muggenthaler, The Felid Purr: A Bio-Mechanical Healing Mechanism, Sep. 18, 2006, Publisher: 12th International Conference on Low Frequency Noise and Vibration and its Control, Published in: Bristol, UK.

Shelley Wiechman Askay, Using Hypnosis for Spinal Cord Injury Pain Management, SCI Forum Report, Sep. 11, 2007, Publisher: http://sci.washington.edu/info/forums/reports/hypnosis_for_sci_pain.asp, Published in: US.

Matthew M. Kurtz, et al., A Virtual Reality Apartment as a Measure of Medication Management Skills in Patients with Schizophrenia: A Pilot Study, Schizophrenia Bulletin, 2007, pp. 1162-1170, vol. 33, No. 5, Publisher: Oxford University Press, Published in: US.

Virtual Reality Medical Center, Publisher: http://www.vrphobia.com/, Published in: US, printed on Mar. 4, 2008.

Virtual Reality Pain Reduction, Human Interface Technology Lab (HITL), Apr. 18, 2008, pp. 1-3, Publisher: http://hitl.washington.edu/projects/vrpain/, Published in: US.

Hunter G. Hoffman, Virtual-Reality Therapy, Scientific American, Jul. 26, 2004, pp. 60-65, Published in: US.

Alessandra Gorini, et al., Virtual Worlds, Real Healing, Science, Dec. 7, 2007, p. 1549, vol. 318, No. 5856, Publisher: AAAS, Published in: US.

J.A. Spencer, et al., White Noise and Sleep Induction, Archives of Disease in Childhood, 1990, p. 135-137, vol. 65, Publisher: BMJ Publishing Group, Published in: London.

U.S. Appl. No. 12/315,366, Hyde et al.
U.S. Appl. No. 12/315,072, Hyde et al.
U.S. Appl. No. 12/290,456, Hyde et al.
U.S. Appl. No. 12/290,227, Hyde et al.
U.S. Appl. No. 12/287,886, Hyde et al.
U.S. Appl. No. 12/287,686, Hyde et al.
U.S. Appl. No. 12/286,751, Hyde et al.
U.S. Appl. No. 12/286,730, Hyde et al.
U.S. Appl. No. 12/283,742, Hyde et al.
U.S. Appl. No. 12/283,619, Hyde et al.
U.S. Appl. No. 12/229,612, Hyde et al.
U.S. Appl. No. 12/229,531, Hyde et al.
U.S. Appl. No. 12/220,706, Hyde et al.
U.S. Appl. No. 12/218,627, Hyde et al.

Axelrod, Lesley et al.; "Smoke and mirrors: gathering user requirements for emerging affective systems"; bearing a date of Jun. 7-10, 2004; pp. 323-328; vol. 1; 26th International Conference on Information Technology Interfaces, 2004.

Bayard, Max, M.D. et al.; "Alcohol Withdrawal Syndrome"; American Family Physician; bearing a date of Mar. 15, 2004; pp. 1443-1450; vol. 69, No. 6.

Bosworth, Kris et al.; "A Computer-Based Violence Prevention Intervention for Young Adolescents: A Pilot Study"; Adolescence; bearing a date Winter 1998; pp. 785-796; vol. 33 No. 132; Libra Publishers, Inc. [Abstract Only].

U.S. Appl. No. 12/218,503, Hyde et al.
U.S. Appl. No. 12/217,620, Hyde et al.
U.S. Appl. No. 12/217,509, Hyde et al.
U.S. Appl. No. 12/214,547, Hyde et al.
U.S. Appl. No. 12/157,989, Hyde et al.
U.S. Appl. No. 12/157,922, Hyde et al.

Canadas-Quesada, F. J. et al.; "Improvement of Perceived Stiffness Using Auditory Stimuli in Haptic Virtual Realty"; IEEE Melecon; bearing a date of May 16-19, 2006; published in Benalmadena, Spain.

Clarke, Peter; IMEC Has a Brain Wave: Feed EEG Emotion Back Into Games; EE Times online; bearing a date of Nov. 1, 2007; pp. 1-2; located at http://www.eetimes.eu/design/202801063.

Cohn, J. N.; "Introduction to Surrogate Markers"; Circulation; bearing a date of 2004; pp. 1-3; vol. 109; American Heart Association; located at http://circ.ahajournals.org/cgi/content/full/109/25_suppl_IV-20.

Faris, Robert E.L.; "Cultural Isolation and the Schizophrenic Personality"; The American Journal of Sociology; bearing a date of Sep. 1934; pp. 155-164; vol. 40, No. 2; University of Chicago Press; located at http://www.jstor.org/pss/2768057; [Abstract Only].

Green, T. et al.; "PC-Based Medical Data Acquisition and Analysis"; bearing a date of 1995; p. 159; 8th IEEE Symposium on Computer-Based Medical Systems (CBMS) '95 [Abstract Only].

Greenland, Sander et al.; Methods for Trend Estimation from Summarized Dose-Response Data, with Applications to Meta-Analysis; American Journal of Epidemiology; bearing a date of 1992; pp.

(56) References Cited

OTHER PUBLICATIONS 1301-1309; vol. 135, No. 11; located at http://aje.oxfordjournals.org/cgi/content/abstract/135/11/1301 [Abstract Only].

Grossman, E. et al.; "Breathing-Control Lowers Blood Pressure"; Journal of Human Hypertension; bearing a date of Apr. 2001; pp. 263-269; vol. 15, No. 4; Nature Publishing Group.

Harland, C.J. et al.; "Electric potential probes—new directions in the remote sensing of the human body"; Measurement Science and Technology; bearing a date of 2002; pp. 163-169; vol. 13; Institute of Physics Publishing.

Harland, C.J. et al.; "High Resolution Ambulatory Electrocardiographic Monitoring Using Wrist-Mounted Electric Potential Sensors"; Measuring Science and Technology; bearing a date of May 23, 2003; pp. 923-928; vol. 14; IOP Publishing Ltd.

Harland, C.J. et al.; "Remote Detection of Human Electroencephalograms Using Ultrahigh Input Impedance Electric Potential Sensors"; Applied Physics Letters; bearing a date of Oct. 21, 2002; pp. 3284-3286; vol. 81, No. 17; American Institute of Physics.

Huo, Xueliang et al.; "A Wireless Pharmaceutical Compliance Monitoring System Based on Magneto-Inductive Sensors"; Sensors Journal; IEEE; bearing a date of Dec. 2007; pp. 1711-1719; vol. 7, No. 12 [Abstract Only].

Jeanpierre, Laurent et al.; Automated Medical Diagnosis with Fuzzy Stochastic Models: Monitoring Chronic Diseases; Acta Biotheoretica; bearing a date of 2004; pp. 291-311; vol. 52, No. 4; Springer Publishing [Abstract Only].

Jokiniitty, J.M. et al.; "Prediction of Blood Pressure Level and Need for Antihypertensive Medication: 10 Years of Follow-up"; Journal of Hypertension; bearing a date of Jul. 2001; pp. 1193-1201; vol. 19, No. 7 [Abstract Only].

Kozarek, R.A. et al.; "Prospective Trial Using Virtual Vision as Distraction Technique in Patients Undergoing Gastric Laboratory Procedures"; Gastroenterology Nursing; bearing a date of Jan. 1997; vol. 20, No. 1 [Abstract Only].

Lawrence, Dale A. et al.; "Human Perception of Friction in Haptic Interfaces"; Proc. Symposium on Haptic Interfaces for Virtual Environment and Teleoperator Systems; ASME Int'l Mech. Eng. Congress and Expo, Dynamic Systems and Control Division; bearing a date of Nov. 1998; pp. 287-294; vol. 64.

Marlier, Luc et al.; "Olfactory Stimulation Prevents Apnea in Premature Newborns"; Pediatrics; bearing a date of 2005; pp. 83-88; vol. 115, No. 1; American Academy of Pediatrics.

Matthews, D.E. et al.; "Using and Understanding Medical Statistics"; bearing a date of 2007; pp. 111-127; S. Karger AG Basel.

McClernon, F. Joseph et al.; "The Effects of Controlled Deep Breathing on Smoking Withdrawal Symptoms in Dependent Smokers"; ScienceDirect; bearing a date of Jun. 2004; pp. 765-772; vol. 29, No. 4; Elsevier Ltd. [Abstract Only].

Ming, Jin-Lain et al.; "The Efficacy of Acupressure to Prevent Nausea and Vomiting in Post-Operative Patients"; Journal of Advanced Nursing; bearing a date of Aug. 2002; pp. 343-351; vol. 39, No. 4; Blackwell Synergy [Abstract Only].

Morishita, S. et al.; "Induction of Mania in Depression by Paroxetine"; Human Psychopharmacol; bearing a date of Oct. 2003; pp. 565-568; vol. 18, No. 7; Dept. of Psychiatry, Kawasaki Medical School [Abstract Only].

"New Horizons of Nerve Repair: Biomedical Engineer Trips Up Proteins in Nerve Regeneration System"; Science Daily; bearing a date of Jul. 26, 2002; pp. 1-2; located at http://www.sciencedaily.com/releases/2002/07/020725082253.htm.

"New Mini-Sensor May Have Biomedical and Security Applications"; Physics/General Physics; bearing a date of Nov. 1, 2007; pp. 1-3; located at http://www.physorg.com/news113151078.html; Physorg.com.

Parker, G. et al.; "Prediction of Response to Antidepressant Medication by a Sign-Based Index of Melancholia"; Australian and New Zealand Journal of Psychiatry; bearing a date of 1993; pp. 56-61; vol. 27, No. 1 [Abstract Only].

Patolsky, Fernando et al.; "Nanowire Sensors for Medicine and the Life Sciences"; Future Medicine; bearing a date of Jun. 2006; pp. 51-65; vol. 1, No. 1 [Abstract Only].

"Phosphodiesterase Isoenzymes as Pharmacological Targets in the Treatment of Male Erectile Dysfunction"; World Journal of Urology; bearing a date of Feb. 2001; pp. 14-22; vol. 19, No. 1; Springer Berlin/Heidelberg [Abstract Only].

Piquepaille, Roland; "Virtual Reality Helps Diagnose Heart Defects"; bearing a date of Dec. 28, 2005; 2008 CNET Networks, Inc.

Prance, R.J. et al.; "Adaptive Electric Potential Sensors for Smart Signal Acquisition and Processing"; Journal of Physics: Conference Series 76; Sensors and their Applications XIV (SENSORS07); bearing a date of 2007; pp. 1-5; IOP Publishing Ltd.

Rizzo, Albert et al.; "Virtual Therapeutic Environments with Haptics: An Interdisciplinary Approach for Developing Post-Stroke Rehabilitation Systems"; CPSN 2005; bearing a date of Jun. 20-23, 2005; pp. 70-76; Proceedings of the 2005 International Conference on Computers for People with Special Needs; University of Southern California.

Sanfey, Alan G.; "Social Decision-Making: Insights from Game Theory and Neuroscience"; Science Magazine; bearing a date of Oct. 26, 2007; pp. 598-602; vol. 318, No. 5850.

Skorin, Leonid Jr., et al.; "How to Diagnose and Manage Headaches"; Review of Optometry; bearing a date of Nov. 1999; pp. 73-76; vol. 136.

Smith, M.R. et al.; "A data extrapolation algorithm using a complex domain neuralnetwork"; Circuits and Systems II: Analog and Digital Signal Processing; IEEE Transactions; bearing a date of Feb. 1997; pp. 143-147; vol. 44, No. 2 [Abstract Only].

Staessen, Jan A. et al.; "Randomised Double-Blind Comparison of Placebo and Active Treatment for Older Patients With Isolated Systolic Hypertension"; The Lancet; bearing a date of Sep. 13, 1997; pp. 757-764; vol. 350, No. 9080 [Abstract Summary Only].

Sulaiman, S. et al.; "Human Motion Analysis Using Virtual Reality"; Research and Development, 2007; SCOReD 2007; 5th Student Conference; bearing a date of Dec. 11-12, 2007; pp. 1-4; IEEE; published in Selangor, Malaysia [Abstract Only].

Vasterling, Jennifer et al.; "Cognitive Distraction and Relaxation Training for the Control of Side Effects Due to Cancer Chemotherapy"; Journal of Behavioral Medicine; bearing a date of Feb. 1993; pp. 65-80; vol. 16, No. 1; Springer Netherlands [Abstract Only].

"Video Game May Help Detect Depression"; New Scientist; bearing a date of Mar. 10, 2007; p. 18; No. 2594.

"Virtual Reality Games Used to Distract Young Burn Victims From Pain and Anxiety"; Medical News Today; bearing a date of Sep. 29, 2007; p. 1; located at http://www.medicalnewstoday.com/articles/84055.php.

"Virtual-Reality Video Game Helps Link Depression to Specific Brain Area"; ScienceDaily; bearing a date of Mar. 2, 2007; p. 1; located at http://www.sciencedaily.com/releases/2007/03/070301100807.htm; NIH (National Institute of Mental Health).

Yamada, K. et al.; "Prediction of Medication Noncompliance in Outpatients with Schizophrenia: 2-year follow-up study"; Psychiatry Research; bearing a date of 2004; pp. 61-69; vol. 141, No. 1; Elsevier Inc. [Abstract Only].

Yoshino, Kohzoh et al.; "An Algorithm for Detecting Startle State Based on Physiological Signals"; ScienceDirect; bearing a date of 2006; pp. 1-3; located at http://www.sciencedirect.com/sciencedirect.com/science?_ob=ArticleURL&_udi=B6V5S-4M3BCCB-1&_user=10&_coverDate=03%2F31%2F2007&_alid=918001417&_rdoc=2&_fmt=high&_orig=search&_cdi=5794&_sort=d&_docanchor=&view=c&_ct=5&_acct=C000050221&_version—1&_urlVersion=0&_userid=10&md5=bc77a78ef5a694a6ecf4dc397676f14f; Elsevier B.V. [Abstract Only].

Zhang, Kuan et al.; "Measurement of Human Daily Physical Activity"; Obesity Research; bearing a date of Jan. 1, 2003; pp. 33-40; vol. 11, No. 1; NAASO.

(56) References Cited

OTHER PUBLICATIONS

Davis, Michael et al.; "Combining Pharmacotherapy With Cognitive Behavioral Therapy: Traditional and New Approaches"; Journal of Traumatic Stress; bearing a date of Oct. 2006; pp. 571-581; vol. 19, No. 5; InterScience.
IEEE 100: The Authoritative Dictionary of IEEE Standards Terms, Seventh Edition; The Institute of Electrical and Electronics Engineering Press.
Munjack, Dennis J. et al.; "Alprazolam, Propranolol, and Placebo in the Treatment of Panic Disorder and Agoraphobia with Panic Attacks"; Journal of Clinical Psychopharmacology; bearing a date of 1989; pp. 22-27; vol. 9, No. 1; Williams and Wilkins Co.
Ressler, Kerry J. et al.; "Cognitive Enhancers as Adjuncts to Psychotherapy Use of D-Cycloserine in Phobic Individuals to Facilitate Extinction of Fear"; bearing a date of Nov. 2004; pp. 1136-1144; vol. 61; Arch Gen Psychiatry.
Rothbaum, Barbara O. et al.; "Applying Learning Principles to the Treatment of Post-Trauma Reactions"; Annals New York Academy of Sciences; bearing a date of 2003; pp. 112-121; vol. 1008; New York Academy of Sciences.
Wiederhold, Brenda K.; "The Use of Virtual Reality Technology in the Treatment of Anxiety Disorders"; Information Technologies in Medicine; bearing a date of 2001; pp. 19-37; vol. II; John Wiley & Sons, Inc.
U.S. Appl. No. 12/584,200, Leuthardt et al.
U.S. Appl. No. 12/584,129, Leuthardt et al.
U.S. Appl. No. 12/462,404, Leuthardt et al.
U.S. Appl. No. 12/462,344, Leuthardt et al.
U.S. Appl. No. 12/462,197, Leuthardt et al.
U.S. Appl. No. 12/462,129, Leuthardt et al.
U.S. Appl. No. 12/460,327 Leuthardt et al.
U.S. Appl. No. 12/460,252, Leuthardt et al.
U.S. Appl. No. 12/459,623, Leuthardt et al.
U.S. Appl. No. 12/459,493, Leuthardt et al.
U.S. Appl. No. 12/459,386, Leuthardt et al.
U.S. Appl. No. 12/459,287, Leuthardt et al.
U.S. Appl. No. 12/459,195, Leuthardt et al.
U.S. Appl. No. 12/459,029, Leuthardt et al.
U.S. Appl. No. 12/455,308, Leuthardt et al.
U.S. Appl. No. 12/455,148, Leuthardt et al.
U.S. Appl. No. 12/387,961, Leuthardt et al.
Difede, Joann, Ph.D. et al.; "Virtual Reality Exposure Therapy for World Trade Center Post-traumatic Stress Disorder: A Case Report"; CyberPsychology & Behavior; 2002; pp. 529-535; vol. 5, No. 6; CyberPsychology & Behavior.
Hollifield, Michael, MD et al.; "Integrating Therapies for Anxiety Disorders"; Psychiatric Annals; May 2006; pp. 329-338; vol. 36, No. 5.
Kuzma, John M., MD et al.: "Integrating Pharmacotherapy and Psychotherapy in the Management of Anxiety Disorders"; Current Psychiatry Reports; 2004; pp. 268-273; vol. 6; Current Science Inc.
Vaiva, Guillaume et al ; "Immediate Treatment with Propranolol Decreases Posttraumatic Stress Disorder Two Months after Trauma"; Biological Psychiatry; 2003; pp. 947-949; vol. 54; Society of Biological Psychiatry.
Bonson, Katherine R.; "Hallucinogenic Drugs"; Encyclopedia of Life Sciences; bearing a date of 2001; pp. 1-7; Nature Publishing Group.
McKendree-Smith et al.; "Self-Administered Treatments for Depression: A Review"; Journal of Clinical Psychology; bearing a date of Mar. 2003; pp. 275-288; vol. 59, No. 3; Wiley Periodicals, Inc.

Pampallona et al; "Combined Pharmacotherapy and Psychological Treatment for Depression: A Systematic Review"; Arch Gen Psychiatry; bearing a date of Jul. 2004; pp. 714-719; vol. 61; American Medical Association.
"Seromycin-cycloserine capsule"; Physician's Desk Reference Digital Drug Database; bearing a revision date of Jun. 2007; pp. 1-5; PDR Network, LLC.
Silva, Alcino J. et al.; "CREB and Memory"; Annu. Rev. Neurosci.; 1998; pp. 127-137; vol. 21; Annual Reviews Inc.
IEEE 100: The Authoritative Dictionary of IEEE Standards Terms, Seventh Edition; The Institute of Electrical and Electronics Engineering Press; Dec. 2000; 10 pages; ISBN 0-7381-2601-2; The Institute of Electrical and Electronics Engineers, Inc.; New York, NY.
Lehrner et al.; "Ambient odors of orange and lavender reduce anxiety and improve mood in a dental office"; Physiology & Behavior; Apr. 27, 2005; pp. 92-95; vol. 86; Elsevier Inc.
Baños et al.; "Virtual Reality Treatment of Flying Phobia"; IEEE Transactions on Information Technology in Biomedicine; Sep. 2002; pp. 206-212; vol. 6, No. 3; IEEE.
Coelho et al.; "*Research Article* Deconstructing Acrophobia: Physiological and Psychological Precursors to Developing a Fear of Heights"; Depression and Anxiety; bearing a date of Apr. 8, 2010; pp. 864-870; vol. 27; Wiley-Liss, Inc.
Mueller et al.; "Noradrenergic modulation of extinction learning and exposure therapy"; Behavioural Brain Research; bearing a date of Dec. 1, 2009; pp. 1-11; vol. 208; Elsevier B.V.
Rothbaum et al.; "A Controlled Study of Virtual Reality Exposure Therapy for the Fear of Flying"; Journal of Consulting and Clinical Psychology; bearing a date of May 4, 2000; pp. 1020-1026; vol. 68, No. 6; American Psychological Association, Inc.
Van Gerwen et al.; "People Who Seek Help for Fear of Flying: Typology of Flying Phobics"; Behavior Therapy; bearing a date of Mar. 11, 1997; pp. 237-251; vol. 28; Association for Advancement of Behavior Therapy.
Beck et al.; "Virtual Reality Exposure Therapy for PTSD Symptoms After a Road Accident: An Uncontrolled Case Series"; Behavior Therapy; bearing a date of Sep. 22, 2006; pp. 39-48; vol. 38; Elsevier Ltd.
Garcia-Palacios et al.; "Virtual reality in the treatment of spider phobia: a controlled study"; Behaviour Research and Therapy; bearing a date of Jul. 1, 2001; pp. 983-993; vol. 40; Elsevier Science Ltd.
Valva et al.; "Fright (Effroi) and Other Peritraumatic Responses After a Serious Motor Vehicle Accident: Prospective Influence on Acute PTSD Development"; The Canadian Journal of Psychiatry-Original Research; bearing a date of Jul. 2003; pp. 395-401; vol. 48, No. 6.
Walshe et al.; "Exploring the Use of Computer Games and Virtual Reality in Exposure Therapy for Fear of Driving Following a Motor Vehicle Accident"; CyberPsychology & Behavior; bearing a date of 2003; pp. 329-334; vol. 6, No. 3; Mary Ann Liebert, Inc.
Wiederhold et al.; "Physiological Monitoring as an Objective Tool in Virtual Reality Therapy"; CyberPsychology & Behavior; bearing a date of 2002; pp. 77-82; vol. 5, No. 1; Mary Ann Liebert, Inc.
Foa et al.; "Guidelines for Treatment of PTSD"; Journal of Traumatic Stress; 2000; pp. 539-588; vol. 13, No. 4; Reprinted with permission from "*Effective Treatments for PTSD*"; Foa et al.; Guilford Press.
Wiederhold et al.; "Fear of Flying: A Case Report Using Virtual Reality Therapy with Physiological Monitoring"; Cyber Psychology and Behavior; 1998; pp. 97-103; vol. 1, No. 2; Mary Ann Liebert, Inc.
Moss et al., "Aromas of Rosemary and Lavender Essential Oils Differently Affect Cognition and Mood in Healthy Adults"; Intern. J. Neuroscience; bearing a date of Jul. 24, 2002; pp. 15-38; vol. 113; Taylor & Francis.

\* cited by examiner

FIG 3100

FIG 3104 Device (e.g., a workstation or other desktop computing device, or a mobile computing device)

FIG 3102 Computing device

FIG 3108 Storage medium

FIG 3110 Computer-executable instructions operable to:

(a) accept at least one attribute of at least one individual;

(b) query at least one database at least partly based on the at least one attribute;

(c) select from the at least one database at least one prescription medication and at least one artificial sensory experience to address the at least one attribute of at least one individual; and (d) present an indication of the at least one prescription medication and the at least one artificial sensory experience at least partly based on the selecting from the at least one database at least one prescription medication and at least one artificial sensory experience to address the at least one attribute of at least one individual

FIG 3106

FIG 3104 Device

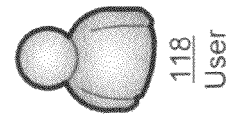
118 User

FIG 31

FIG 4304 Device (e.g., a workstation or other desktop computing device, or a mobile computing device)

FIG 4302 Computing device

FIG 4308 Storage medium

FIG 4310 Computer-executable instructions operable to:
(a) accept at least one indication of bioactive agent use by an individual;
and
(b) modify an artificial sensory experience to alter at least one effect of the bioactive agent

FIG 4304 Device

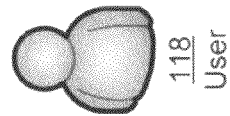
118 User

FIG 43

COMBINATION TREATMENT MODIFICATION METHODS AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/150,122, entitled COMBINATION TREATMENT SELECTION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Apr. 24, 2008, or is an application of which is entitled to the benefit of the filing date.

For purposes of the USPTO extra-statutory requirements, the present application constitutes a continuation-in-part of U.S. patent application Ser. No. 12/152,266, entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 13, 2008 now abandoned, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,275, entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 21, 2008 now U.S. Pat. No. 7,974,787, or is an application of which a currently co-pending application is entitled to the benefit of the filing date.

For purposes of the USPTO extra-statutory requirements, the present application constitutes a continuation-in-part of U.S. patent application Ser. No. 12/156,440, entitled COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 30, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/156,949, entitled SIDE EFFECT AMELIORATING COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 5, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to methods and systems for combining medicine with an artificial sensory experience.

SUMMARY

In one aspect, a method includes but is not limited to accepting at least one indication of bioactive agent use by an individual and modifying an artificial sensory experience to alter at least one effect of the bioactive agent. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting at least one indication of bioactive agent use by an individual and means for modifying an artificial sensory experience to alter at least one effect of the bioactive agent. In addition to the foregoing, other method aspects are described in the claims, drawings, and text forming a part of the present disclosure.

In one aspect, a system includes but is not limited to circuitry for accepting at least one indication of bioactive agent use by an individual and circuitry for modifying an artificial sensory experience to alter at least one effect of the bioactive agent. In addition to the foregoing, other method aspects are described in the claims, drawings, and text forming a part of the present disclosure.

In one aspect, a computer program product includes but is not limited to a signal-bearing medium bearing one or more instructions for accepting at least one indication of bioactive agent use by an individual and one or more instructions for modifying an artificial sensory experience to alter at least one effect of the bioactive agent. In addition to the foregoing, other method aspects are described in the claims, drawings, and text forming a part of the present disclosure.

In one aspect, a system includes but is not limited to a computing device and instructions that when executed on the computing device cause the computing device to accept at least one indication of bioactive agent use by an individual and modify an artificial sensory experience to alter at least one effect of the bioactive agent. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 31 illustrates a system related to selecting a combination of at least one prescription medication and at least one artificial sensory experience.

FIG. 43 illustrates a system related to selecting a combination of at least one prescription medication and at least one artificial sensory experience.

DETAILED DESCRIPTION

Figure 1:
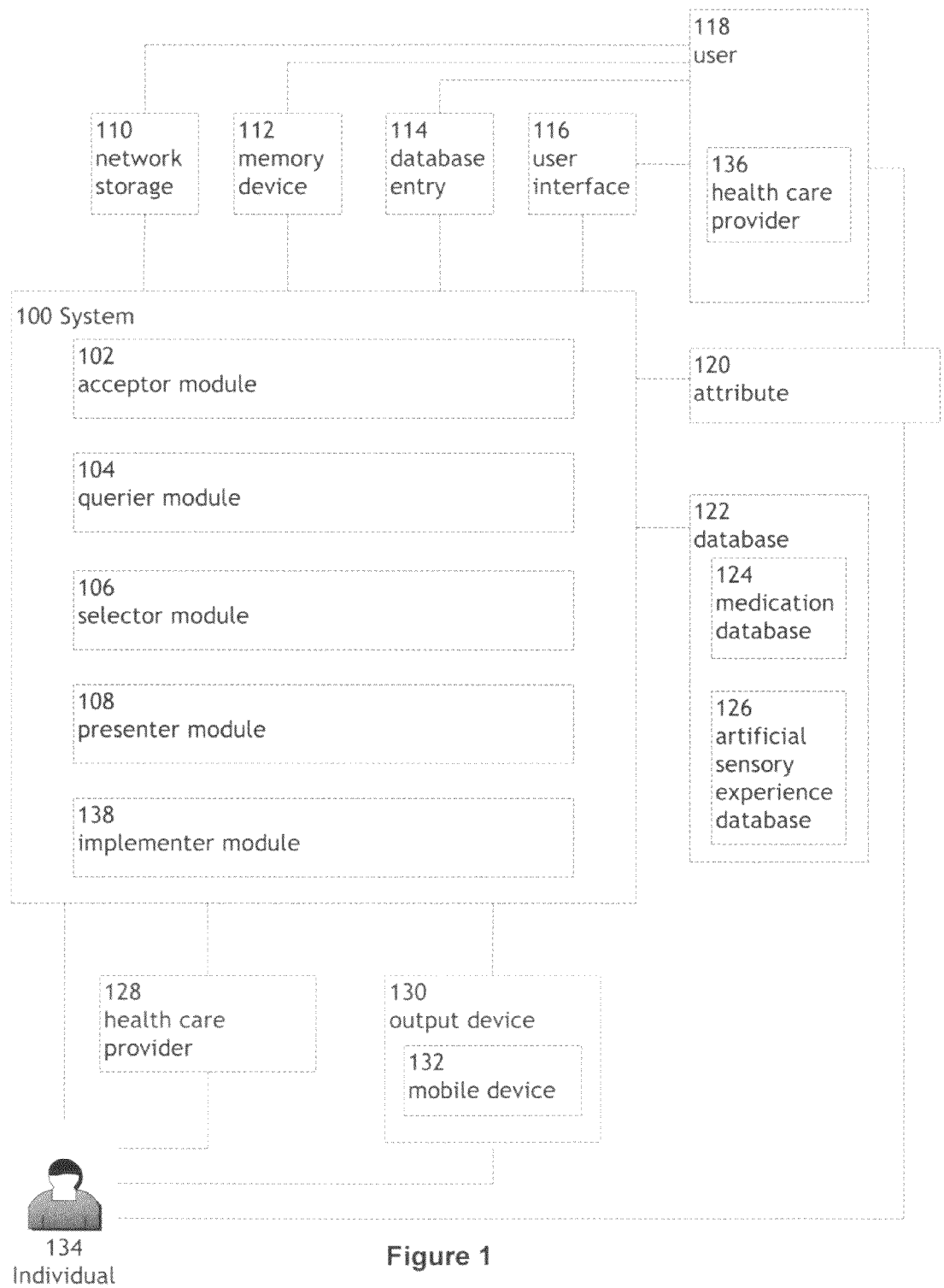
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates a system 100 for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The system 100 may include acceptor module 102, querier module 104, selector module 106, presenter module 108, implementer module 138, and/or modifier module 140. Acceptor module 102 may receive attribute 120 from network storage 110, memory device 112, database entry 114, and/or user interface 116. User interface 116 may receive information from user 118. User 118 may include health care provider 136. Querier module 104 may search database 122. Database 122 may include medication database 124 and/or artificial sensory experience database 126. Presenter module 108 may present to health care provider 128, output device 130, and/or individual 134. Output device 130 may include mobile device 132. Modifier module 140 may include restrictor module 142, granter module 144, alterer module 146, adder module 148, deleter module 150, and/or acceptor module 152. System 100 generally represents instrumentality for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The operations of accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual may be accomplished electronically, such as with a set of interconnected electrical components, an integrated circuit, and/or a computer processor.

Figure 2:
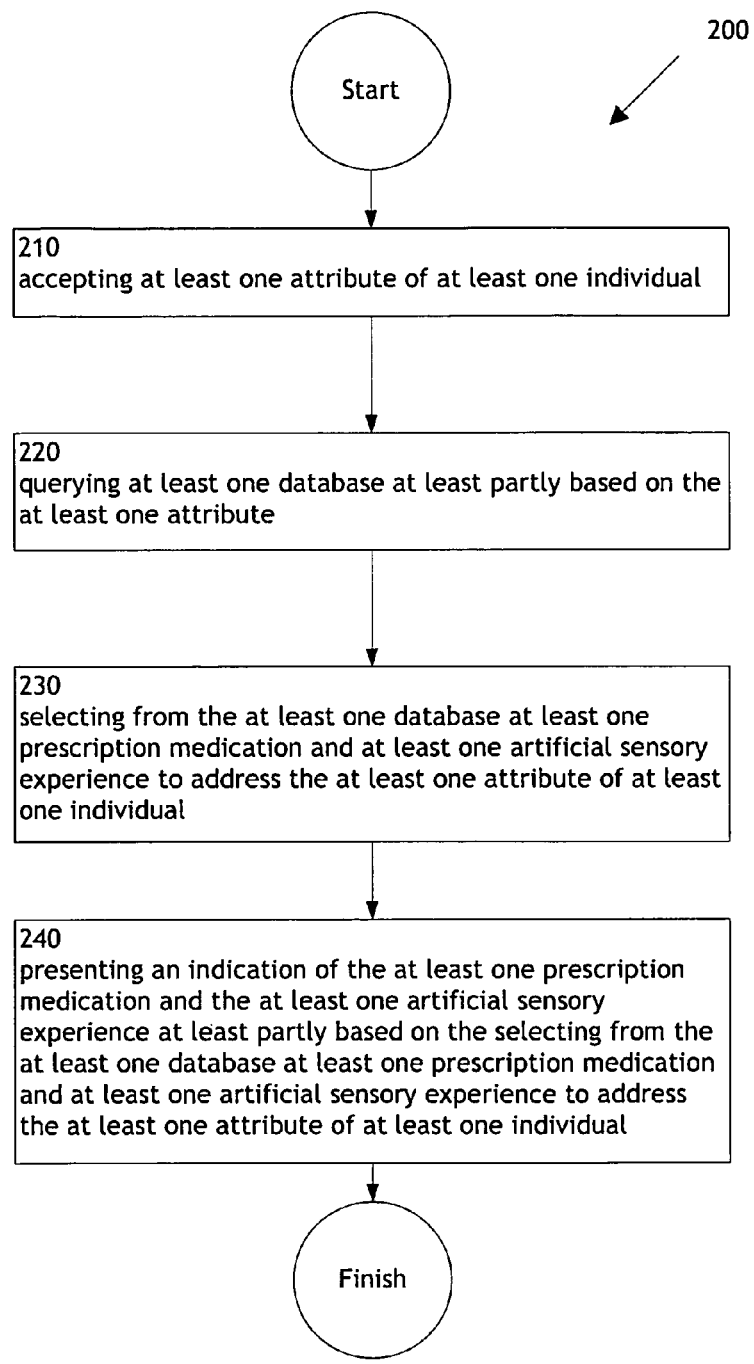
FIG. 2 illustrates an operational flow representing example operations related to selecting a combination of at least one prescription medication and at least one artificial sensory experience.

FIG. 2 illustrates an operational flow 200 representing example operations related to accepting at least one attribute of at least one individual, querying at least one database at least partly based on the at least one attribute, selecting from the at least one database at least one prescription medication and at least one artificial sensory experience to address the at least one attribute of at least one individual, and/or presenting an indication of the at least one prescription medication and the at least one artificial sensory experience at least partly based on the selecting from the at least one database at least one prescription medication and at least one artificial sensory experience to address the at least one attribute of at least one individual. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to an operation 210. Operation 210 depicts accepting at least one attribute of at least one individual. For example, as shown in FIG. 1, acceptor module 102 may accept at least one attribute of at least one individual. In one instance, acceptor module 102 can accept from a user 118 and a user interface 116 an attribute 120 including an attribute of a personal health history associated with an individual named John Smith. In some instances, acceptor module 102 may include a computer processor.

Then, operation 220 depicts querying at least one database at least partly based on the at least one attribute. For example, as shown in FIG. 1, querier module 104 may search at least one database at least partly based on the at least one attribute. In one example and continuing with the previous example, querier module 104 can search a database 122 including a medication database 124 and artificial sensory experience database 126 at least partly based on the attribute including an attribute of a personal health history associated with an individual named John Smith. In some instances, querier module 104 may include a computer processor.

Then, operation 230 depicts selecting from the at least one database at least one prescription medication and at least one artificial sensory experience to address the at least one attribute of at least one individual. For example, as shown in FIG. 1, selector module 106 may select from the at least one database at least one prescription medication and at least one artificial sensory experience to address the at least one attribute of at least one individual. In one instance and continuing with the previous example, selector module 106 can select from a medication database 124 and artificial sensory experience database 126 a prescription medication and an artificial sensory experience for addressing the attribute 120 including an attribute of a personal health history associated with an individual named John Smith. In some instances, selector module 106 may include a computer processor.

Then, operation 240 depicts presenting an indication of the at least one prescription medication and the at least one artificial sensory experience at least partly based on the selecting from the at least one database at least one prescription medication and at least one artificial sensory experience to address the at least one attribute of at least one individual. For example, as shown in FIG. 1, presenter module 108 may present the at least one prescription medication and the at least one artificial sensory experience at least partly based on the searching at least one database at least partly based on the at least one attribute. In one instance and continuing with the previous example, presenter module 108 can present to a medical professional the prescription medication and the artificial sensory experience based on searching the medication database 124 and artificial sensory experience database 126 based on the at least one attribute 120 including an attribute of a personal health history associated with an individual named John Smith. In some instances, presenter module 108 may include a computer processor.

Figure 3:
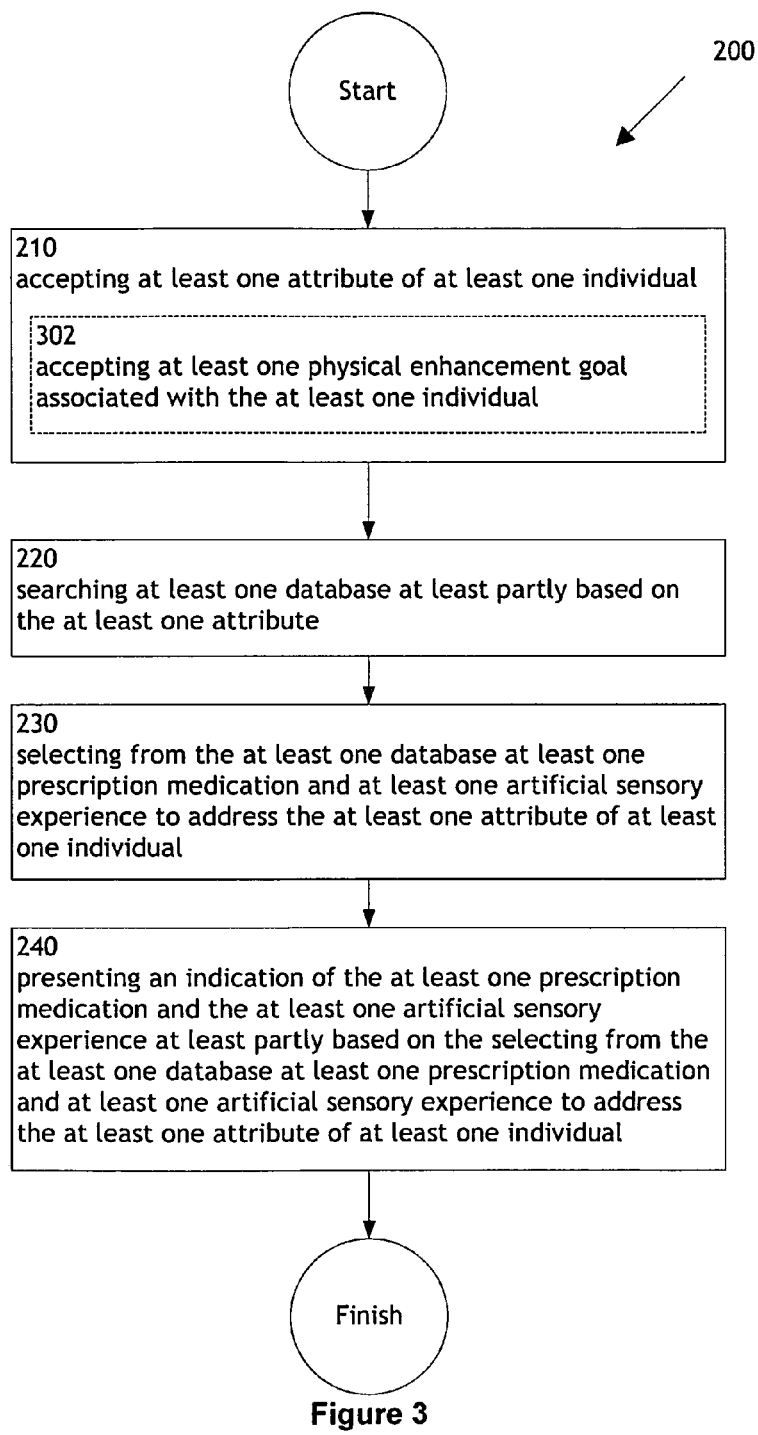
FIG. 3 illustrates an alternative embodiment of the operational flow of FIG. 2.

FIG. 3 illustrates alternative embodiments of the example operational flow 200 of FIG. 2. FIG. 3 illustrates example embodiments where the operation 210 may include at least one additional operation. Additional operations may include an operation 302.

Operation 302 illustrates accepting at least one physical enhancement goal associated with the at least one individual. For example, as shown in FIG. 1, acceptor module 102 may accept from a database entry 114 at least one physical enhancement goal associated with the at least one individual. In one instance and continuing with the above example, acceptor module 102 accepts from memory device 112 at least one physical enhancement goal associated with an individual named John Smith. A physical enhancement goal may include a physical state and/or situation an individual may plan to achieve. Some examples of a physical enhancement goal may include achieving a certain state of relaxation, reaching a certain body mass, maintaining a specific cholesterol level, achieving an athletic performance goal, and/or lowering a blood pressure level. In some instances, acceptor module 102 may include a computer processor.

Figure 4:
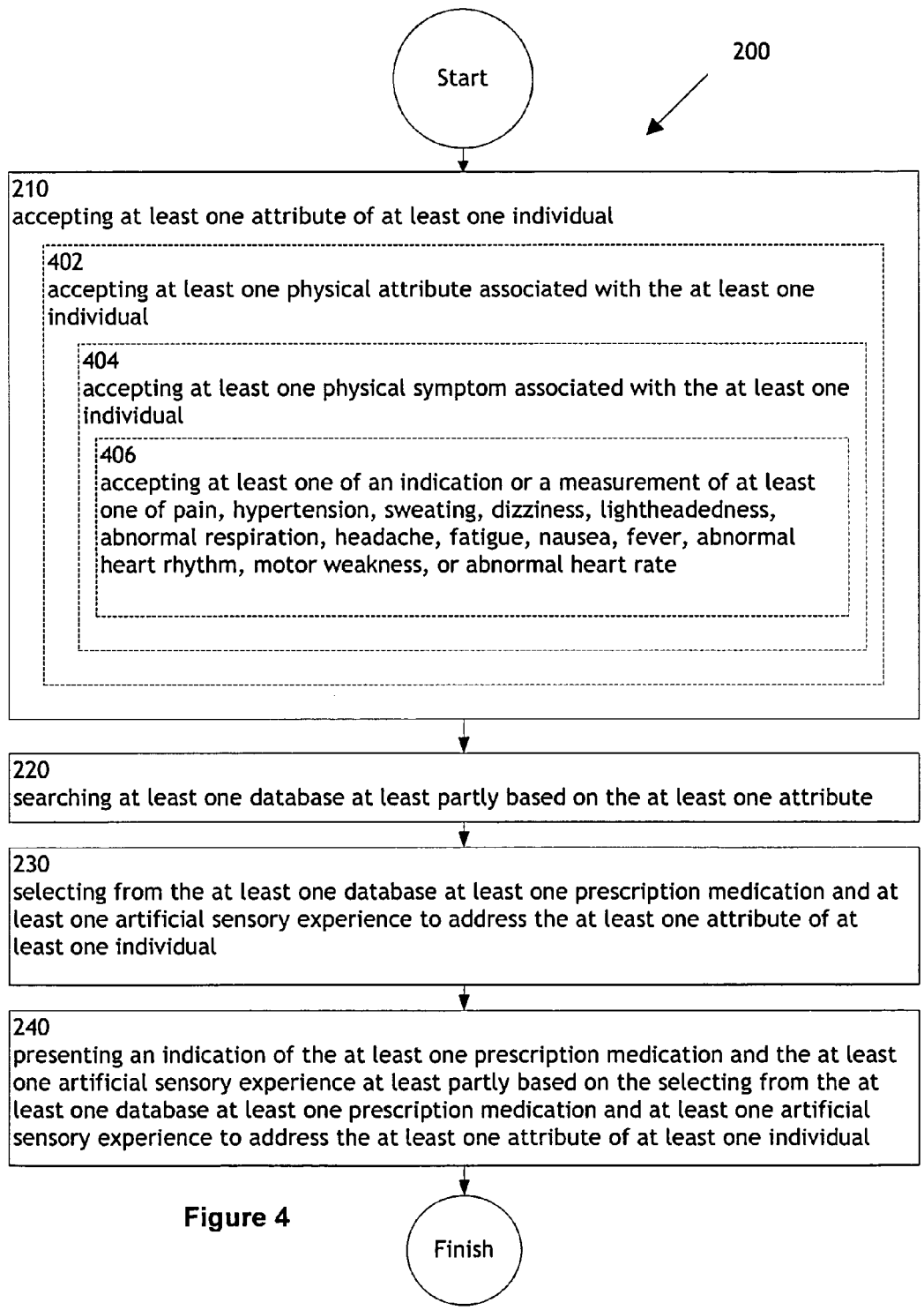
FIG. 4 illustrates an alternative embodiment of the operational flow of FIG. 2.

FIG. 4 illustrates alternative embodiments of the example operational flow 200 of FIG. 2. FIG. 4 illustrates example embodiments where the operation 210 may include at least one additional operation. Additional operations may include an operation 402, an operation 404, and/or an operation 406.

Operation 402 illustrates accepting at least one physical attribute associated with the at least one individual. For example, as shown in FIG. 1, acceptor module 102 may accept from network storage 110 at least one physical attribute associated with the at least one individual. In one instance, acceptor module 102 can accept a physical attribute 120 associated with a group of twenty individuals including an individual weight for each individual. A physical attribute may include an attribute that may be described and/or detected using senses, that has substance and/or a material existence, and/or that may be acted upon by physical force. Some examples of a physical attribute may include a biochemical measurement such as blood sugar level, a smell, an appearance, a physiological measurement such as blood pressure, and/or skin conductivity. In some instances, acceptor module 102 may include a computer processor.

Operation 404 illustrates accepting at least one physical symptom associated with the at least one individual. For example, as shown in FIG. 1, acceptor module 102 may accept at least one physical symptom associated with the at least one individual. In one example, acceptor module 102 can accept from a user 118 and/or user interface 116 a physical symptom including an indication of influenza such as a fever associated with an individual named Mark White. A physical symptom may include a manifestation, sign, and/or an indication of the presence of a disease and/or some other bodily disorder and/or abnormality. Some examples of a physical symptom may include pain, swelling, fever, rash, and/or discoloration. In some instances, acceptor module 102 may include a computer processor.

Operation 406 illustrates accepting at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIG. 1, acceptor module 102 may accept from at least one of an indication or a measurement of at least one of pain, high blood pressure, sweating, dizziness, lightheadedness, abnormal respiration, headache, fatigue, nausea, fever, abnormal heart rhythm, motor weakness, or abnormal heart rate. In one example, acceptor module 102 can accept an indication of pain and a measurement of high blood pressure from network storage 110. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, acceptor module 102 may include a computer processor.

Figure 5:
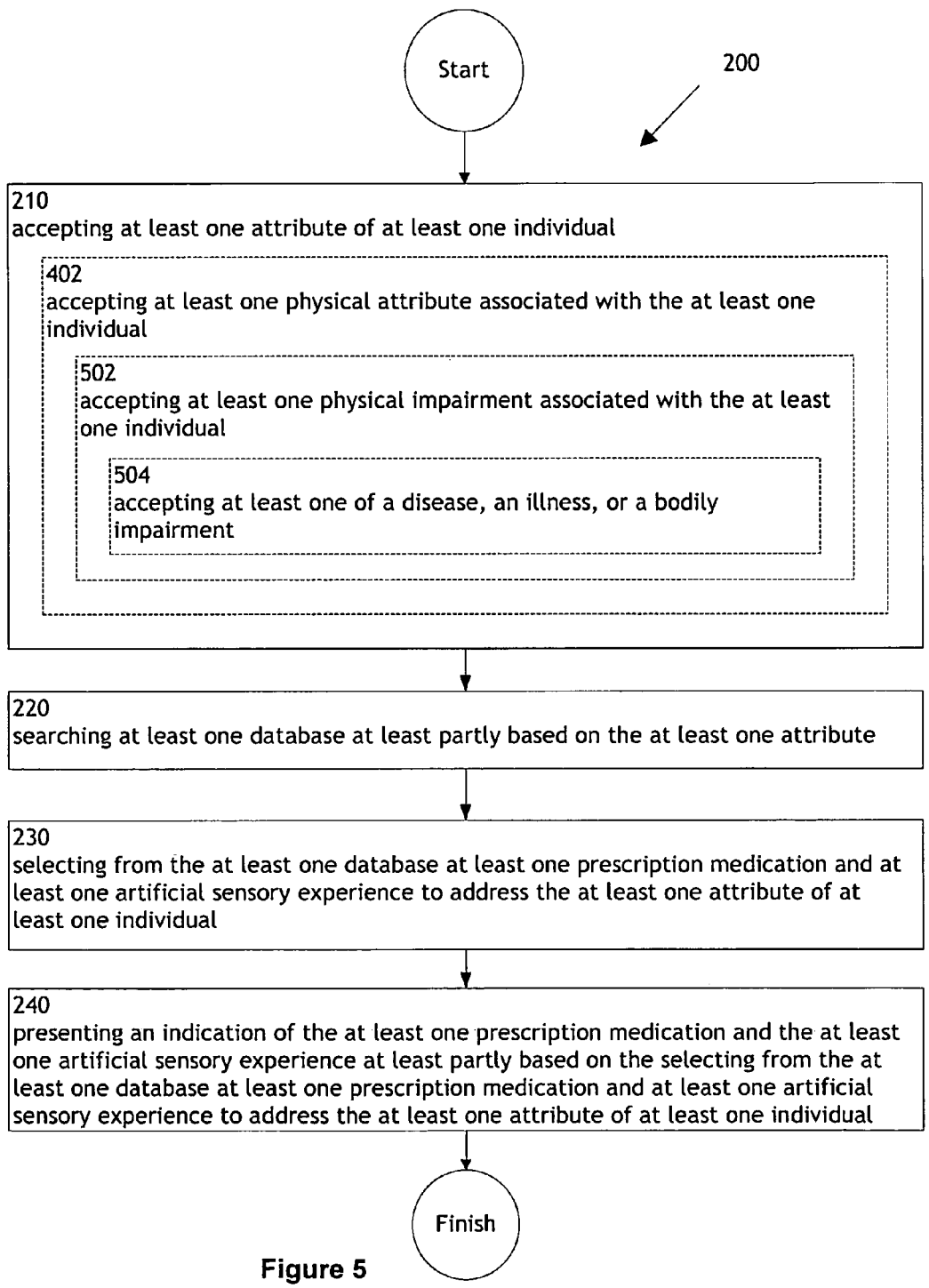
FIG. 5 illustrates an alternative embodiment of the operational flow of FIG. 2.

FIG. 5 illustrates alternative embodiments of the example operational flow 200 of FIG. 2. FIG. 5 illustrates example embodiments where the operation 210 may include at least one additional operation. Additional operations may include an operation 502, and/or an operation 504. Further, operation 502 illustrates accepting at least one physical impairment associated with the at least one individual. For example, as shown in FIG. 1, acceptor module 102 may accept at least one physical impairment associated with the at least one individual from a user 118 and a user interface 116. In one instance, acceptor module 102 accepts a physical impairment including a bodily impairment associated with an individual named Fred Johnson from a user 118 and/or a user interface 116. A physical impairment may include a condition or function judged to be significantly impaired relative to the usual standard of an individual of their group and may include physical impairment, sensory impairment, and/or disease. In some instances, acceptor module 102 may include a computer processor.

Operation 504 illustrates accepting at least one of a disease, an illness, or a bodily impairment. For example, as shown in FIG. 1, acceptor module 102 may accept at least one of a disease, an illness, or a bodily impairment. In one example, acceptor module 102 accepts an indication of a disease and a bodily impairment from database entry 114. A disease may include an abnormal condition of an organism that impairs bodily functions associated with one or more specific symptoms and signs and may include discomfort, distress, dysfunction, injury, a disorder, a syndrome, infection, and/or other atypical variation associated with structure and/or function of the body. An illness may include any state of poor health. Some examples of an illness may include cancer, the common cold, influenza, pneumonia, and/or high cholesterol.

A bodily impairment may include a diminished ability in body function and/or structure. In some instances, acceptor module 102 may include a computer processor.

Figure 6:
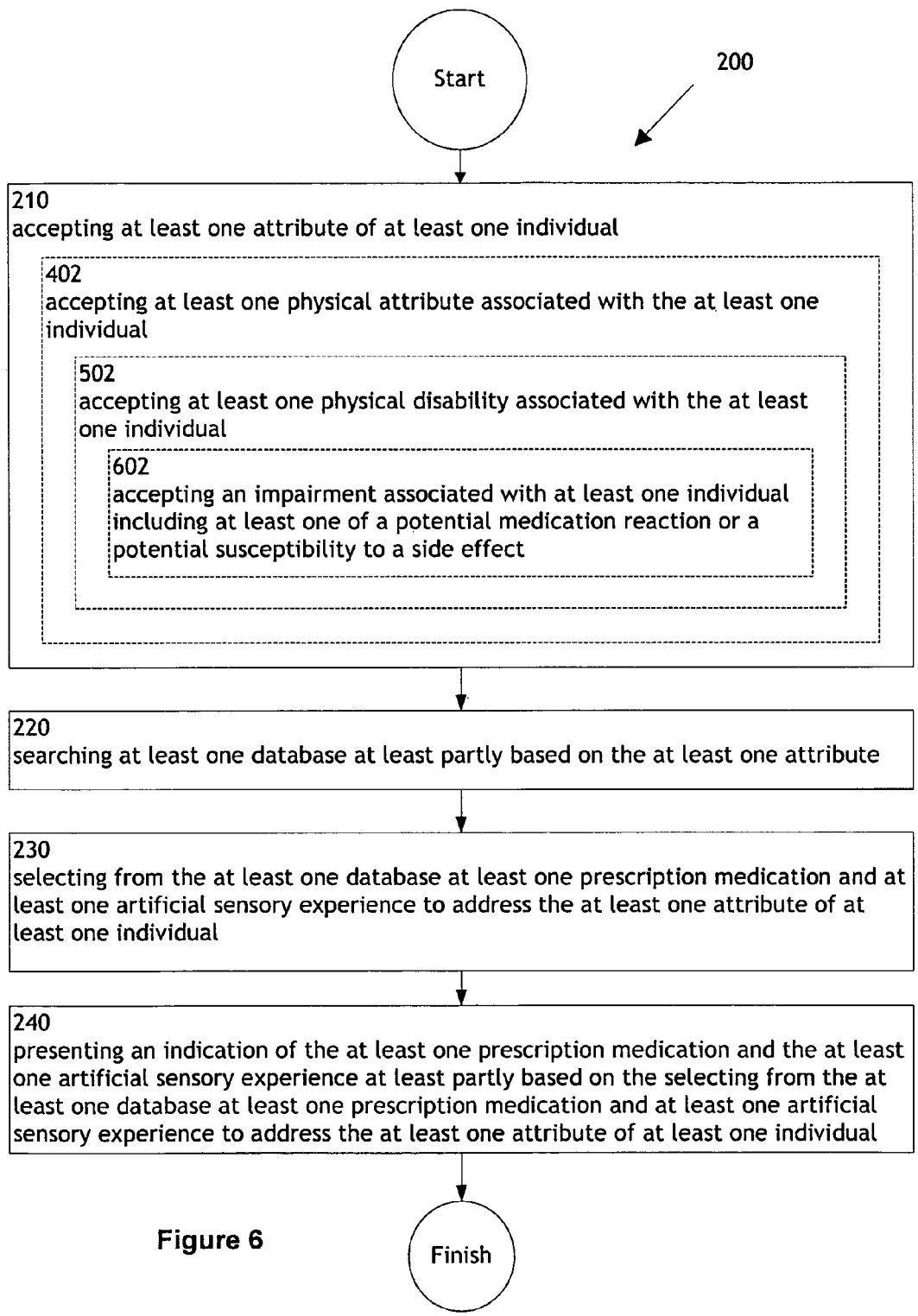
FIG. 6 illustrates an alternative embodiment of the operational flow of FIG. 2.

FIG. 6 illustrates alternative embodiments of the example operational flow 200 of FIG. 2. FIG. 6 illustrates example embodiments where operation 210 may include at least one additional operation. Additional operations may include an operation 602. Operation 602 illustrates accepting an impairment associated with at least one individual including at least one of a potential medication reaction or a potential susceptibility to a side effect. For example, as shown in FIG. 1, acceptor module 102 may accept an impairment associated with at least one individual including at least one of a potential medication reaction or a potential susceptibility to a side effect. In one example, acceptor module 102 can accept from network storage 110 an impairment associated with at least one individual including at least one of a potential medication reaction or a potential susceptibility to a side effect. A potential medication reaction may include a possible response a person may exhibit resulting from at least one drug and/or medication administered to the person. A potential medication reaction may include an allergy and/or a drug and/or medication interaction with a separate drug and/or medication. A potential susceptibility to a side effect may include the probability a certain person may be vulnerable to a side effect coupled with a specific drug and/or medication. In some instances, acceptor module 102 may include a computer processor.

Figure 7:
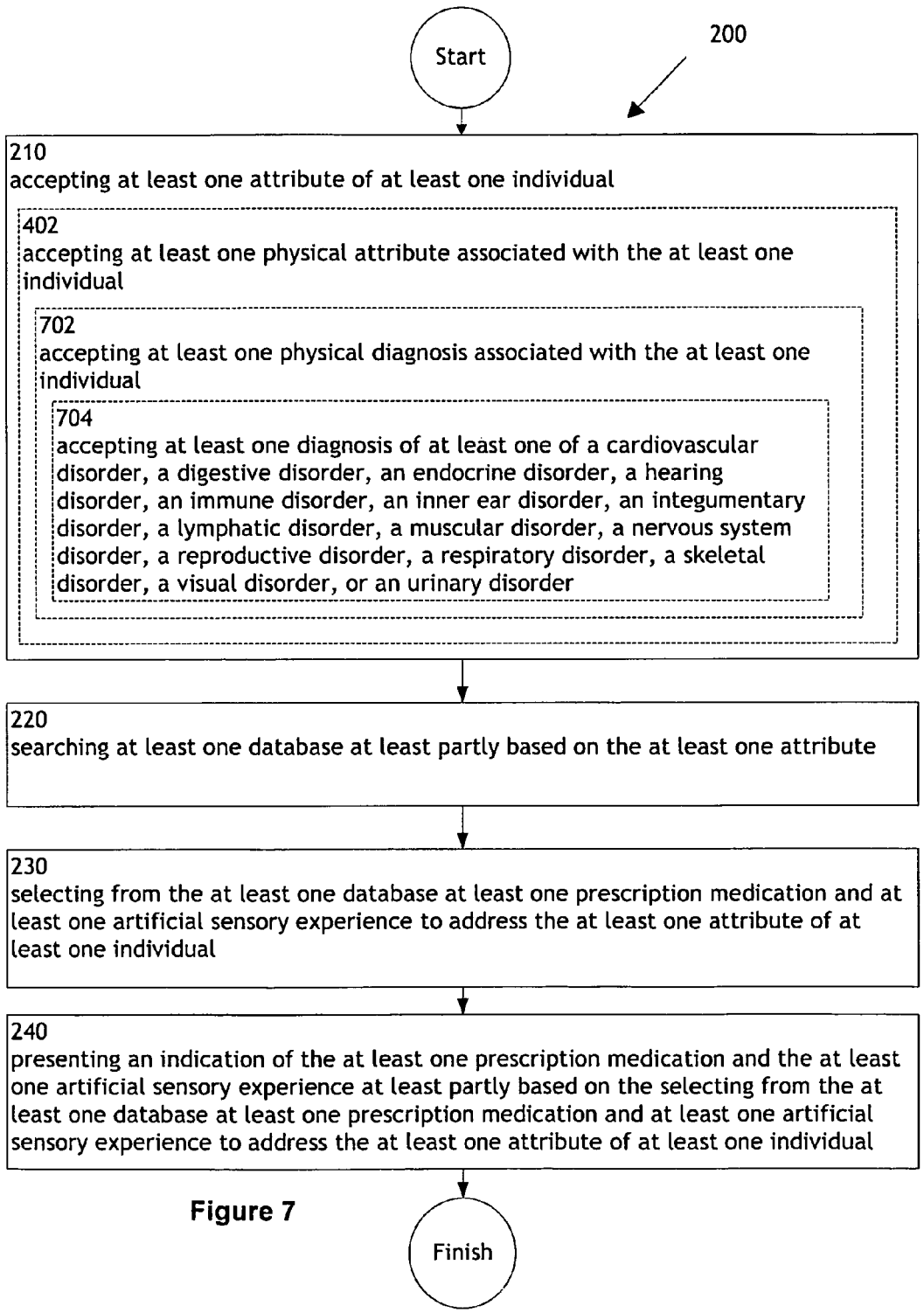
FIG. 7 illustrates an alternative embodiment of the operational flow of FIG. 2.

FIG. 7 illustrates alternative embodiments of the example operational flow 200 of FIG. 2. FIG. 7 illustrates example embodiments where the operation 210 may include at least one additional operation. Additional operations may include an operation 702, and/or an operation 704. Further, operation 702 illustrates accepting at least one physical diagnosis associated with the at least one individual. For example, as shown in FIG. 1, acceptor module 102 may accept at least one physical diagnosis associated with the at least one individual. In a specific example, acceptor module 102 accepts from memory device 112 a physical diagnosis associated with a group of ten individuals. A physical diagnosis may include identifying a disease and/or condition by its outward signs and/or symptoms. Some examples of a physical diagnosis may include identifying influenza and/or identifying Alzheimer's disease. In some instances, acceptor module 102 may include a computer processor.

Operation 704 illustrates accepting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIG. 1, acceptor module 102 may accept at least one diagnosis of at least one of a cardiovascular disorder, a digestive disorder, an endocrine disorder, an integumentary disorder, a lymphatic disorder, a muscular disorder, a nervous system disorder, a reproductive disorder, a respiratory disorder, a skeletal disorder, or an urinary disorder. In a specific instance, acceptor module 102 can accept from user interface 116 and/or user 118 a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, stomach ulcers including those associated with *H. pylori* infection, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, loss due to death of auditory hair cells, for example that caused by trauma, and/or unilateral hearing loss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or lack of function in the eye and/or in visual perception. Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, acceptor module 102 may include a computer processor.

Figure 8:
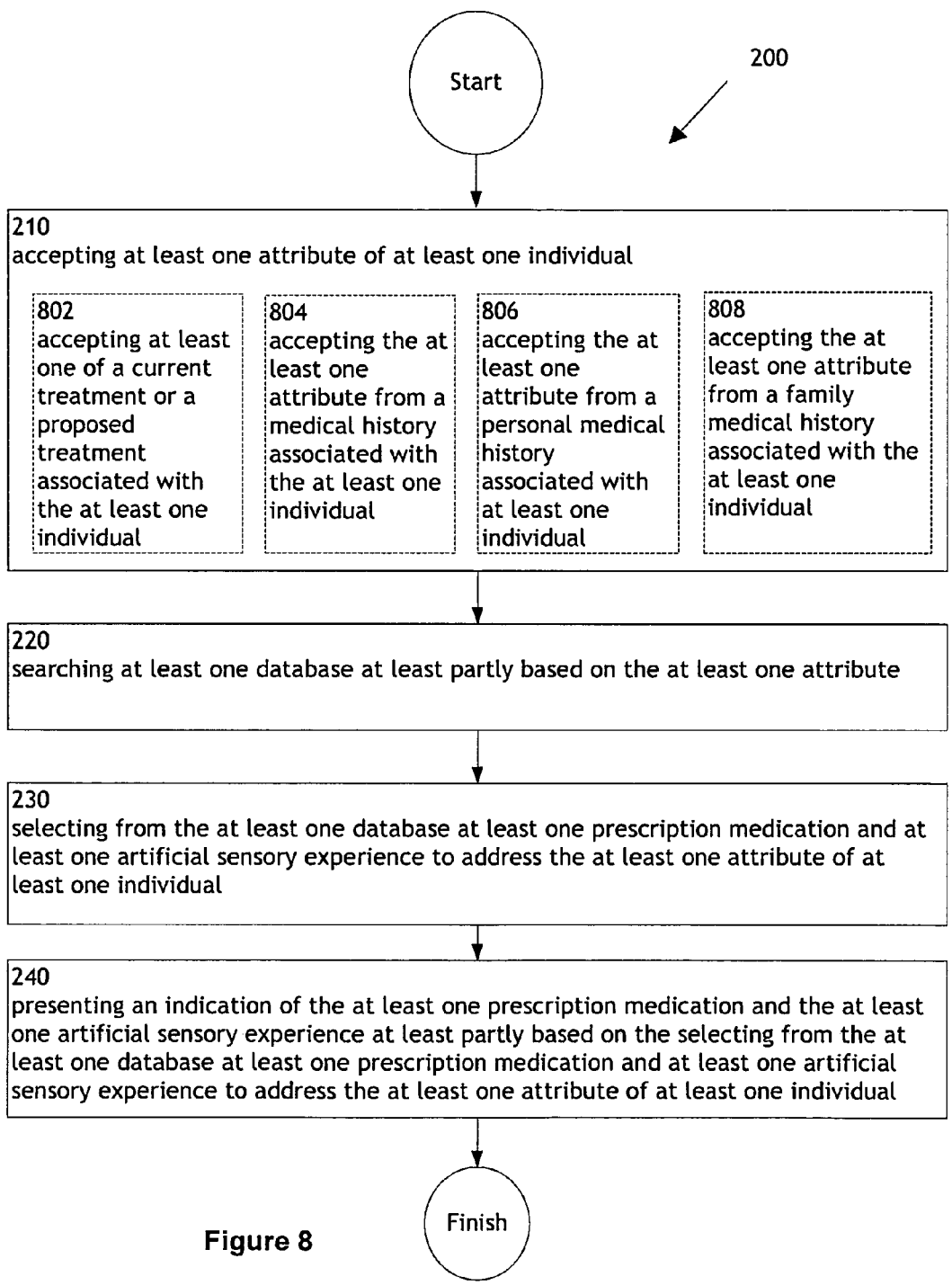
FIG. 8 illustrates an alternative embodiment of the operational flow of FIG. 2.

FIG. 8 illustrates alternative embodiments of the example operational flow 200 of FIG. 2. FIG. 8 illustrates example embodiments where the operation 210 may include at least one additional operation. Additional operations may include an operation 802, an operation 804, an operation 806, and/or operation 808.

Operation 802 illustrates accepting at least one of a current treatment or a proposed treatment associated with the at least one individual. For example, as shown in FIG. 1, acceptor module 102 may accept at least one of a current treatment or a proposed treatment associated with the at least one individual. In one instance, acceptor module 102 accepts a current treatment regime associated with an individual named Cathy Hansen. A current treatment may include one or a series of treatments recommended, administered, and/or prescribed for a certain individual. A proposed treatment may include one or a series of treatments recommended, prescribed, and/or not currently administered to a certain individual. In some instances, acceptor module 102 may include a computer processor.

Operation 804 illustrates accepting the at least one attribute from a medical history associated with the at least one individual. For example, as shown in FIG. 1, acceptor module 102 may accept the at least one attribute from a medical history associated with the at least one individual. In one example, acceptor module 102 may accept from database entry 114 an attribute 120 from a medical history including the number of blood relatives with diabetes associated with an individual named Emily Smith. A medical history may include a list of previous illnesses, symptoms, medicines, treatments, health risk factors, operations, and/or doctor visits for an individual and/or a relation of an individual. In some instances, acceptor module 102 may include a computer processor.

Operation 806 illustrates accepting the at least one attribute from a personal medical history associated with at least one individual. For example, as shown in FIG. 1, acceptor module 102 may accept the at least one attribute from a personal medical history associated with at least one individual. In a specific instance, acceptor module 102 can accept from database entry 114 an attribute 120 including, for example, a list of operations from a personal medical history associated with an individual named Robert Murphy. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, acceptor module 102 may include a computer processor.

Operation 808 illustrates accepting the at least one attribute from a family medical history associated with the at least one individual. For example, as shown in FIG. 1, acceptor module 102 may accept the at least one attribute from a family medical history associated with the at least one individual. In one example, acceptor module 102 can accept from network storage 110 an attribute 120 including a list of family members that have had ovarian cancer from a family medical history associated with an anonymous individual or an individual named Elizabeth Green. A family medical history may include a list of previous illnesses, symptoms, medicines, treatments, health risk factors, operations, and/or doctor visits associated with family members related to the at least one individual. In some instances, acceptor module 102 may include a computer processor.

Figure 9:
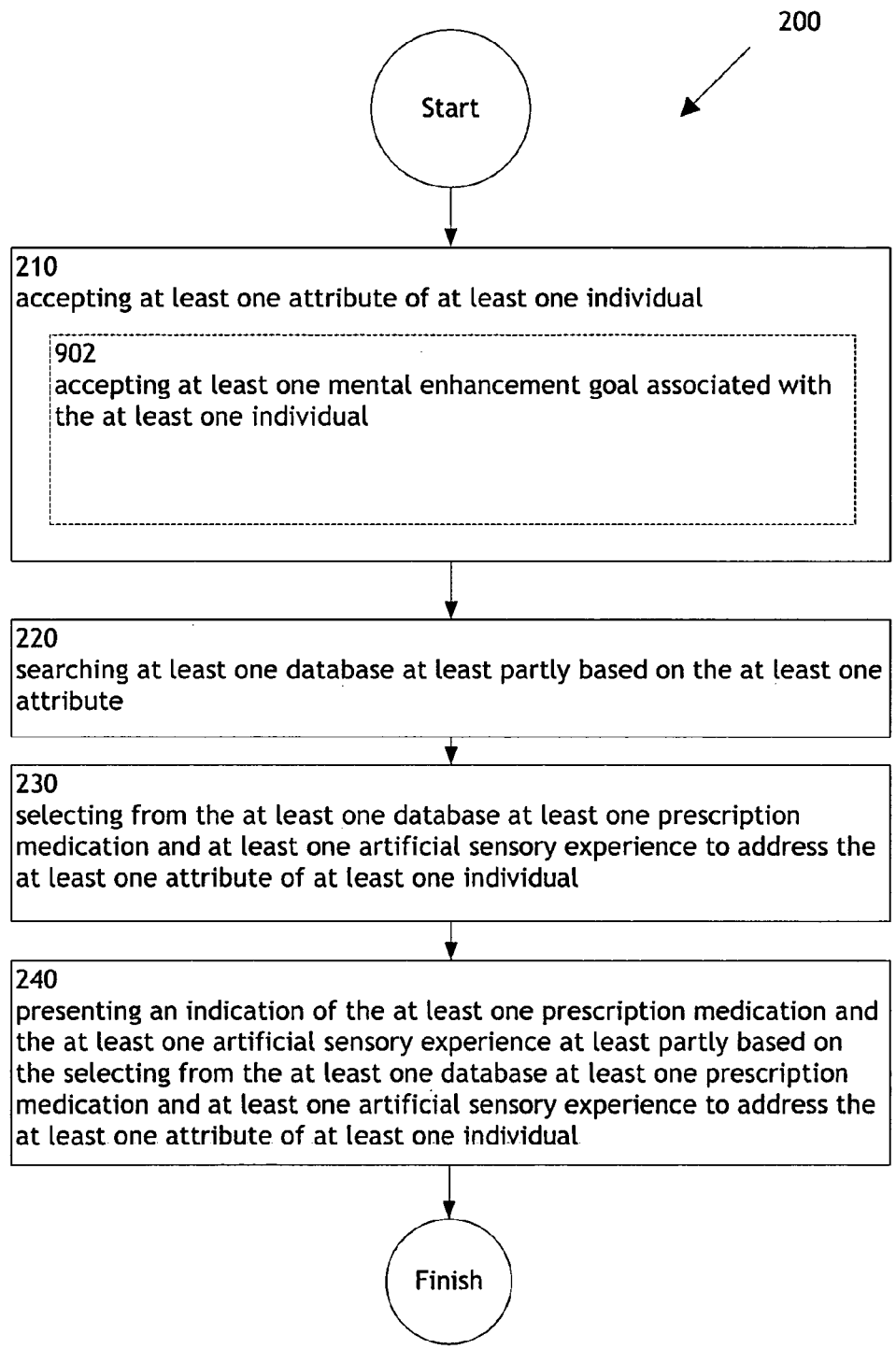
FIG. 9 illustrates an alternative embodiment of the operational flow of FIG. 2.

FIG. 9 illustrates alternative embodiments of the example operational flow 200 of FIG. 2. FIG. 9 illustrates example embodiments where operation 210 may include at least one additional operation. Additional operations may include an operation 902.

Operation 902 illustrates accepting at least one mental enhancement goal associated with the at least one individual. For example, as shown in FIG. 1, acceptor module 102 may accept at least one mental enhancement goal associated with the at least one individual. In one instance, acceptor module 102 can accept a mental enhancement goal associated with, for example, an individual named Dorothy Anderson. A mental enhancement goal may include a mental state and/or situation an individual may plan to achieve. Some examples of a mental enhancement goal may include achieving a certain state of mental awareness such as increased alertness or visual perception, reaching a certain cognitive capability such as enhanced memory or pattern recognition, maintaining a specific attention level, and/or reducing or eliminating a phobia. In some instances, acceptor module 102 may include a computer processor.

Figure 10:
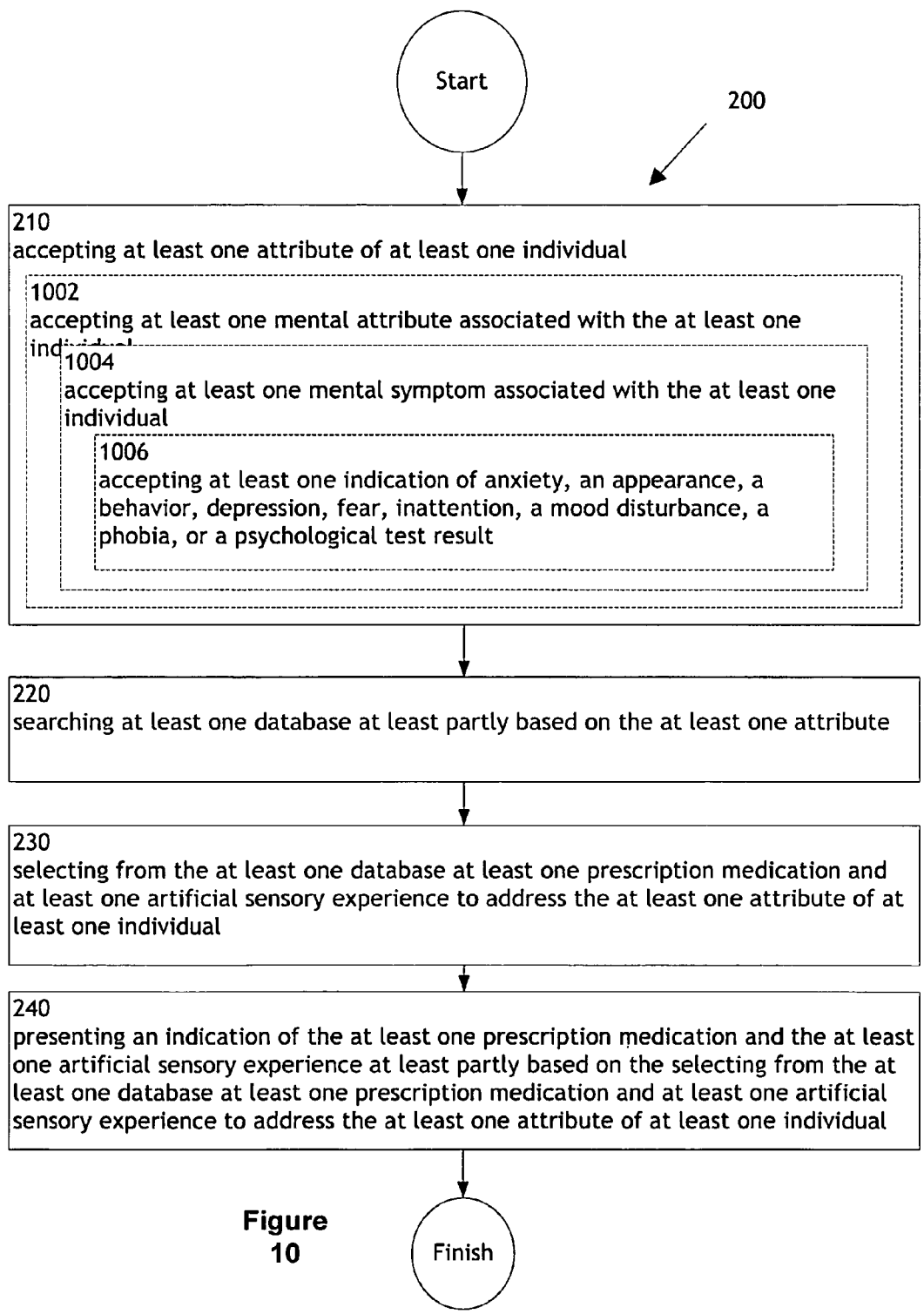
FIG. 10 illustrates an alternative embodiment of the operational flow of FIG. 2.

FIG. 10 illustrates alternative embodiments of the example operational flow 200 of FIG. 2. FIG. 10 illustrates example embodiments where operation 210 may include at least one additional operation. Additional operations may include an operation 1002, an operation 1004, and/or an operation 1006.

Operation 1002 illustrates accepting at least one mental attribute associated with the at least one individual. For example, as shown in FIG. 1, acceptor module 102 may accept at least one mental attribute associated with the at least one individual. In one example, acceptor module 102 can accept a mental attribute 120 including, for example, an intelligence quotient associated with an individual named Judy Peterson. A mental attribute may include an attribute that may be related to and/or associated with basic mental function and/or high-level brain function. Some examples of a mental attribute may include an intelligence quotient (IQ), measurements of brain activity for example using functional MRI or near infra-red technology, and/or measurements of mental development. In some instances, acceptor module 102 may include a computer processor.

Operation 1004 illustrates accepting at least one mental symptom associated with the at least one individual. For example, as shown in FIG. 1, acceptor module 102 may accept at least one mental symptom associated with the at least one individual. In one example, acceptor module 102 can accept from network storage 110 a mental symptom including a stress level measurement associated with an individual named Heather Swanson. A mental symptom may include a manifestation, sign, and/or an indication of the presence of a disease and/or some other mental disorder and/or abnormality. Some examples of a mental symptom may include lack of attention, indication of stress, -hyperactivity, nervousness, and/or lack of responsiveness. In some instances, acceptor module 102 may include a computer processor.

Operation 1006 illustrates accepting at least one indication of anxiety, an appearance, a behavior, depression, fear, inattention, a mood disturbance, a phobia, or a psychological test result. For example, as shown in FIG. 1, acceptor module 102 may accept at least one indication of anxiety, appearance, behavior, depression, fear, inattention, mood disturbance, phobia, or psychological test result. In one example, acceptor module 102 can accept from user interface 116 and user 118 an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a tack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, acceptor module 102 may include a computer processor.

Figure 11:
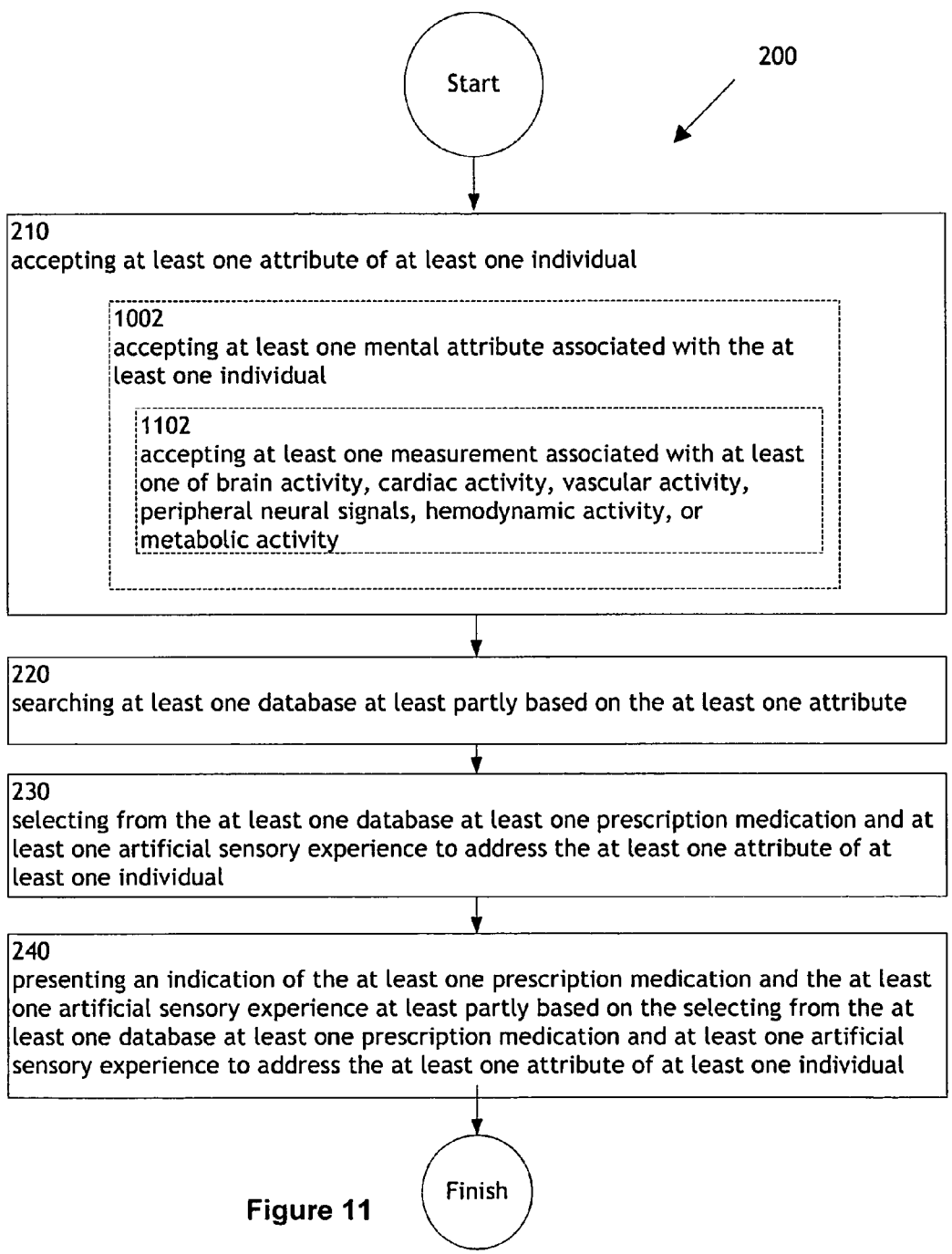
FIG. 11 illustrates an alternative embodiment of the operational flow of FIG. 2.

FIG. 11 illustrates alternative embodiments of the example operational flow 200 of FIG. 2. FIG. 11 illustrates example embodiments where operation 210 may include at least one additional operation. Additional operations may include an operation 1102.

Operation 1102 illustrates accepting at least one measurement associated with at least one of brain activity, cardiac activity, vascular activity, peripheral neural signals, hemodynamic activity, or metabolic activity. For example, as shown in FIG. 1, acceptor module 102 may accept at least one measurement associated with at least one of brain activity, cardiac activity, vascular activity, peripheral neural signals, hemodynamic activity, or metabolic activity. In one instance, acceptor module 102 can accept from database entry 114 a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, acceptor module 102 may include a computer processor.

Figure 12:
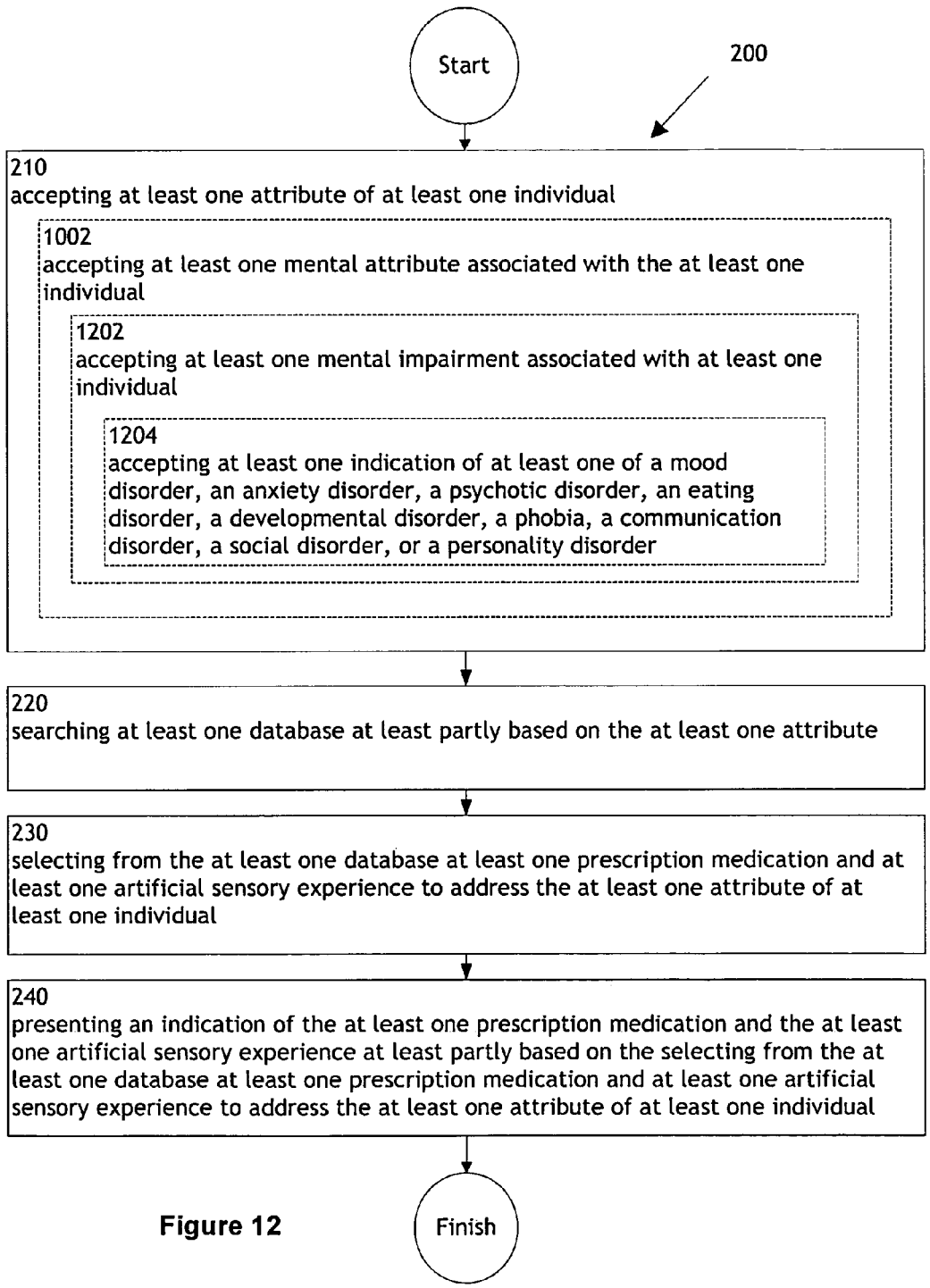
FIG. 12 illustrates an alternative embodiment of the operational flow of FIG. 2.

FIG. 12 illustrates alternative embodiments of the example operational flow 200 of FIG. 2. FIG. 12 illustrates example embodiments where operation 210 may include at least one additional operation. Additional operations may include an operation 1202, and/or an operation 1204.

Operation 1202 illustrates accepting at least one mental impairment associated with at least one individual. For example, as shown in FIG. 1, acceptor module 102 may accept at least one mental impairment associated with at least one individual. In one example, acceptor module 102 can accept from memory device 112 a mental impairment associated with an individual named Richard Lewis. A mental impairment may include a condition or function judged by a health care provider to be significantly impaired relative to the usual standard of an individual of their group, and may include mental impairment, sensory impairment, and/or mental disease. In some instances, acceptor module 102 may include a computer processor.

Operation 1204 illustrates accepting at least one indication of at least one of a mood disorder, an anxiety disorder, a psychotic disorder, an eating disorder, a developmental disorder, a phobia, a communication disorder, a social disorder, or a personality disorder. For example, as shown in FIG. 1, acceptor module 102 may accept at least one indication of at least one of a mood disorder, an anxiety disorder, a psychotic disorder, an eating disorder, a developmental disorder, a phobia, or a personality disorder. In one instance, acceptor module 102 can accept from user interface 116 and/or user 118 an indication of a mood disorder including a mood change and the onset of depression in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, acceptor module 102 may include a computer processor.

Figure 13:
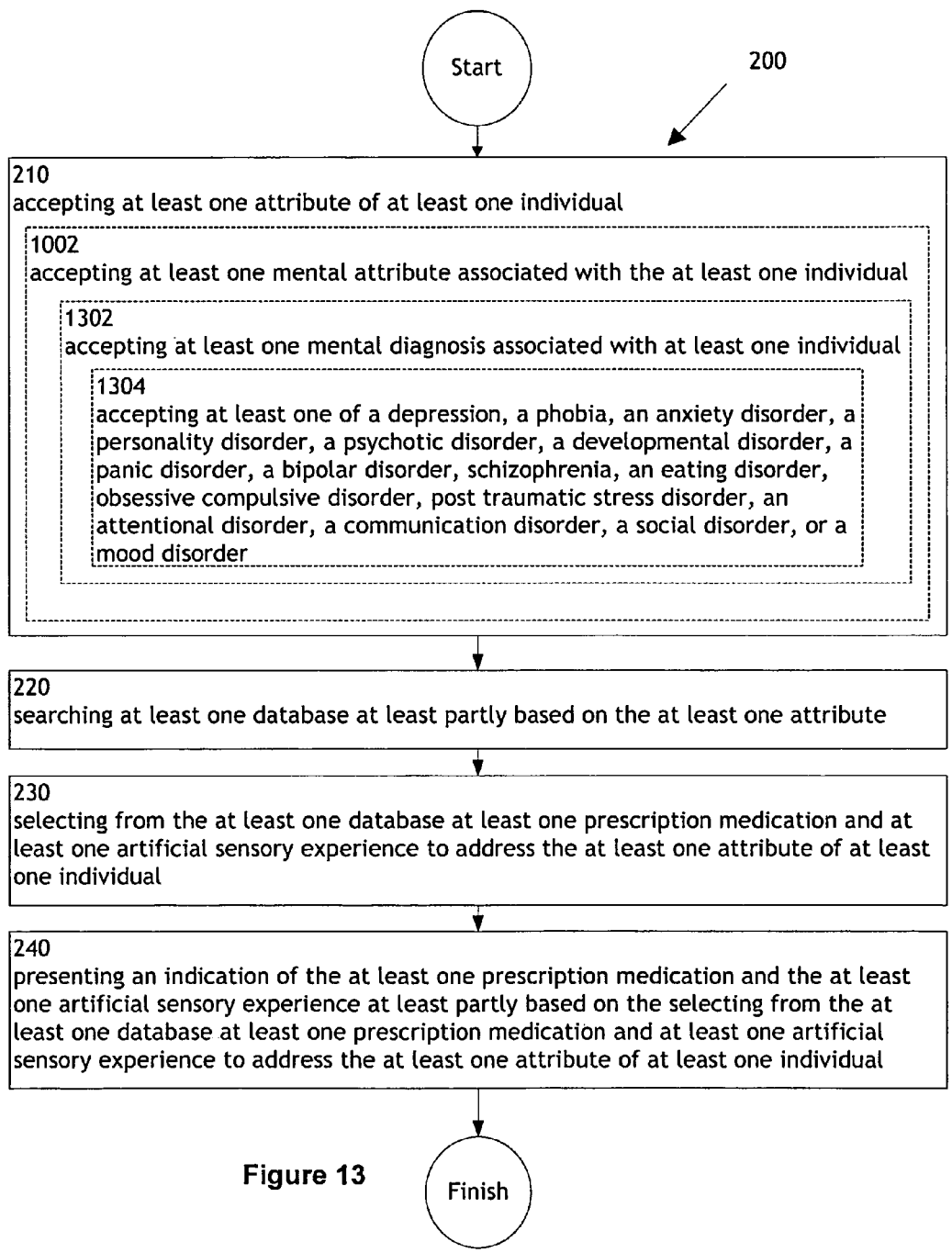
FIG. 13 illustrates an alternative embodiment of the operational flow of FIG. 2.

FIG. 13 illustrates alternative embodiments of the example operational flow 200 of FIG. 2. FIG. 13 illustrates example embodiments where operation 210 may include at least one additional operation. Additional operations may include an operation 1302, and/or an operation 1304. Further, operation 1302 illustrates accepting at least one mental diagnosis associated with at least one individual. For example, as shown in FIG. 1, acceptor module 102 may accept at least one mental diagnosis associated with at least one individual. In a specific instance, acceptor module 102 accepts from memory device 112 a mental diagnosis including a phobia associated with an anonymous individual or an individual named Roy Black. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, acceptor module 102 may include a computer processor.

Operation 1304 illustrates accepting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIG. 1, acceptor module 102 may accept at least one of a depression, a phobia, an anxiety disorder, a personality disorder, a psychotic disorder, a developmental disorder, a panic disorder, or a mood disorder. In one example, acceptor module 102 accepts from database entry 114 a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development. Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or bulimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, acceptor module 102 may include a computer processor.

Figure 14:
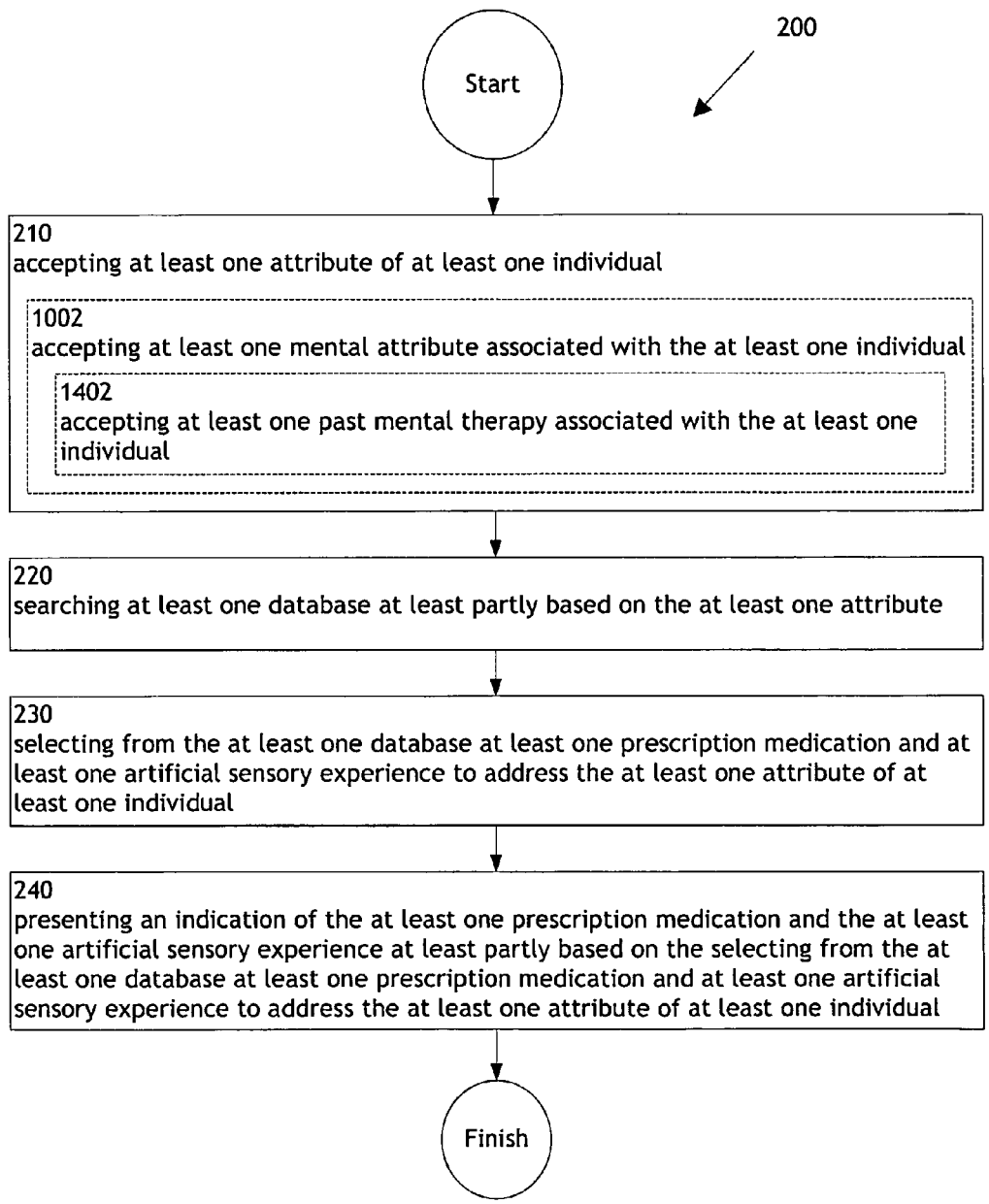
FIG. 14 illustrates an alternative embodiment of the operational flow of FIG. 2.

FIG. 14 illustrates alternative embodiments of the example operational flow 200 of FIG. 2. FIG. 14 illustrates example embodiments where operation 210 may include at least one additional operation. Additional operations may include an operation 1402. Further, operation 1402 illustrates accepting at least one past mental therapy associated with the at least one individual. For example, as shown in FIG. 1, acceptor module 102 may accept at least one past mental therapy associated with the at least one individual. In one instance, acceptor module 102 can accept from database entry 114 a past mental therapy associated with an individual named James Williams or an anonymous individual. A past mental therapy may include a list and/or a record of at least one mental therapy, such as an anti-depressant medication, administered to at least one individual. In some instances, acceptor module 102 may include a computer processor.

Figure 15:
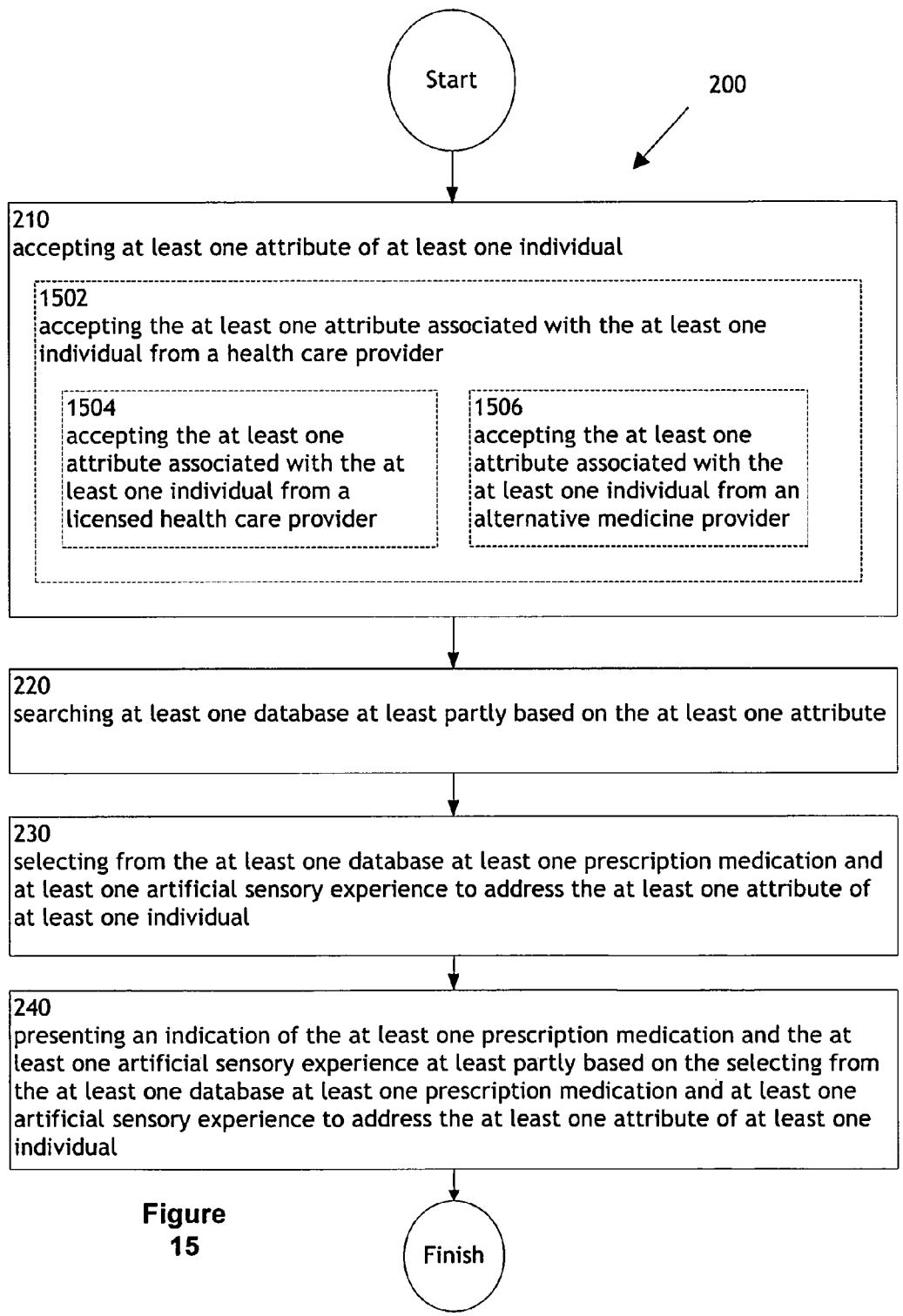
FIG. 15 illustrates an alternative embodiment of the operational flow of FIG. 2.

FIG. 15 illustrates alternative embodiments of the example operational flow 200 of FIG. 2. FIG. 15 illustrates example embodiments where operation 210 may include at least one additional operation. Additional operations may include an operation 1502, an operation 1504, and/or an operation 1506.

Operation 1502 illustrates accepting the at least one attribute associated with the at least one individual from a health care provider. For example, as shown in FIG. 1, acceptor module 102 may accept the at least one attribute associated with the at least one individual from a health care provider. In one example, acceptor module 102 can accept from user interface 116 and/or user 118 an attribute 120 including a medication history associated with a group of fifty individuals from a health care provider 136. A health care provider may include a hospital, a doctor, a nurse, a medical clinic, a dentist, and/or any provider of preventive, diagnostic, therapeutic, rehabilitative, maintenance, or palliative care and/or counseling. A healthcare provider may include a seller and/or dispenser of prescription drugs or medical devices. In some instances, acceptor module 102 may include a computer processor.

Operation 1504 illustrates accepting the at least one attribute associated with the at least one individual from a licensed health care provider. For example, as shown in FIG. 1, acceptor module 102 may accept the at least one attribute associated with the at least one individual from a licensed health care provider. In one instance, acceptor module 102 accepts from memory device 112 an attribute 120 including a symptom indication a phobia associated with an individual named Robert Clark from a licensed health care provider 136. A licensed health care provider may include a person licensed by a governing authority, such as a state, to provide medical and/or health care. Some examples of a licensed health care provider may include a licensed medical doctor or physician, a licensed physician's assistant, and/or a licensed nurse practitioner. In some instances, acceptor module 102 may include a computer processor.

Operation 1506 illustrates accepting the at least one attribute associated with the at least one individual from an alternative medicine provider. For example, as shown in FIG. 1, acceptor module 102 may accept the at least one attribute associated with the at least one individual from an alternative medicine provider. In one instance, acceptor module 102 can accept from network storage 110 an attribute 120 associated with an individual named Connie Martin from an alternative medicine provider. An alternative medicine provider may include a provider of folk medicine, herbal medicine, diet fads, homeopathy, faith healing, new age healing, chiropractic, acupuncture, aromatherapy, naturopathy, massage, reflexotogy, hypnotism, and/or music therapy. In some instances, acceptor module 102 may include a computer processor.

Figure 16:
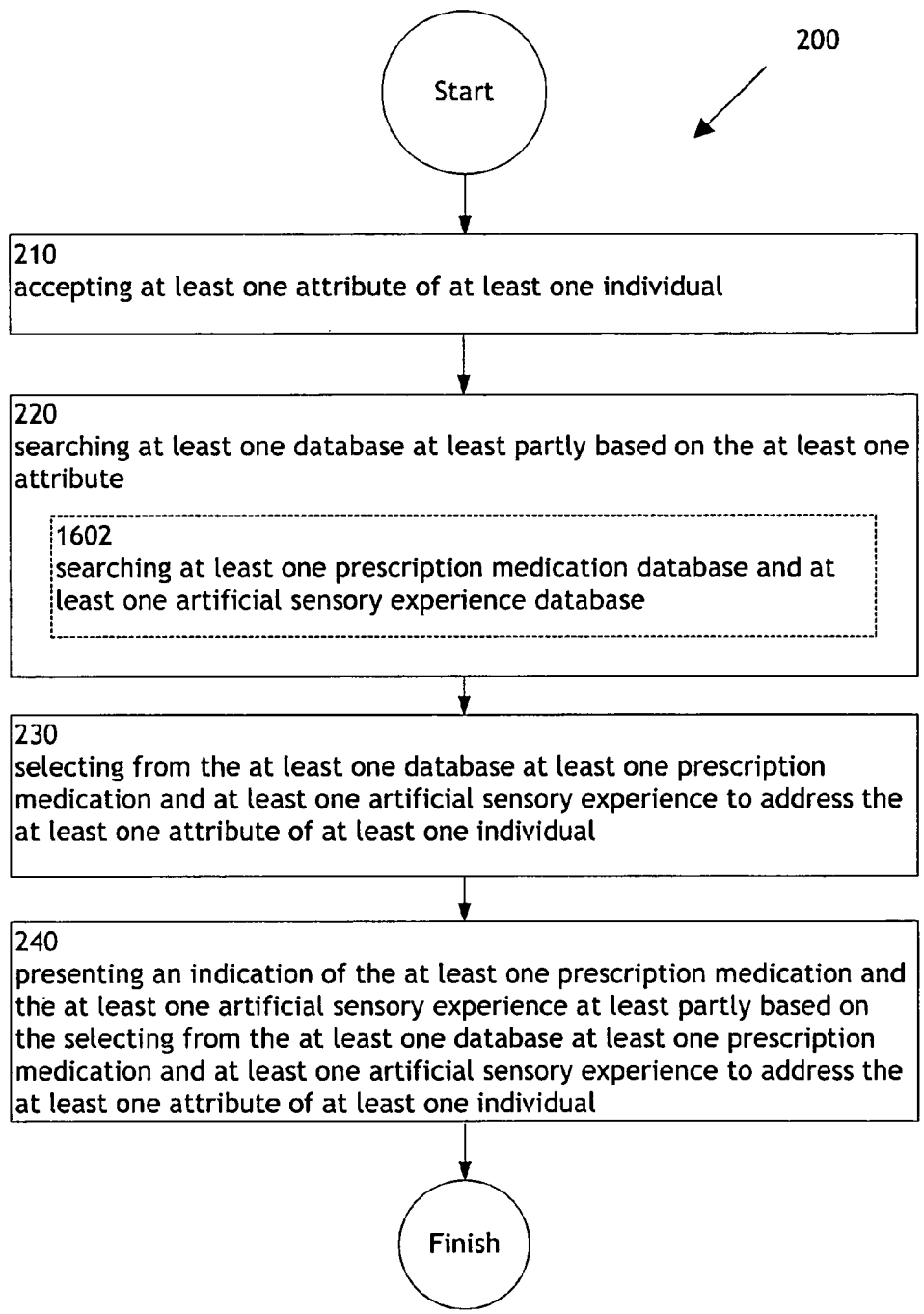
FIG. 16 illustrates an alternative embodiment of the operational flow of FIG. 2.

FIG. 16 illustrates alternative embodiments of the example operational flow 200 of FIG. 2. FIG. 16 illustrates example embodiments where operation 220 may include at least one additional operation. Additional operations may include an operation 1602.

Operation 1602 illustrates searching at least one prescription medication database and at least one artificial sensory experience database. For example, as shown in FIG. 1, querier module 104 may search at least one prescription medication database and at least one artificial sensory experience database. In one example, querier module 104 searches a medication database 124 and an artificial sensory experience database 126. A database may include a collection of data organized for convenient access. The database may include information digitally stored in a memory device 112, as at least a portion of at least one database entry 114, and/or in network storage 110. In some instances, the database may include information stored non-digitally such as at least a portion of a book, a paper file, and/or a non-computerized index and/or catalog. Non-computerized information may be received by acceptor module 102 by scanning or by manually entering the information into a digital format. A prescription database and/or medication database may include any database associated with at least one prescription medication and may be available to health care professionals and/or the public. An artificial sensory experience database may include any database associated with at least one artificial sensory experience and may include a database accessible by the public and/or a health care provider. In some instances, acceptor module 102 and/or querier module 104 may include one or more computer processors.

Figure 17:
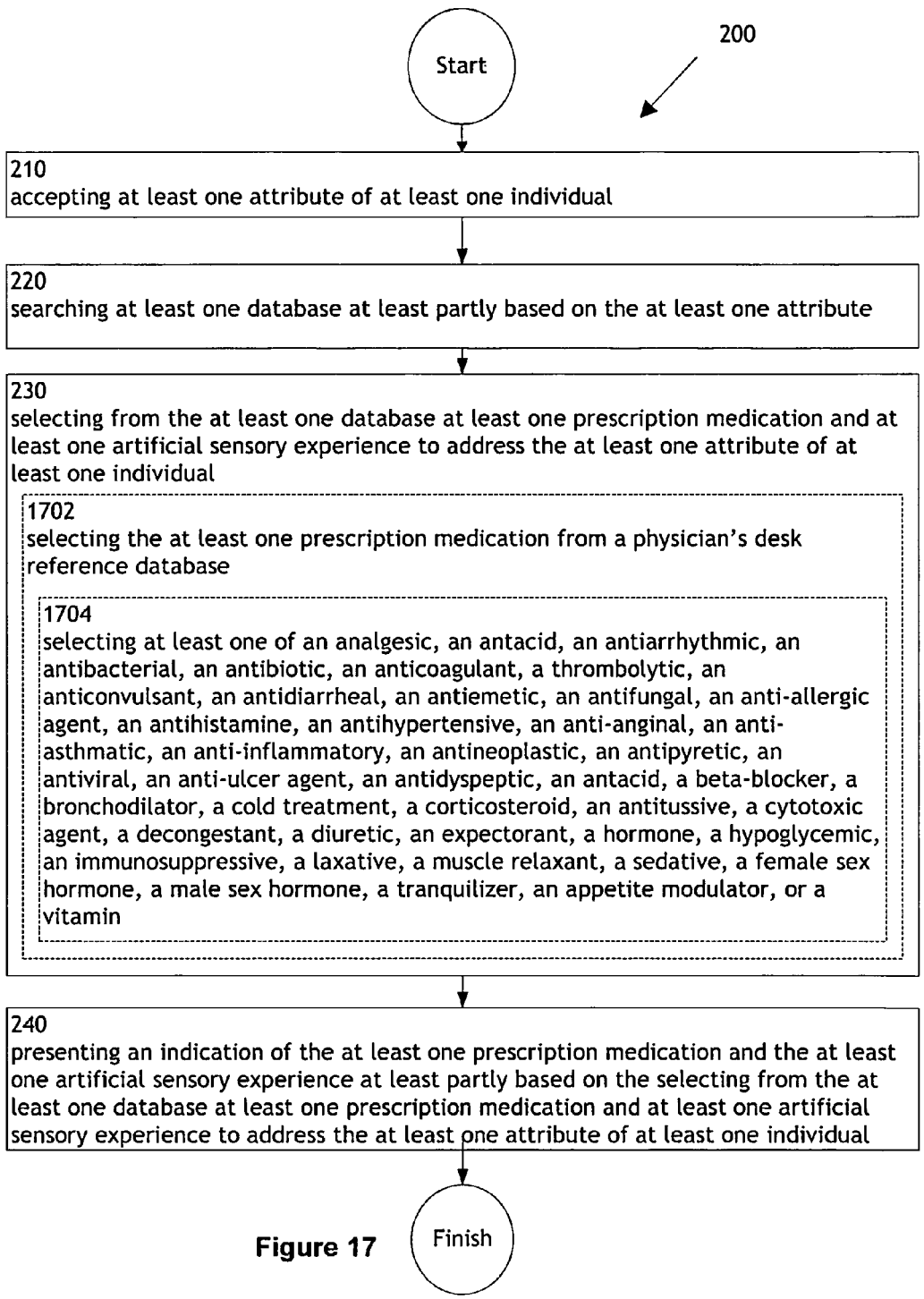
FIG. 17 illustrates an alternative embodiment of the operational flow of FIG. 2.

FIG. 17 illustrates alternative embodiments of the example operational flow 200 of FIG. 2. FIG. 17 illustrates example embodiments where operation 230 may include at least one additional operation. Additional operations may include an operation 1702, and/or an operation 1704.

Operation 1702 illustrates selecting the at least one prescription medication from a physician's desk reference database. For example, as shown in FIG. 1, selector module 106 may select the at least one prescription medication from a physician's desk reference database. In one example, selector module 106 selects the at least one prescription medication from a physician's desk reference database 122, such as a PDR psychiatry database. In some instances, selector module 106 may include a computer processor.

Operation 1704 illustrates selecting at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchoditator, a cold treatment, a corticosteroid, an antitussive, a cytotoxic agent, a decongestant, a diuretic, an expectorant, a hormone, a hypoglycemic, an immunosuppressive, a laxative, a muscle relaxant, a sedative, a female sex hormone, a male sex hormone, a tranquilizer, an appetite modulator, or a vitamin. For example, as shown in FIG. 1, selector module 106 may select at least one of an analgesic, an antacid, an antiarrhythmic, an antibacterial, an antibiotic, an anticoagulant, a thrombolytic, an anti- convulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, a cough suppressant, an antitussive, a cytotoxic agent, a decongestant, a diuretic, an expectorant, a hormone, a hypoglycemic, an immunosuppressive, a laxative, a muscle relaxant, a sedative, a female sex hormone, a mate sex hormone, a tranquilizer, an appetite modulator, or a vitamin. An analgesic may include a drug and/or other medication suitable for relieving pain. Additionally, an analgesic may be effective for relieving different degrees of pain. Some examples of an analgesic may include narcotics such as morphine or oxycodone, non-narcotics, an NSAID such as aspirin or naproxen or ibuprofen, and/or acetaminophen. An antacid may include a substance for neutralizing stomach acid, such as a proton pump inhibitor. Some examples of an antacid may include imeprazole and/or a pharmaceutical composition containing aluminum hydroxide, magnesium hydroxide, aluminum carbonate, calcium carbonate, sodium bicarbonate, hydrotalcite, bismuth subsalicylate, magaldrate, and/or simethicone.

An antiarrhythmic may include a drug for controlling a heartbeat irregularity. Some examples of an antiarrhythmic may include a beta blocker such as propanolol, and/or lidocaine, verapamil, and/or quinidine. An antibacterial may include a drug used to treat an infection. Some examples of an antibacterial may include amoxicillin and/or ciprofloxacin. An antibiotic may include a drug made from naturally occurring and/or synthetic substances for combating a bacterial infection. Some examples of an antibiotic may include penicillin, streptomycin, and/or sulfonamide-based drugs. An anticoagulant may include an agent for preventing blood clots. An example of an anticoagulant may include a vitamin K antagonist, such as warfarin, and/or aspirin. A thrombolytic may help dissolve and disperse a blood clot and may be prescribed for patients with recent arterial or venous thrombosis. A thrombolytic may be derived from *Streptomyces* spp. and/or recombinant DNA technology and may include streptokinase, urokinase, and/or a tissue plasminogen activator (TPA) such as alteplase.

An anticonvulsant may include a pharmaceutical administered for the prevention of seizures. Some examples of an anticonvulsant may include a barbiturate, a carbamate, a fatty acid derivative, and/or a sulfonamide. An antidiarrheal may include a drug utilized for the relief of diarrhea. Some examples of an antidiarrheal may include an antispasmodic such as diphenoxylate and loperamide, a bismuth compound, a bulking agent, and/or an absorbent. An antiemetic may include a drug used to treat nausea and vomiting. Some examples of an antiemetic may include a 5-HT3 receptor antagonist, a dopamine antagonist, and/or a histamine. An antifungal may include a drug used to treat fungal infections, the most common of which affect the hair, skin, nails, and/or mucous membranes. Some examples of antifungals may include polyene antifungals, imidazole and triazole antifungals, and/or allylamines. An anti-allergenic agent may include an agent characterized by preventing and/or reducing the effect of an allergen. Some examples of an anti-allergenic may include an antihistamine, cortisone, hydrocortisone, and/or epinephrine. An antihistamine may include an agent used for counteracting the effects of histamine. Some examples of an antihistamine may include a H1-receptor antagonist and/or a H2-receptor antagonist. An antihypertensive may include drugs utilized for lowering blood pressure.

Some examples of an antihypertensive may include a diuretic, an adrenergic receptor antagonist, and/or an ACE inhibitor. An anti-anginal may include an agent used for preventing and/or reducing angina and/or chest pain. Some examples of an anti-anginal may include aspirin, ranolazine, and/or ivabradine. An anti-asthmatic may include an agent for preventing and/or reducing asthma and/or its effects. Some examples of an anti-asthmatic may include albuterol, an inhaled steroid, for example budesonide or fluticasone, and/or ipratropium bromide.

An anti-inflammatory may include an agent utilized to reduce inflammation and/or to treat redness, heat, swelling, and/or increased blood flow associated for example, that seen with an infection or injury, or in many chronic diseases such as rheumatoid arthritis and gout. Some anti-inflammatories may include steroids, and/or NSAIDs such as naproxen, ibuprofen, and/or aspirin. An antineoplastic may include drugs used to treat cancer and to inhibit and/or prevent the development of tumors. Some antineoplastics may include alkylating agents, antimetabolites, enzymes, enzyme inhibitors, immune, modulators, and taxoids. An antipyretic may include a drug used to reduce a fever. Some examples of an antipyretic may include aspirin and/or acetaminophen. An antiviral may include a drug used to treat viral infections and/or to provide temporary protection against viral infections such as influenza. Some examples of an antiviral may include an interferon, acyclovir, ribavirin, and/or oseltamivir. An anti-ulcer agent may include an agent used for preventing and/or lessening the effect of an ulcer, including stomach ulcers, mouth ulcers, or other types of ulcers. Some examples of an anti-ulcer agent may include a bismuth compound, a prostaglandin analogue, and/or cimetidine. An antidyspeptic may include an agent used for treating and/or preventing dyspepsia. Some examples of an antidyspeptic may include simethicone and/or a proton pump inhibitor, such as esomeprazole. An antacid may include a substance, often a base, which may counteract stomach acidity. Some examples of an antacid may include magnesium hydroxide, aluminum hydroxide, calcium carbonate, and/or bismuth subsalicylate. A beta-blocker may include a beta-adrenergic blocking agent utilized for reducing the oxygen needs of the heart by reducing the heartbeat rate. Some examples of a beta-blocker may include propranolol, esmolol, bisoprolol, and/or timolol. A bronchodilator may include an agent utilized for opening the bronchial tubes within the lungs when the tubes have become narrowed, for example, by muscle spasm and may be used for treating asthma. Some examples of a bronchodilator may include albuterol and/or ipratropium bromide. A cold treatment may include an agent utilized for treating aches, pains, and/or fever accompanying a cold. Some cold treatments may include aspirin, acetaminophen, a decongestant, an antihistamine, and/or caffeine.

A corticosteroid may include a hormonal preparation used as an anti-inflammatory for arthritis or asthma and/or treating some malignancies or compensating for a deficiency of natural hormones. Some examples of a corticosteroid may include cortisol and/or aldosterone. A cough suppressant may include an agent used to soothe irritation caused by coughing and/or to prevent coughing. Some examples of a cough suppressant may include codeine, an antihistamine, and/or dextromethorphan. An antitussive may include a cough suppressant. A cytotoxic agent may include a drug used for killing and/or damaging cells. Some examples of a cytotoxic agent may include actinomycin-D, azathioprine, bleomycin, melphalan, busulphan, doxorubicin, etoposide, an antineoplastic agent, and/or an apoptotic agent. A decongestant may include an agent for reducing the swelling of the mucous membranes lining the nose and/or throat. Some examples of a decongestant may include pseudoephedrine and phenylephrine. A diuretic may include an agent for increasing the quantity of urine produced by the kidneys and passed out of the body. Some examples of a diuretic may include hydrochlorothiazide, spironolactone, mannitol, and/or glucose. An expectorant may include an agent for stimulating the flow of saliva, loosening and thinning mucus in airways, and/or promoting a more productive cough as to eliminate phlegm from the respiratory tract. An example of an expectorant may include guaifenesin. A hormone may include molecules produced naturally by the endocrine glands. Some examples of a hormone may include steroid hormones, amine-derived hormones, peptide hormones, and/or lipid and phospholipid-derived hormones. A hypoglycemic may include an agent for lowering the level of glucose in the blood. Some examples of a hypoglycemic may include a sulfonylurea, a meglitinide, a biguanide, a thiazolidinedione, and/or a alpha-glucosidase inhibitor. An immunosuppressive may include an agent for preventing or reducing the body's normal reaction to invasion by disease and/or foreign tissues. Some examples of an immunosuppressive may include a drug such as a corticosteroid, cyclosporine, rapamycin, which acts on immunophilins, and/or an antibody.

A laxative may include an agent for increasing the frequency and ease of bowel movements. Some examples of a laxative may include methylcellulose, docusate, mineral oil, and/or magnesium hydroxide. A muscle relaxant may include an agent utilized for relieving muscle spasms. Some examples of a muscle relaxant may include neuromuscular blocking drugs, carisoprodol, cyclobenzaprine, metaxalone, a benzodiazepine and/or a tranquilizer. A sedative may include a substance which depresses the central nervous system and may result in calmness, relaxation, reduction of anxiety, sleepiness, and/or slowed breathing. Some examples of a sedative may include zolpidem, and/or eszopiclone. A female sex hormone may include a hormone responsible for the development of female secondary sexual characteristics. Some examples of a female sex hormone may include estrogen and progesterone. A male sex hormone may include a hormone responsible for the development of secondary male sexual characteristics. One example of a male sex hormone may include testosterone. Sex hormone-related agents may include agents metabolically related to sex hormones. Examples of sex hormone-related agents may include sterols, androgens (testosterone), progestogens estrogens (estradiols, estrone), follicle-stimulating hormone, luteinizing hormone, inhibin B, anti-Mullerian hormone thyroid-related hormones. A tranquilizer may include any drug having a calming and/or sedative effect. Some examples of a tranquilizer may include an antidepressant, a barbiturate, and/or a benzodiazepine. An appetite modulator may include an agent used for regulating and/or adjusting appetite. Some examples of an appetite modulator may include recombinant PYY 3-36 and/or sibutramine. A vitamin may include chemicals essential in relatively small quantities for good health. Some examples of a vitamin may include Vitamin A, Vitamin C, Vitamin D, and/or Vitamin K.

In one instance, selector module 106 can select an analgesic and an antipsychotic for subsequent presentation, perhaps in response to accepting a pain symptom and a hallucination symptom as the at least one attribute. In some instances, selector module 106 may include a computer processor.

Figure 18:
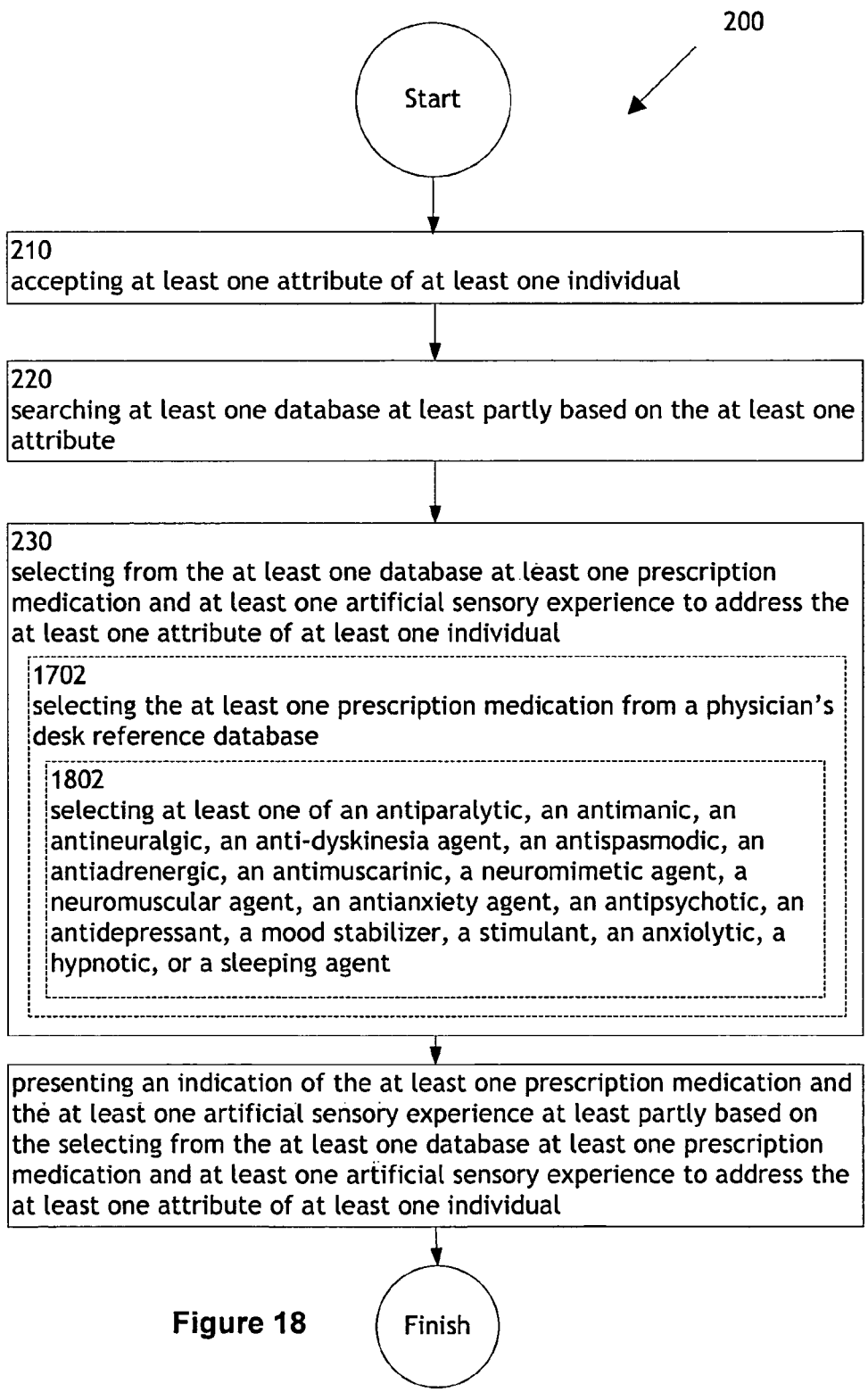
FIG. 18 illustrates an alternative embodiment of the operational flow of FIG. 2.

FIG. 18 illustrates alternative embodiments of the example operational flow 200 of FIG. 2. FIG. 18 illustrates example embodiments where operation 230 may include at least one additional operation. Additional operations may include an operation 1802. Further, operation 1802 illustrates selecting at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety agent, an antipsychotic, an antidepressant, a mood stabilizer, a stimulant, an anxiolytic, a hypnotic, or a sleeping agent. For example, as shown in FIG. 1, selector module 106 may select at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety drug, an antipsychotic, an antidepressant, a mood stabilizer, a stimulant, an anxiolytic, a hypnotic, and/or a sleeping agent such as a long-acting barbiturate. In one example, selector module 106 selects an antianxiety drug and a steeping agent. An antiparalytic may include an agent used for preventing the loss of and/or recovering muscle function. One example of an antiparalytic may include methylprednisolone. An antimanic may include an agent used for treating and/or suppressing mania. Some examples may include lamotrigine and/or carbamazepine. An antineuralgic may include an agent for relieving paroxysmal nerve pain. One example of an antineuralgic may include carbamazepine. An anti-dyskinesia agent may include an agent used for reducing and/or preventing dyskinesia, including involuntary muscle movement. One example of an anti-dyskinesia agent may include methylenedioxymethamphetamine. An antispasmodic may include a drug or an herb that suppresses smooth muscle contraction. Some examples of an antispasmodic may include dicyclomine and/or hyoscyamine. An antiadrenergic may include a medication for inhibiting the functioning of the sympathetic nervous system. Some examples of an antiadrenergic may include clonidine and/or mecamylamine. An antimuscarinic may include an agent for reducing the activity of the muscarinic acetylcholine receptor. Some examples of an antimuscarinic may include atropine and/or hyoscine. A neuromimetic agent may include an agent that mimics the response of an effector organ to nerve impulses. A neuromuscular agent may block neuromuscular transmission at the neuromuscular junction and cause paralysis of the affected skeletal muscles. Some examples of a neuromuscular agent may include atracurium and/or vecuronium. An antianxiety drug may include a drug for suppressing anxiety and relaxing the muscles. An antianxiety drug may include a sedative, a tranquilizer, an anxiolytic, such as a benzodiazepine, alprazolam and/or diazepam, an antidepressant, a short-acting barbiturate, and/or an herbal treatment, such as chamomile, kava extract, Kratom, and/or valerian. An antipsychotic may include a group of drugs commonly used to treat psychosis and may include phenothiazines, thioxanthenes, butyrophenones, risperidone, amisulpride, and/or other suitable drugs. An antidepressant may include a psychiatric medication or other substance, such as a nutrient or herb, used for alleviating depression or dysthymia. Some examples of an antidepressant may include a selective serotonin reuptake inhibitor, such as Prozac and/or Zoloft, and/or a serotonin-norepinephrine reuptake inhibitor, such as Cymbalta. A mood stabilizer may include a psychiatric medication used to treat mood disorders characterized by intense and sustained mood shifts. Some examples of a mood stabilizer may include lithium carbonate and/or lamotrigine. A stimulant may include substances that may temporarily increase alertness and awareness, such as caffeine, ephedrine, and/or nicotine. An anxiolytic may include a substance used for the treatment of anxiety, such as a benzodiazepine and/or a barbiturate. A hypnotic may include substances that induce sleep, such as a barbiturate and/or an antihistamine (diphenhydramine). A sleeping agent may include any number of medications for helping a person sleep and/or stay asleep and may include benzodiazepines, antidepressants, melatonin, and/or antihistamines as well as other suitable substances. In some instances, selector module 106 may include a computer processor.

Figure 19:
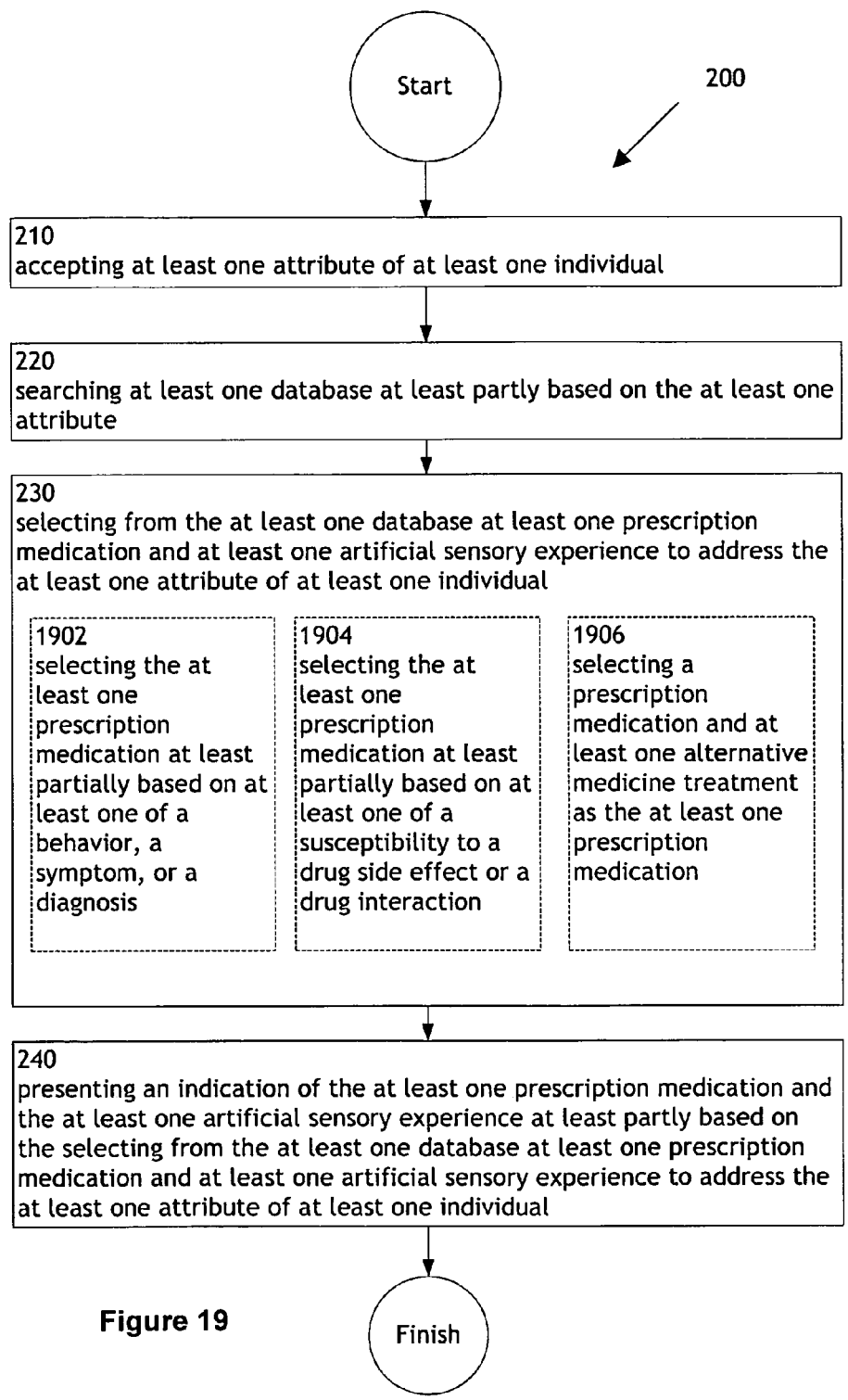
FIG. 19 illustrates an alternative embodiment of the operational flow of FIG. 2.

FIG. 19 illustrates alternative embodiments of the example operational flow 200 of FIG. 2. FIG. 19 illustrates example embodiments where operation 230 may include at least one additional operation. Additional operations may include an operation 1902, an operation 1904, and/or an operation 1906.

Operation 1902 illustrates selecting the at least one prescription medication at least partially based on at least one of a behavior, a symptom, or a diagnosis. For example, as shown in FIG. 1, selector module 106 may select the at least one prescription medication at least partially based on at least one of a behavior, a symptom, or a diagnosis. In one instance, selector module 106 can select a prescription medication based on a diagnosis. A behavior may include the manner a person behaves toward other people and/or a certain circumstance. A symptom may include a subjective indicator of a health problem reported by an individual, or a sign of a health problem noticed by another, perhaps a doctor. A symptom may be evidence of a disease, a disability, an impairment, and/or a condition. A diagnosis may include an identification of a disease, a disability, an impairment, and/or a condition. In some instances, selector module 106 may include a computer processor.

Operation 1904 illustrates selecting the at least one prescription medication at least partially based on at least one of a susceptibility to a drug side effect or a drug interaction. For example, as shown in FIG. 1, selector module 106 may select the at least one prescription medication at least partially based on at least one of a susceptibility to a drug side effect or a drug interaction. In one instance, selector module 106 can select a prescription medication based on a susceptibility to a drug side effect including an allergy. A susceptibility to a drug side effect may include a probability a certain person may be vulnerable to a side effect associated with a specific drug and/or medication. A susceptibility to a drug side effect may include predisposition to a particular drug side effect or class of drug side effects, such as upset stomach associated with aspirin formulations. A drug reaction may include a possible response a person may exhibit resulting from at least one drug and/or medication administered to the person. A drug reaction may include an allergy and/or a drug and/or medication interaction with a separate drug and/or medication. In some instances, selector module 106 may include a computer processor.

Operation 1906 illustrates selecting a prescription medication and at least one alternative medicine treatment as the at least one prescription medication. For example, as shown in FIG. 1, selector module 106 may select a prescription medication and at least one alternative medicine treatment as the at least one prescription medication. In one instance, selector module 106 can select a prescription medication and at least one alternative medicine treatment as the at least one prescription medication. A prescription medication may include a medication, drug, and/or treatment available only with written instructions from a doctor, dentist, and/or other licensed professional. An alternative medicine treatment may include medical and/or nutraceutical treatments and/or practices utilized instead of standard medical treatments. Some examples of alternative medicine treatments may include chiropractic, herbal medicine, acupuncture, homeopathy, naturopathy, and/or spiritual devotions. In some instances, selector module 106 may include a computer processor.

Figure 20:
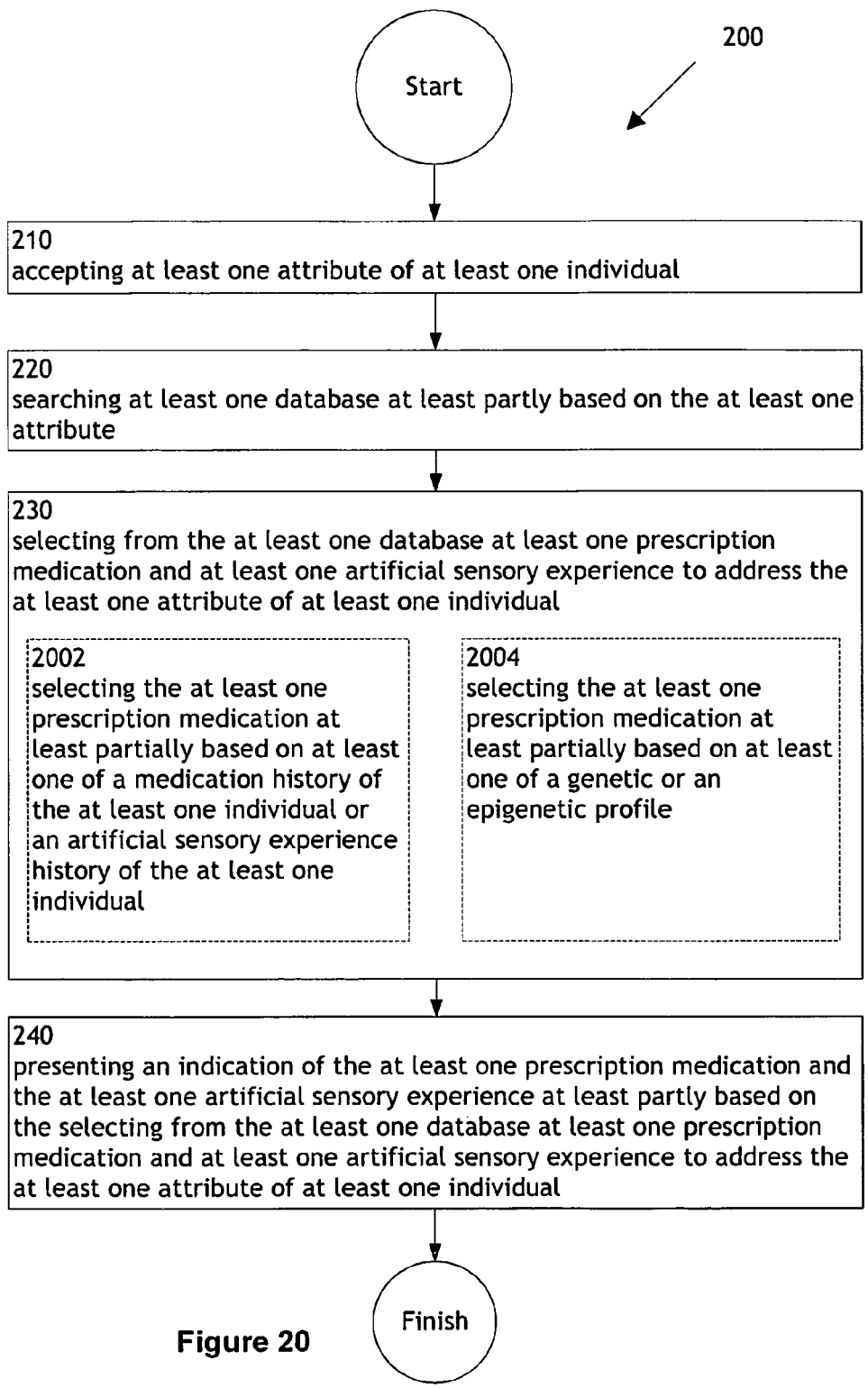
FIG. 20 illustrates an alternative embodiment of the operational flow of FIG. 2.

FIG. 20 illustrates alternative embodiments of the example operational flow 200 of FIG. 2. FIG. 20 illustrates example embodiments where operation 230 may include at least one additional operation. Additional operations may include an operation 2002, and/or an operation 2004.

Operation 2002 illustrates selecting the at least one prescription medication at least partially based on at least one of a medication history of the at least one individual or an artificial sensory experience history of the at least one individual. For example, as shown in FIG. 1, selector module 106 may select the at least one prescription medication at least partially based on at least one of a medication history of the at least one individual or an artificial sensory experience history of the at least one individual. In one example, selector module 106 can select a prescription medication based on a medication history of an individual named Jennifer Harris or an anonymous individual. A medication history may include any record of administered medications and/or drugs that may exist for an individual. An artificial sensory experience history may include any record of an artificial sensory experience associated with an individual. In some instances, selector module 106 may include a computer processor.

Operation 2004 illustrates selecting the at least one prescription medication at least partially based on at least one of a genetic or an epigenetic profile. For example, as shown in FIG. 1, selector module 106 may select the at least one prescription medication at least partially based on at least one of a genetic or an epigenetic profile. In one instance, selector module 106 can select a prescription medication based on a genetic profile. A genetic profile may include hereditary information encoded in the genetic sequence of an individual. An epigenetic profile may include information regarding chromatin and/or DNA modifications that are stable over rounds of cell division but do not involve changes in the underlying DNA sequence of the organism, such as histone acetylation and/or DNA methylation. Other epigenetic information may be found in higher-order chromatin structure. In some instances, selector module 106 may include a computer processor.

Figure 21:
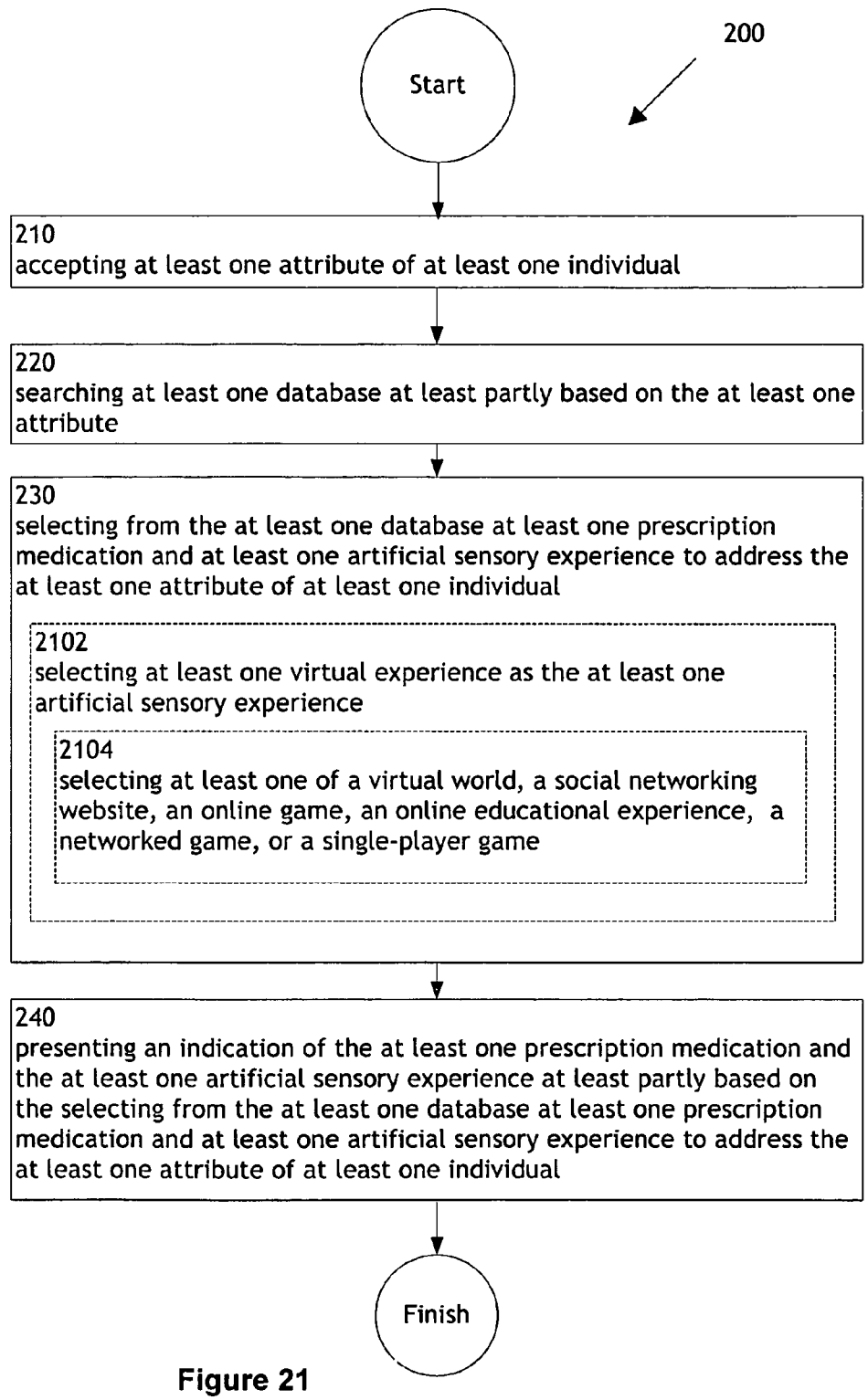
FIG. 21 illustrates an alternative embodiment of the operational flow of FIG. 2.

FIG. 21 illustrates alternative embodiments of the example operational flow 200 of FIG. 2. FIG. 21 illustrates example embodiments where operation 230 may include at least one additional operation. Additional operations may include an operation 2102, and/or an operation 2104.

Operation 2102 illustrates selecting at least one virtual experience as the at least one artificial sensory experience. For example, as shown in FIG. 1, selector module 106 may select at least one virtual experience as the at least one artificial sensory experience. In one example, selector module 106 can select a virtual experience as the artificial sensory experience. A virtual experience may include an experience with a computer-simulated environment. Such a virtual experience may be interactive or non-interactive. Some examples of a virtual experience may include an experience with a virtual world, a simulated reality, a computer game, and/or a virtual tour, and may involve input devices such as a keyboard, a mouse, an accelerometer-containing input device, and/or a wired glove. A virtual experience may also involve a visual and/or auditory monitoring device such as a video monitor, goggles, loudspeakers, or the like. Examples of a virtual experience include second life, snow world, or the like. In some instances, selector module 106 may include a computer processor.

Operation 2104 illustrates selecting at least one of a virtual world, a social networking website, an online game, an online educational experience, a networked game, or a single-player game. For example, as shown in FIG. 1, selector module 106 may select at least one of a virtual world, a social networking website, an online game, an online educational experience, a networked game, or a single-player game. In one instance, selector module 106 can select a virtual world. A virtual world may include a computer-based simulated environment intended for its users to inhabit and interact via avatars, such as second life. A social networking website may include a website for observing and/or interacting with one or more personal and/or professional relationships between individuals. Some examples of a social networking website may include MySpace, GeoCities, Facebook, and/or LinkedIn. In one instance, selector module 106 may select Facebook as the social networking website and may include directions to Facebook to implement a color scheme including bright colors, such as yellow and light blue, for preventing the onset of depression in a depression prone viewer. An online game may include a game played over a network, such as hardwired terminals, a wireless network, a modem network, a video console, and/or the internet. Some online games may include virtual worlds and/or virtual communities. Examples of online games may include World of Warcraft (WoW), Final Fantasy XI, Lineage II, Guild Wars, and/or RuneScape. An online educational experience may include a tutorial, a lesson, and/or an online class. Some examples of an online educational experience may include a HTML tutorial, an online piano lesson, and/or an online degree program from the University of Phoenix. A networked game may include any game played by more than one player and may be played on a computer. An example of a networked game may include World of Warcraft (WoW). A single-player game may include any game that can be played by one player and that may or may not be played on a computer. Examples of a single-player game includes solitaire, puzzle games such as Tetris, Call of Duty, and Guitar Hero. In some instances, selector module 106 may include a computer processor.

Figure 22:
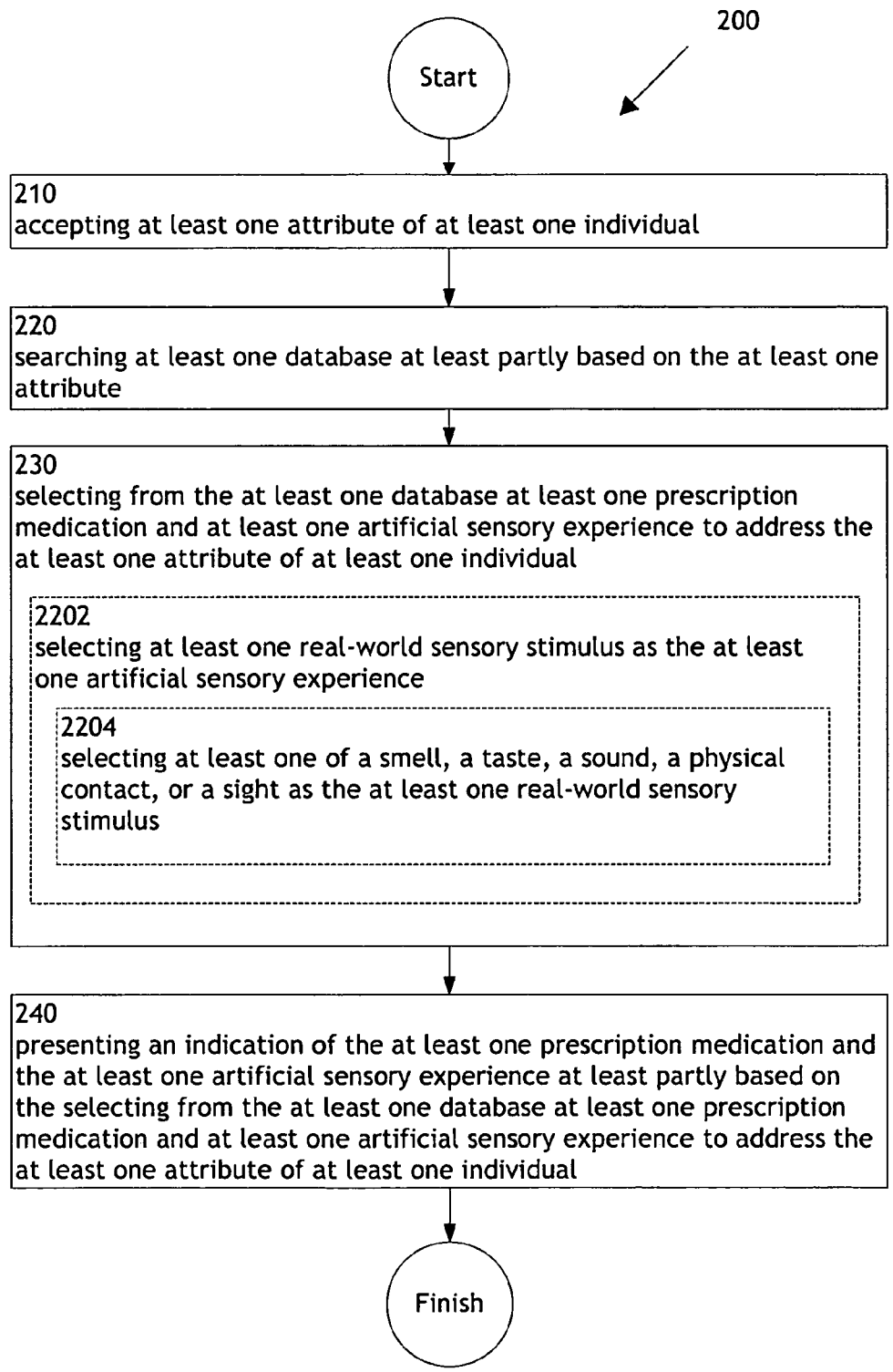
FIG. 22 illustrates an alternative embodiment of the operational flow of FIG. 2.

FIG. 22 illustrates alternative embodiments of the example operational flow 200 of FIG. 2. FIG. 22 illustrates example embodiments where operation 230 may include at least one additional operation. Additional operations may include an operation 2202, and/or an operation 2204.

Operation 2202 illustrates selecting at least one real-world sensory stimulus as the at least one artificial sensory experience. For example, as shown in FIG. 1, selector module 106 may select at least one real-world sensory stimulus as the at least one artificial sensory experience. In one instance, selector module 106 can select a real-world sensory stimulus including an aroma as an artificial sensory experience. Some examples of a real-world sensory stimulus may include aromas and/or smells, sounds, sights, touch, pressure, temperature and/or heat, and/or vibration. In some instances, selector module 106 may include a computer processor. Further, operation 2204 illustrates selecting at least one of a smell, a taste, a sound, a physical contact, or a sight as the at least one real-world sensory stimulus. For example, as shown in FIG. 1, selector module 106 may select at least one of a smell, a taste, a sound, a physical contact, or a sight as the at least one real-world sensory stimulus. In one example, selector module 106 selects a smell and a taste as a real-world sensory stimulus. A smell may include any property detected by the nose and/or olfactory system. A taste may include any flavor and/or property detected by the tongue and/or taste buds. A sound may include any sound wave that may be detected by the eardrum. A physical contact may include anything related to touch, feel, and/or detection by the skin and/or body, and/or physical activity including exercise. In one instance, selector module 106 may select a physical contact including physical exercise associated with participating in playing a tennis game on a Nintendo Wii video game console, for example. A sight may include any image, and/or light detected by the eyes. In some instances, selector module 106 may include a computer processor.

Figure 23:
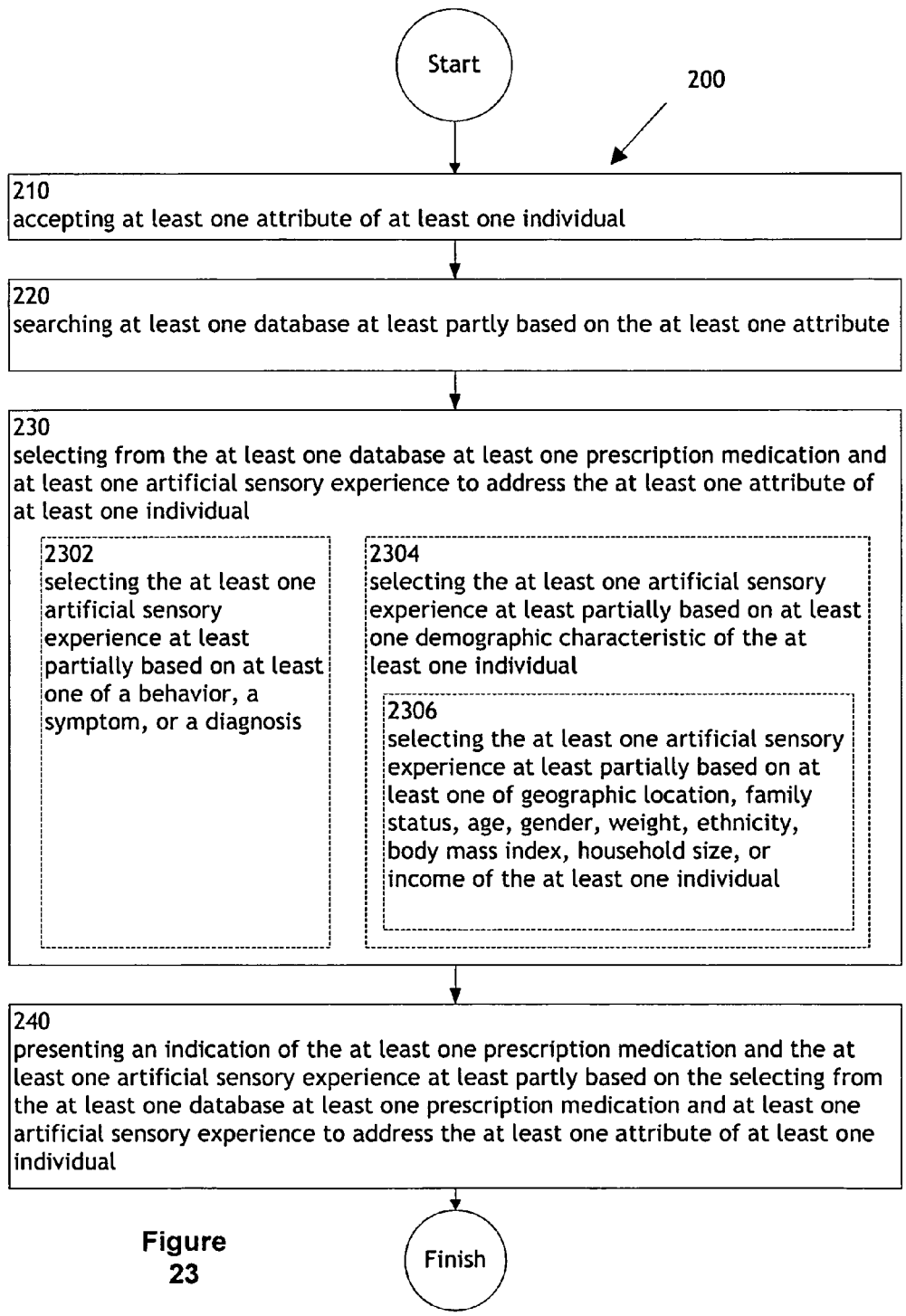
FIG. 23 illustrates an alternative embodiment of the operational flow of FIG. 2.

FIG. 23 illustrates alternative embodiments of the example operational flow 200 of FIG. 2. FIG. 23 illustrates example embodiments where operation 230 may include at least one additional operation. Additional operations may include an operation 2302, an operation 2304, and/or an operation 2306.

Operation 2302 illustrates selecting the at least one artificial sensory experience at least partially based on at least one of a behavior, a symptom, or a diagnosis. For example, as shown in FIG. 1, selector module 106 may select the at least one artificial sensory experience at least partially based on at least one of a behavior, a symptom, or a diagnosis. In one example, selector module 106 can select an artificial sensory experience based on behavior entered by a user 118 via a user interface 116. A behavior may include the manner in which a person and/or thing acts and/or reacts. A symptom may include a manifestation, sign, and/or an indication of the presence of a disease and/or some other disorder and/or abnormality. A diagnosis may include identifying a disease and/or condition by its signs and/or symptoms. For example, selector module 106 and/or system 100 may select an immersive virtual reality experience as the at least one artificial sensory experience at least partially based on a pain symptom and/or a third-degree burn diagnosis. In some instances, selector module 106 may include a computer processor.

Operation 2304 illustrates selecting the at least one artificial sensory experience at least partially based on at least one demographic characteristic of the at least one individual. For example, as shown in FIG. 1, selector module 106 may select the at least one artificial sensory experience at least partially based on at least one demographic characteristic of the at least one individual. In one example, selector module 106 can select an artificial sensory experience based on a demographic characteristic the at least one individual. A demographic characteristic may include a socioeconomic, age, gender, and/or other similar factor defining a certain population. For example, selector module 106 and/or system 100 may select a virtual reality experience such as a Sesame Street or Disney-themed experience as the at least one artificial sensory experience at least partially based on an indication that the individual is aged 6-10 years old. In some instances, selector module 106 may include a computer processor.

Further, operation 2306 illustrates selecting the at least one artificial sensory experience at least partially based on at least one of geographic location, family status, age, gender, weight, ethnicity, body mass index, household size, or income of the at least one individual. For example, as shown in FIG. 1, selector module 106 may select the at least one artificial sensory experience at least partially based on at least one of geographic location, family status, age, gender, weight, ethnicity, body mass index, household size, or income of the at least one individual. In one example, selector module 106 can select the artificial sensory experience based on an age and a weight associated with the at least one individual. A geographic location may include a location where an individual currently resides, has resided in the past, and/or has visited. A family status may include marital status, status and/or presence of children, and/or the status and/or health of extended family. In some instances, selector module 106 may include a computer processor.

Figure 24:
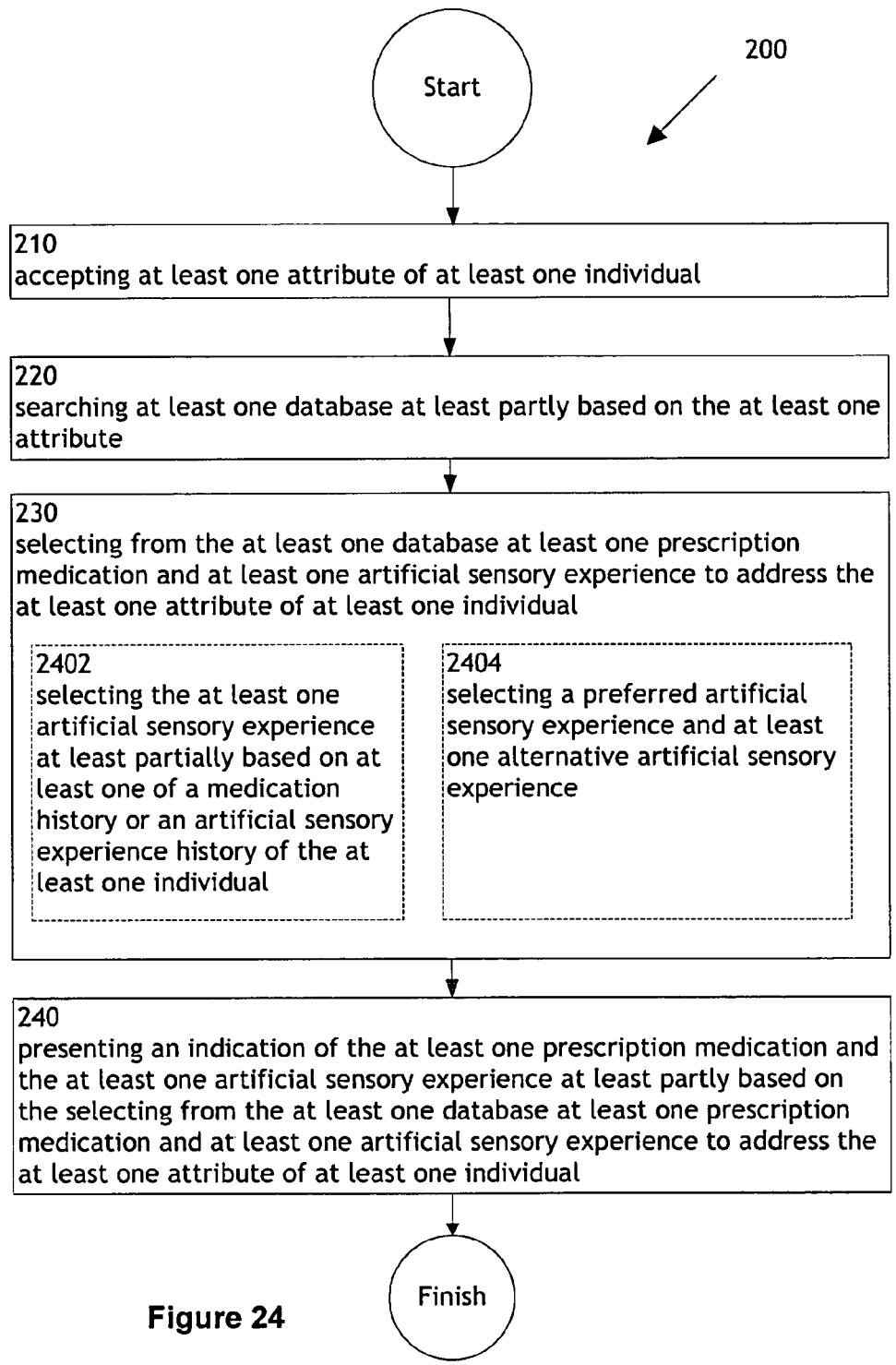
FIG. 24 illustrates an alternative embodiment of the operational flow of FIG. 2.

FIG. 24 illustrates alternative embodiments of the example operational flow 200 of FIG. 2. FIG. 24 illustrates example embodiments where operation 230 may include at least one additional operation. Additional operations may include an operation 2402, and/or an operation 2404.

Operation 2402 illustrates selecting the at least one artificial sensory experience at least partially based on at least one of a medication history or an artificial sensory experience history of the at least one individual. For example, as shown in FIG. 1, selector module 106 may select the at least one artificial sensory experience at least partially based on at least one of a medication history or an artificial sensory experience history of the at least one individual. In one instance, selector module 106 can select an artificial sensory experience based on an artificial sensory experience history of the at least one individual. An artificial sensory experience history may include any record of at least one administered artificial sensory experience history. For example, system 100 and/or selector module 106 may select a modified facebook webpage having a cheerful color scheme at least partly based on a facebook usage history for an individual with signs of depression. In some instances, selector module 106 may include a computer processor.

Operation 2404 illustrates selecting a preferred artificial sensory experience and at least one alternative artificial sensory experience. For example, as shown in FIG. 1, selector module 106 may select a preferred artificial sensory experience and at least one alternative artificial sensory experience. In one example, selector module 106 can select a preferred artificial sensory experience and at least one alternative artificial sensory experience. A preferred artificial sensory experience may include a more desirable artificial sensory experience due to a lack of and/or a reduced level of side effects, reduced impact upon the individual, and/or increased compatibility with another medications and/or treatment. An alternative artificial sensory experience may include any artificial sensory experience in addition to the preferred artificial sensory experience and may be less desirable than the preferred artificial sensory experience due to side effects and/or increased impact upon the individual. In some instances, selector module 106 may include a computer processor.

Figure 25:
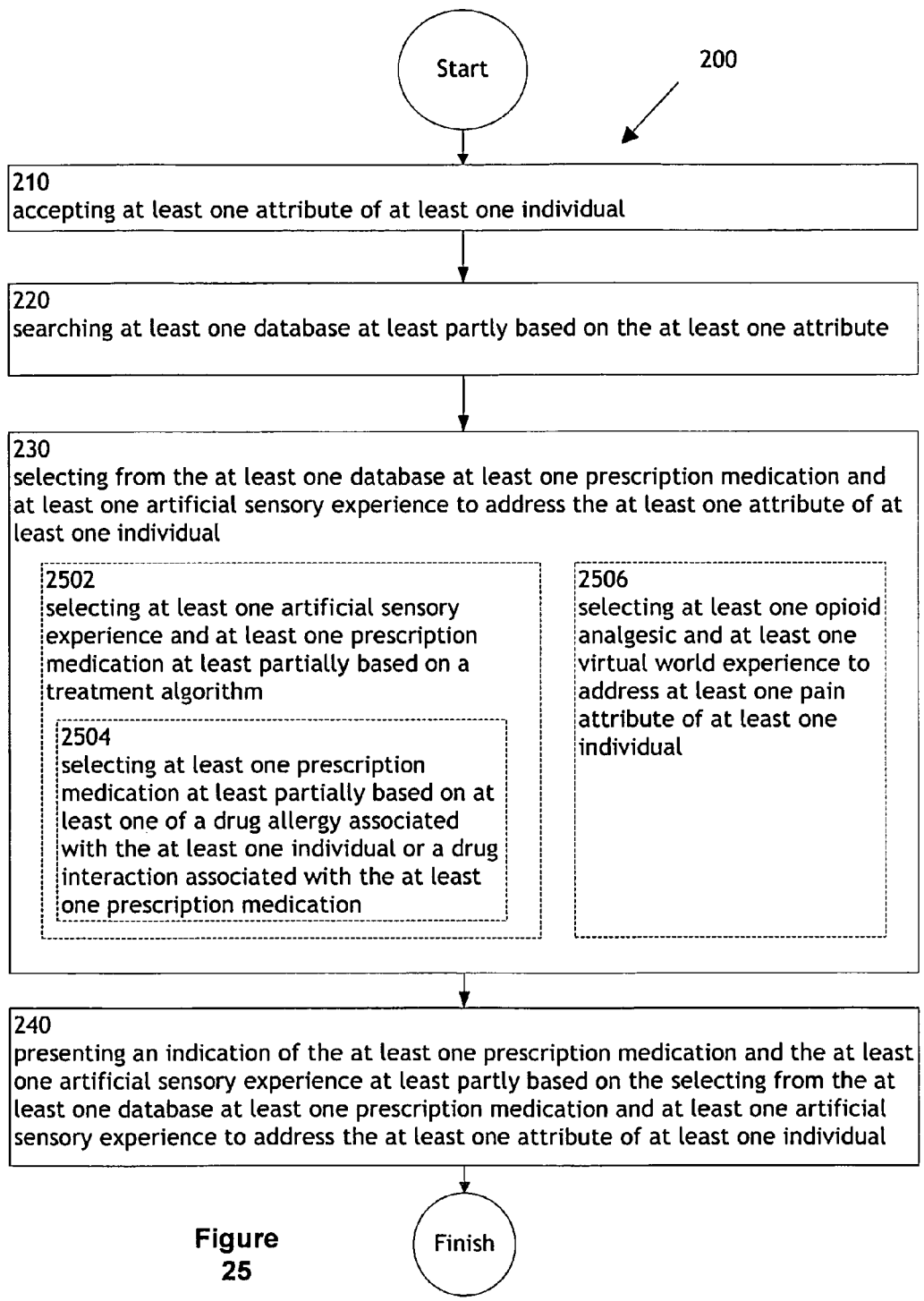
FIG. 25 illustrates an alternative embodiment of the operational flow of FIG. 2.

FIG. 25 illustrates alternative embodiments of the example operational flow 200 of FIG. 2. FIG. 25 illustrates example embodiments where operation 230 may include at least one additional operation. Additional operations may include an operation 2502, an operation 2504, and/or an operation 2506.

Operation 2502 illustrates selecting at least one artificial sensory experience and at least one prescription medication at least partially based on a treatment algorithm. For example, as shown in FIG. 1, selector module 106 may select at least one artificial sensory experience and at least one prescription medication at least partially based on a treatment algorithm. In one instance, selector module 106 can select an artificial sensory experience and a prescription medication based on a computer software treatment algorithm. A treatment algorithm may include any computation, formula, statistical survey, and/or look-up table for determining and/or selecting a suitable artificial sensory experience and prescription medication combination. Some examples may include a computer software algorithm, a calculator, a flowchart, and/or a decision tree. For example, system 100 and/or selector module 106 may, based on an accepted pain symptom of an individual, access a lookup chart that matches the pain symptom with a pain medication, such as naproxen, and a virtual experience, such as World of Warcraft. Such a combination therapy may be particularly effective in ameliorating the pain symptom in the individual. In some instances, selector module 106 may include a computer processor.

Further, operation 2504 illustrates selecting at least one prescription medication at least partially based on at least one of a drug allergy associated with the at least one individual or a drug interaction associated with the at least one prescription medication. For example, as shown in FIG. 1, selector module 106 may select at least one prescription medication at least partially based on at least one of a drug allergy associated with the at least one individual or a drug interaction associated with the at least one prescription medication. In one example, selector module 106 can select a prescription medication based on a drug allergy associated with the at least one individual. A drug allergy may include any allergy to a drug and/or drug intolerance. Some examples of a drug allergy may include penicillin allergies, codeine allergies, and/or allergies to a dye in a drug. A drug interaction may include an undesirable and/or unwanted reaction between two or more drugs and/or medications. For example, the system 100 and/or selector module 106 can select a prescription medication other than those that might cause a side effect in an individual, perhaps because of a known predisposition to the side effect (e.g., an allergy) or because of a known drug-drug interaction relevant to the individual based on the individual's medication regimen. In this way, risk of side effects can be lessened. In some instances, selector module 106 may include a computer processor.

Operation 2506 illustrates selecting at least one opioid analgesic and at least one virtual world experience to address at least one pain attribute of at least one individual. For example, as shown in FIG. 1, selector module 106 may select from a prescription medication database at least one opioid analgesic and at least one virtual world experience to address at least one pain attribute of at least one individual. In one example, selector module 106 can select an opioid analgesic including morphine and a virtual world experience including an online game to address a pain attribute of at least one individual named Mary Andersen. In some instances, selector module 106 may include a computer processor.

Figure 26:
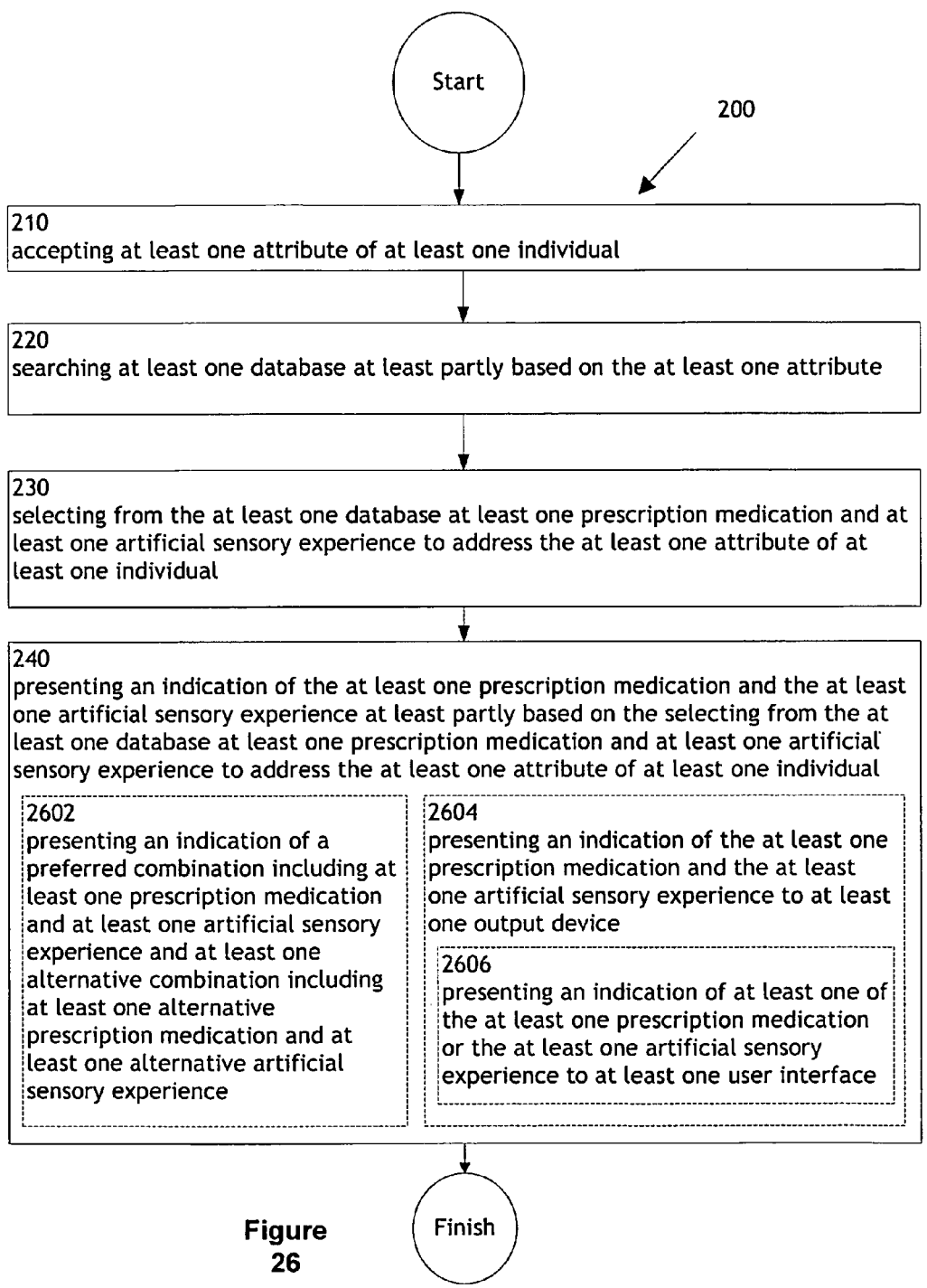
FIG. 26 illustrates an alternative embodiment of the operational flow of FIG. 2.

FIG. 26 illustrates alternative embodiments of the example operational flow 200 of FIG. 2. FIG. 26 illustrates example embodiments where operation 240 may include at least one additional operation. Additional operations may include an operation 2602, an operation 2604, and/or an operation 2606.

Operation 2602 illustrates presenting an indication of a preferred combination including at least one prescription medication and at least one artificial sensory experience and at least one alternative combination including at least one alternative prescription medication and at least one alternative artificial sensory experience. For example, as shown in FIG. 1, presenter module 108 may present an indication of a preferred combination including at least one prescription medication and at least one artificial sensory experience and at least one alternative combination including at least one alternative prescription medication and at least one alternative artificial sensory experience. In one instance, presenter module 108 can present an indication of a preferred combination to an individual 134 including a prescription medication and an artificial sensory experience along with an alternative combination including an alternative prescription medication and an alternative artificial sensory experience. Individual 134 may include a single individual, multiple individuals, and/or an entity. A preferred combination may include a more desirable combination due to a lack of and/or a reduced number of and/or level of side effects, reduced impact upon the administered individual, and/or increased compatibility with another medications and/or treatment. An alternative combination may include any combination in addition to the preferred combination and may be ostensibly less desirable than the preferred artificial sensory experience because of a potential side effect and/or impact upon the administered individual. Presentation of alternative combinations may provide benefits to the individual in terms of accessibility, affordability, and/or personal preference of medication and/or artificial sensory experience. In some instances, presenter module 108 may include a computer processor.

Operation 2604 illustrates presenting an indication of the at least one prescription medication and the at least one artificial sensory experience to at least one output device. For example, as shown in FIG. 1, presenter module 108 may present an indication of the at least one prescription medication and the at least one artificial sensory experience to at least one output device. In one example, presenter module 108 can present an indication of a prescription medication and an artificial sensory experience to an output device 130 including a printer at a health clinic. An output device may include any hardware device configured for receiving computer output. Some examples of an output device may include a printer, a monitor, a mobile phone, a speaker, and/or a visual display unit. The output device may be used by individual 134. In some instances, presenter module 108 may include a computer processor.

Further, operation 2606 illustrates presenting an indication of at least one of the at least one prescription medication or the at least one artificial sensory experience to at least one user interface. For example, as shown in FIG. 1, presenter module 108 may present an indication of at least one of the at least one prescription medication or the at least one artificial sensory experience to at least one user interface. In one instance, presenter module 108 can present an indication of a prescription medication and an artificial sensory experience to a user interface. A user interface may include means by which an individual may interact with a system. Some examples of a user interface may include a touchscreen, a graphical user interface, a tactile interface, and/or a live user interface. In some instances, presenter module 108 may include a computer processor.

Figure 27:
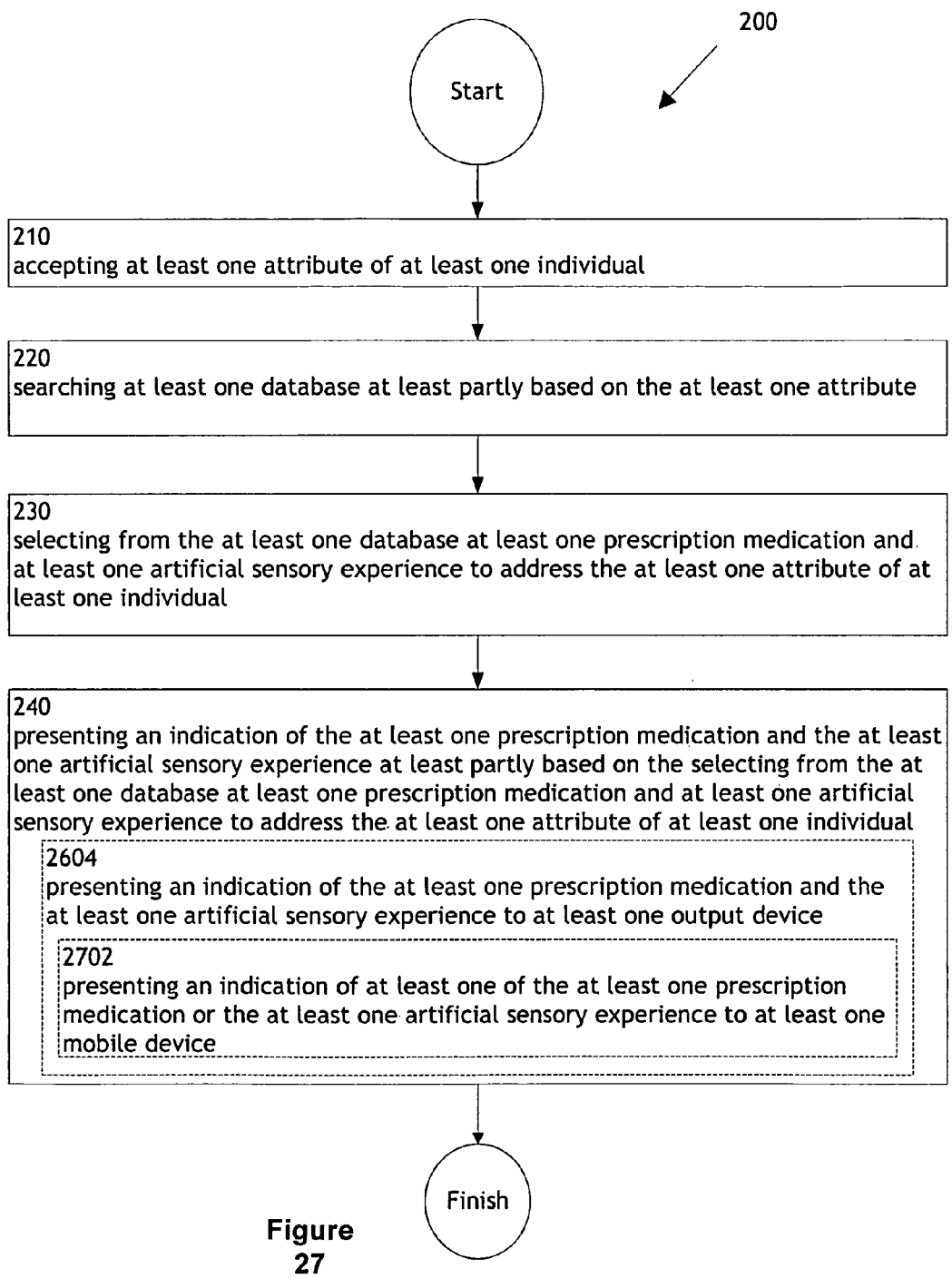
FIG. 27 illustrates an alternative embodiment of the operational flow of FIG. 2.

FIG. 27 illustrates alternative embodiments of the example operational flow 200 of FIG. 2. FIG. 27 illustrates example embodiments where operation 240 may include at least one additional operation. Additional operations may include an operation 2702. Further, operation 2702 illustrates presenting an indication of at least one of the at least one prescription medication or the at least one artificial sensory experience to at least one mobile device. For example, as shown in FIG. 1, presenter module 108 may present an indication of at least one of the at least one prescription medication or the at least one artificial sensory experience to at least one mobile device. In one instance, presenter module 108 can present an indication of a prescription medication to a mobile device 132. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, presenter module 108 may include a computer processor.

Figure 28:
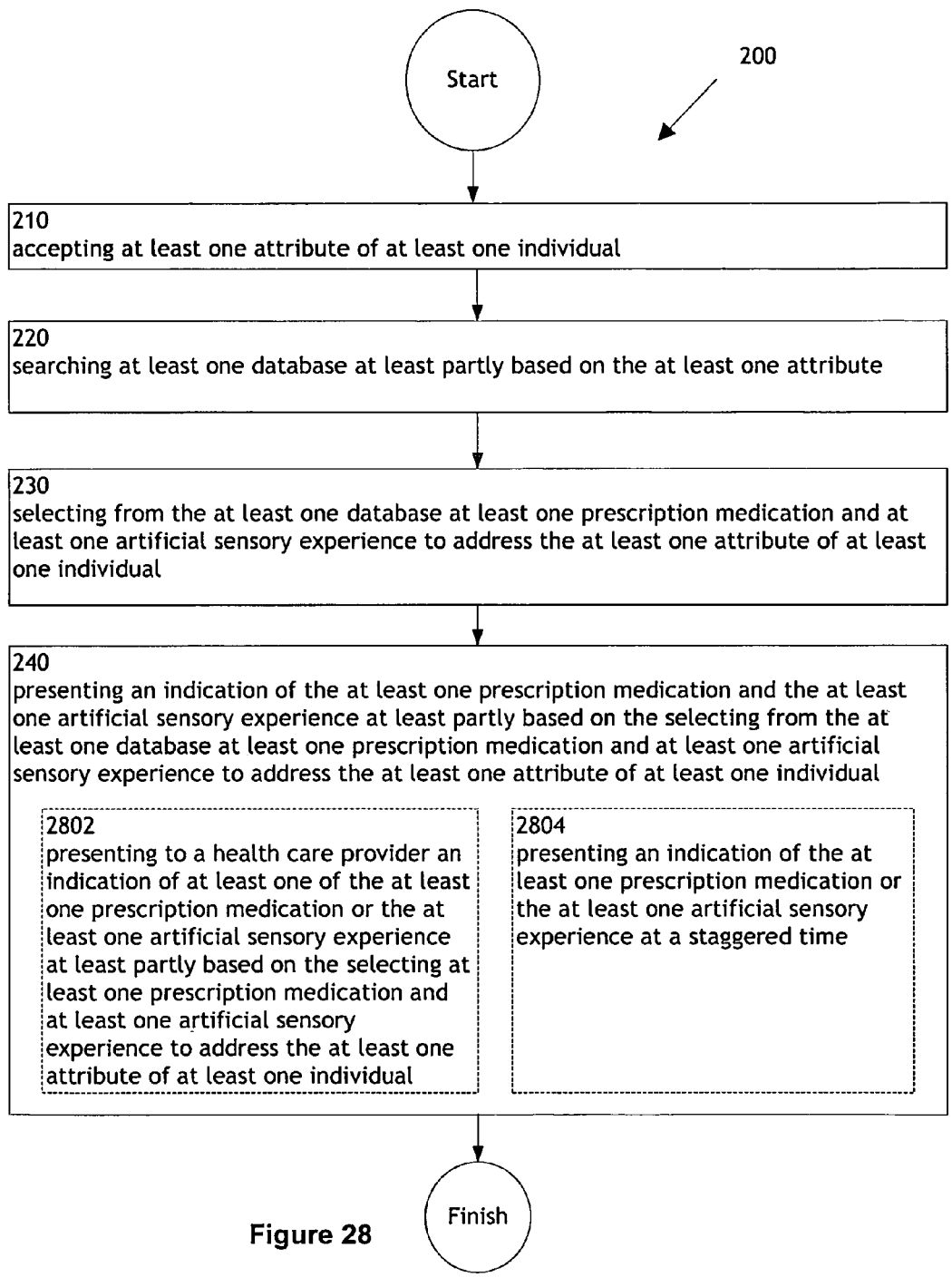
FIG. 28 illustrates an alternative embodiment of the operational flow of FIG. 2.

FIG. 28 illustrates alternative embodiments of the example operational flow 200 of FIG. 2. FIG. 28 illustrates example embodiments where operation 240 may include at least one additional operation. Additional operations may include an operation 2802, and/or an operation 2804.

Operation 2802 illustrates presenting to a health care provider an indication of at least one of the at least one prescription medication or the at least one artificial sensory experience at least partly based on the selecting at least one prescription medication and at least one artificial sensory experience to address the at least one attribute of at least one individual. For example, as shown in FIG. 1, presenter module 108 may present to a health care provider an indication of at least one of the at least one prescription medication or the at least one artificial sensory experience at least partly based on the selecting at least one prescription medication and at least one artificial sensory experience to address an attribute of an individual. In one example, presenter module 108 can present to a health care provider 128 an indication of a prescription medication based on the selecting at least one prescription medication and at least one artificial sensory experience to address the at least one attribute 120 of at least one individual. A health care provider may include a pharmacy, a pharmaceutical company, a medical device company, a research institution, a computer software and/or computer hardware company, a website, a nurse and/or a physician. In some instances, presenter module 108 may include a computer processor.

Operation 2804 illustrates presenting an indication of the at least one prescription medication or the at least one artificial sensory experience at a staggered time. For example, as shown in FIG. 1, presenter module 108 may present an indication of at least one of the at least one prescription medication or the at least one artificial sensory experience at a staggered time. In one example, presenter module 108 can present an indication of a series of prescription medications and an artificial sensory experience at staggered times. A staggered time may include presenting an indication of the at least one drug and/or artificial sensory experience at overlapping times and/or at different times, including alternating times. For example, at least one drug and an artificial sensory experience may be administered at an initial time and the same or a different drug may be administered when the first-administered at least one drug is at its peak effect. In another example, at least one drug and an artificial sensory experience may be administered at an initial time and the same or a different drug may be administered when the first administered at least one drug is at its lowest effect. In another example, an artificial sensory experience may be administered at an initial time and at least one prescription medication at a later time. The at least one artificial sensory experience and/or the at least one prescription medication may be administered at any number of times either concurrently, partially concurrently, or not concurrently. In some instances, presenter module 108 may include a computer processor.

Figure 29:
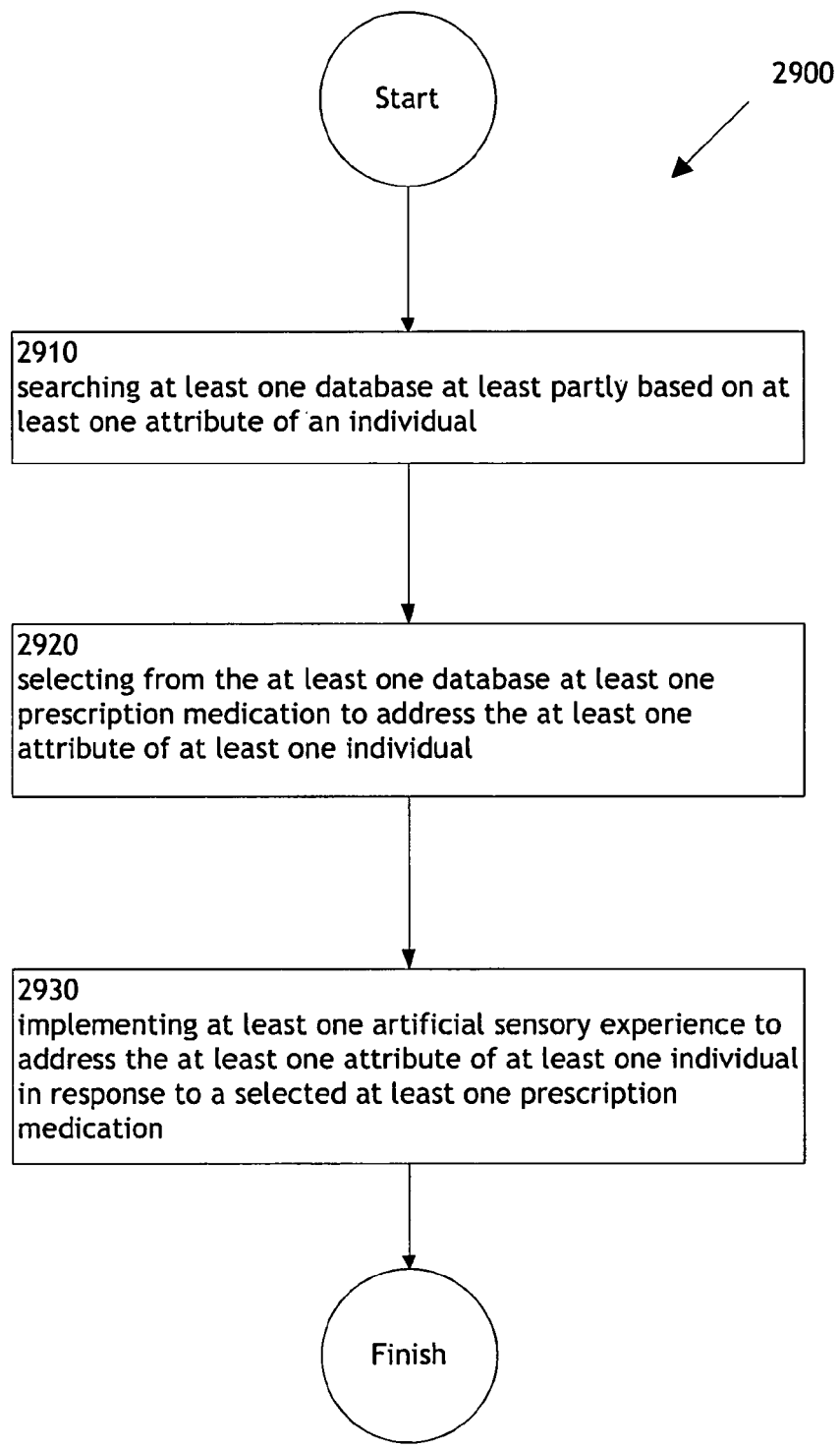
FIG. 29 illustrates an operational flow representing example operations related to selecting a combination of at least one prescription medication and at least one artificial sensory experience.

FIG. 29 illustrates an operational flow 2900 representing example operations related to querying at least one database at least partly based on at least one attribute of an individual, selecting from the at least one database at least one prescription medication to address the at least one attribute of at least one individual, and/or implementing at least one artificial sensory experience to address the at least one attribute of at least one individual in response to a selected at least one prescription medication. In FIG. 29, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 2900 moves to an operation 2910. Operation 2910 depicts querying at least one database at least partly based on at least one attribute of an individual. For example, as shown in FIG. 1, querier module 104 may search at least one database at least partly based on at least one attribute of an individual. In one instance, querier module 104 may search medication database 124 and artificial sensory experience database 126 based on an attribute 120 including an indication of hypertension associated with an individual named John Smith. In some instances, querier module 104 may include a computer processor.

Then, operation 2920 depicts selecting from the at least one database at least one prescription medication to address the at least one attribute of at least one individual. For example, as shown in FIG. 1, selector module 106 may select from the at least one database at least one prescription medication to address the at least one attribute of at least one individual. In one example and continuing with the previous example, selector module 106 may select from medication database 124 and artificial sensory experience database 126 a prescription medicine for addressing the attribute 120 including an indication of hypertension associated with an individual named John Smith. In some instances, selector module 106 may include a computer processor.

Then, operation 2930 depicts implementing at least one artificial sensory experience to address the at least one attribute of at least one individual in response to a selected at least one prescription medication. For example, as shown in FIG. 1, implementer module 138 may implement at least one artificial sensory experience to address the at least one attribute of at least one individual in response to a selected at least one prescription medication. In one instance and continuing with the previous example, implementer module 106 may implement an artificial sensory experience including a virtual world for addressing the attribute 120 including an indication of hypertension associated with an individual named John Smith in response to a selected prescription medication from a medication database 124. In some instances, selector module 106 may include a computer processor.

Figure 30:
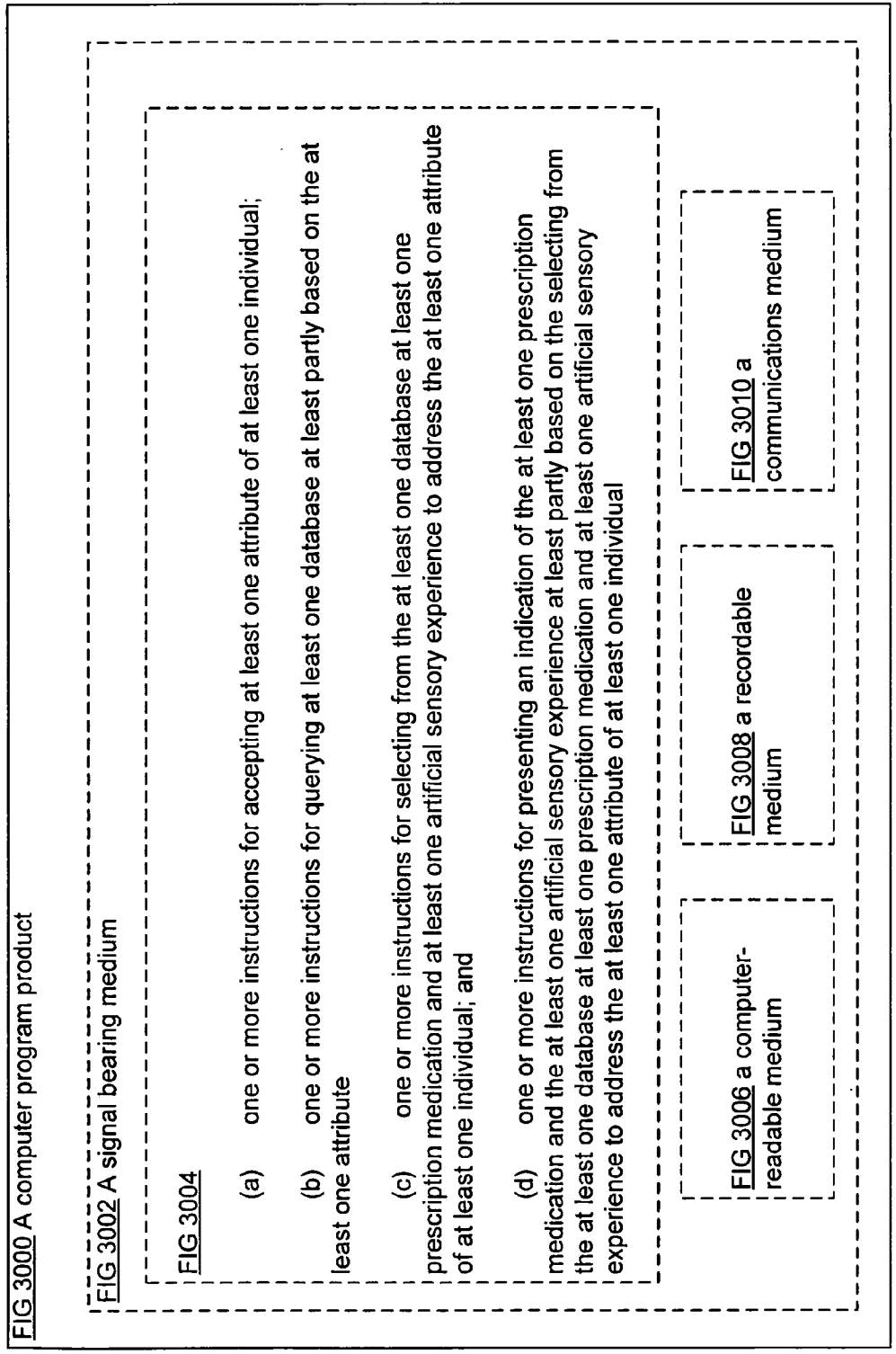
FIG. 30 illustrates a computer program product related to selecting a combination of at least one prescription medication and at least one artificial sensory experience.

FIG. 30 illustrates a partial view of an example computer program product 3000 that includes a computer program 3004 for executing a computer process on a computing device. An embodiment of the example computer program product 3000 is provided using a signal-bearing medium 3002, and may include one or more instructions for accepting at least one attribute of at least one individual; one or more instructions for querying at least one database at least partly based on the at least one attribute; one or more instructions for selecting from the at least one database at least one prescription medication and at least one artificial sensory experience to address the at least one attribute of at least one individual; and one or more instructions for presenting an indication of the at least one prescription medication and the at least one artificial sensory experience at least partly based on the selecting from the at least one database at least one prescription medication and at least one artificial sensory experience to address the at least one attribute of at least one individual. The one or more instructions may be, for example, computer executable and/or logic-implemented instructions. In one implementation, the signal-bearing medium 3002 may include a computer-readable medium 3006. In one implementation, the signal bearing medium 3002 may include a recordable medium 3008. In one implementation, the signal bearing medium 3002 may include a communications medium 3010.

FIG. 31 illustrates an example system 3100 in which embodiments may be implemented. The system 3100 includes a computing system environment. The system 3100 also illustrates the user 118 using a device 3104, which is optionally shown as being in communication with a computing device 3102 by way of an optional coupling 3106. The optional coupling 3106 may represent a local, wide-area, or peer-to-peer network, or may represent a bus that is internal to a computing device (e.g., in example embodiments in which the computing device 3102 is contained in whole or in part within the device 3104). A storage medium 3108 may be any computer storage media.

The computing device 3102 includes computer-executable instructions 3110 that when executed on the computing device 3102 cause the computing device 3102 to accept at least one attribute of at least one individual; query at least one database at least partly based on the at least one attribute; select from the at least one database at least one prescription medication and at least one artificial sensory experience to address the at least one attribute of at least one individual; and present an indication of the at least one prescription medication and the at least one artificial sensory experience at least partly based on the selecting from the at least one database at least one prescription medication and at least one artificial sensory experience to address the at least one attribute of at least one individual. As referenced above and as shown in FIG. 31, in some examples, the computing device 3102 may optionally be contained in whole or in part within the device 3104.

In FIG. 31, then, the system 3100 includes at least one computing device (e.g., 3102 and/or 3104). The computer-executable instructions 3110 may be executed on one or more of the at least one computing device. For example, the computing device 3102 may implement the computer-executable instructions 3110 and output a result to (and/or receive data from) the computing device 3104. Since the computing device 3102 may be wholly or partially contained within the computing device 3104, the device 3104 also may be said to execute some or all of the computer-executable instructions 3110, in order to be caused to perform or implement, for example, various ones of the techniques described herein, or other techniques.

The device 3104 may include, for example, a portable computing device, workstation, or desktop computing device. In another example embodiment, the computing device 3102 is operable to communicate with the device 3104 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Figure 32:
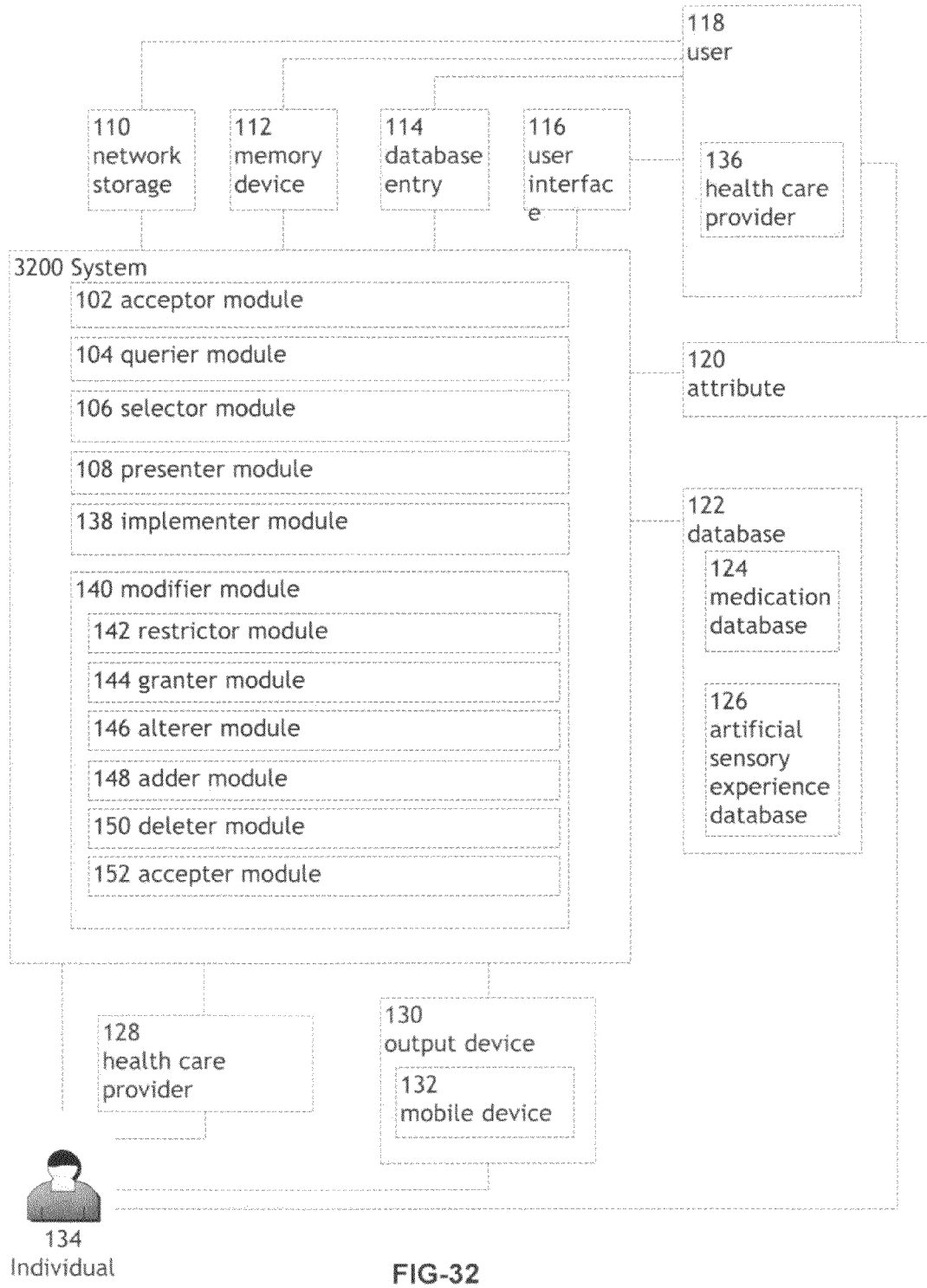
FIG. 32 illustrates an exemplary environment in which one or more technologies may be implemented.

FIG. 32 illustrates a system 3200 for accepting at least one indication of bioactive agent use by an individual and modifying an artificial sensory experience to alter at least one effect of the bioactive agent. The system 3200 may include acceptor module 102, querier module 104, selector module 106, presenter module 108, implementer module 138, and/or modifier module 140. Acceptor module 102 may receive attribute 120 from network storage 110, memory device 112, database entry 114, and/or user interface 116. User interface 116 may receive information from user 118. User 118 may include health care provider 136. Querier module 104 may search database 122. Database 122 may include medication database 124 and/or artificial sensory experience database 126. Presenter module 108 may present to health care provider 128, output device 130, and/or individual 134. Output device 130 may include mobile device 132. Modifier module 140 may include restrictor module 142, granter module 144, alterer module 146, adder module 148, deleter module 150, and/or acceptor module 152. System 3200 generally represents instrumentality for accepting at least one indication of bioactive agent use by an individual and modifying an artificial sensory experience to alter at least one effect of the bioactive agent. The operations of accepting at least one indication of bioactive agent use by an individual and modifying an artificial sensory experience to alter at least one effect of the bioactive agent may be accomplished electronically, such as with a set of interconnected electrical components, an integrated circuit, and/or a computer processor.

Figure 33:
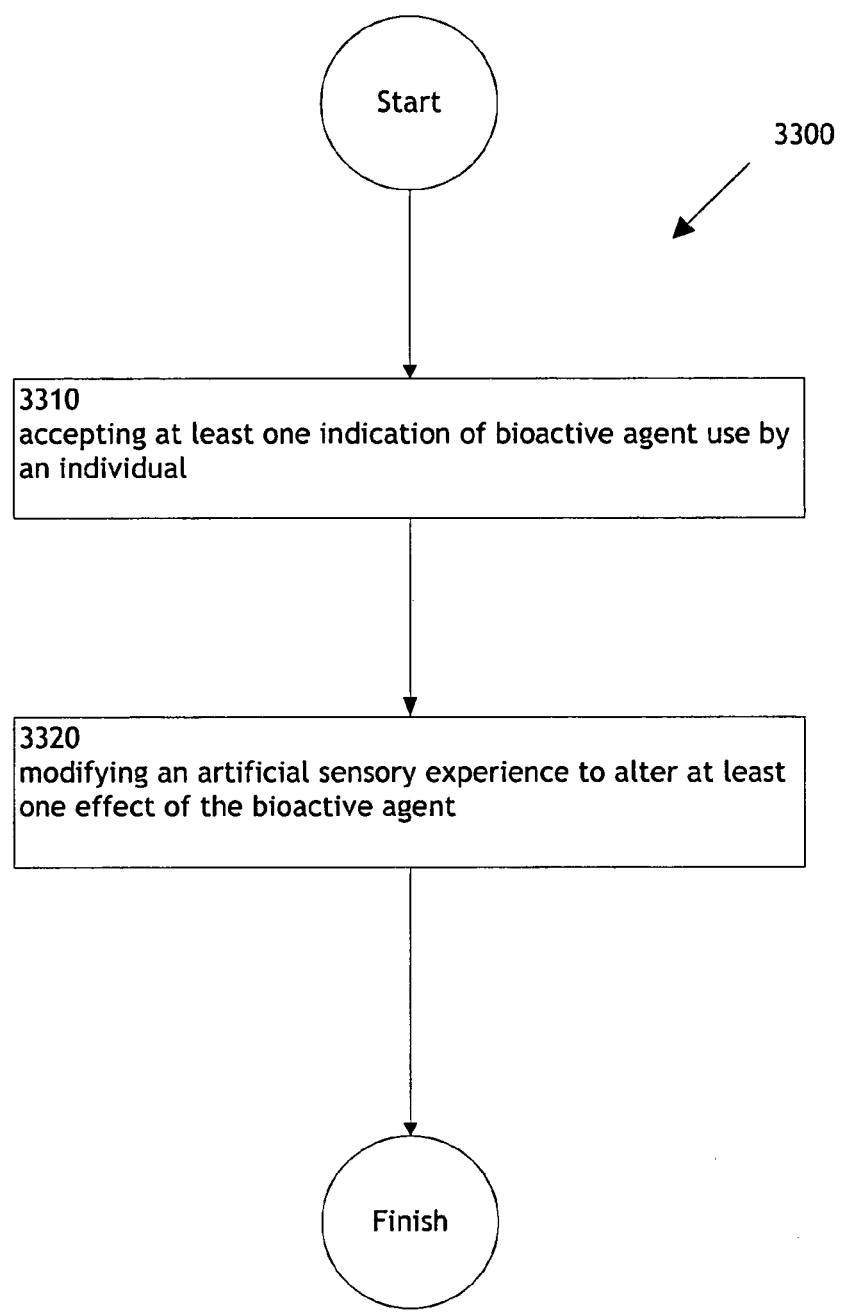
FIG. 33 illustrates an operational flow representing example operations related to modifying at least one artificial sensory experience.

FIG. 33 illustrates an operational flow 3300 representing example operations related to accepting at least one indication of bioactive agent use by an individual and modifying an artificial sensory experience to alter at least one effect of the bioactive agent. In FIG. 33 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 3300 moves to operation 3310. Operation 3310 depicts accepting at least one indication of bioactive agent use by an individual. For example, as shown in FIG. 1, acceptor module 102 may accept at least one indication of bioactive agent use by an individual. In one instance, acceptor module 102 may accept an indication of bioactive agent use including opioid use by an individual named Fred Johnson. An indication of bioactive agent use may include a showing of bioactive agent use, such as the results of a chemical test and/or input from a user 118 and/or health care provider 136. A bioactive agent may include an agent that may have a biochemical and/or biological effect on any part of the human body. One example of a bioactive agent may include a pharmaceutical agent, such as codeine and/or acetaminophen. Another example of a bioactive agent may include an illegal and/or addictive substance, such as methamphetamine and/or alcohol. Additionally, a bioactive agent may include an effect associated with the bioactive agent, such as a side effect, an adverse drug reaction, and/or an unintended therapeutic effect. In some instances, acceptor module 102 may include a computer processor.

Then, operation 3320 depicts modifying an artificial sensory experience to alter at least one effect of the bioactive agent. For example, as shown in FIG. 1, modifier module 140 may modify an artificial sensory experience to alter at least one effect of the bioactive agent. In one instance, modifier module 140 may modify an artificial sensory experience including a virtual world to alter an effect of the bioactive agent. Some examples of an artificial sensory experience may include a virtual experience, such as an online game or a social networking site, and/or a real-world sensory stimulus, such as a smell and/or a sight. Examples of modifying an artificial sensory experience may include changing a computer game and/or changing a computer display background.

One example of administering an artificial sensory experience may include a game utilizing a neuroheadset having sensors for detecting mental states based on, for example, electrical signals and/or blood flow in the brain. See for example headsets manufactured by Emotiv Systems, Inc. In some instances, modifier module 140 may include a computer processor.

Figure 34:
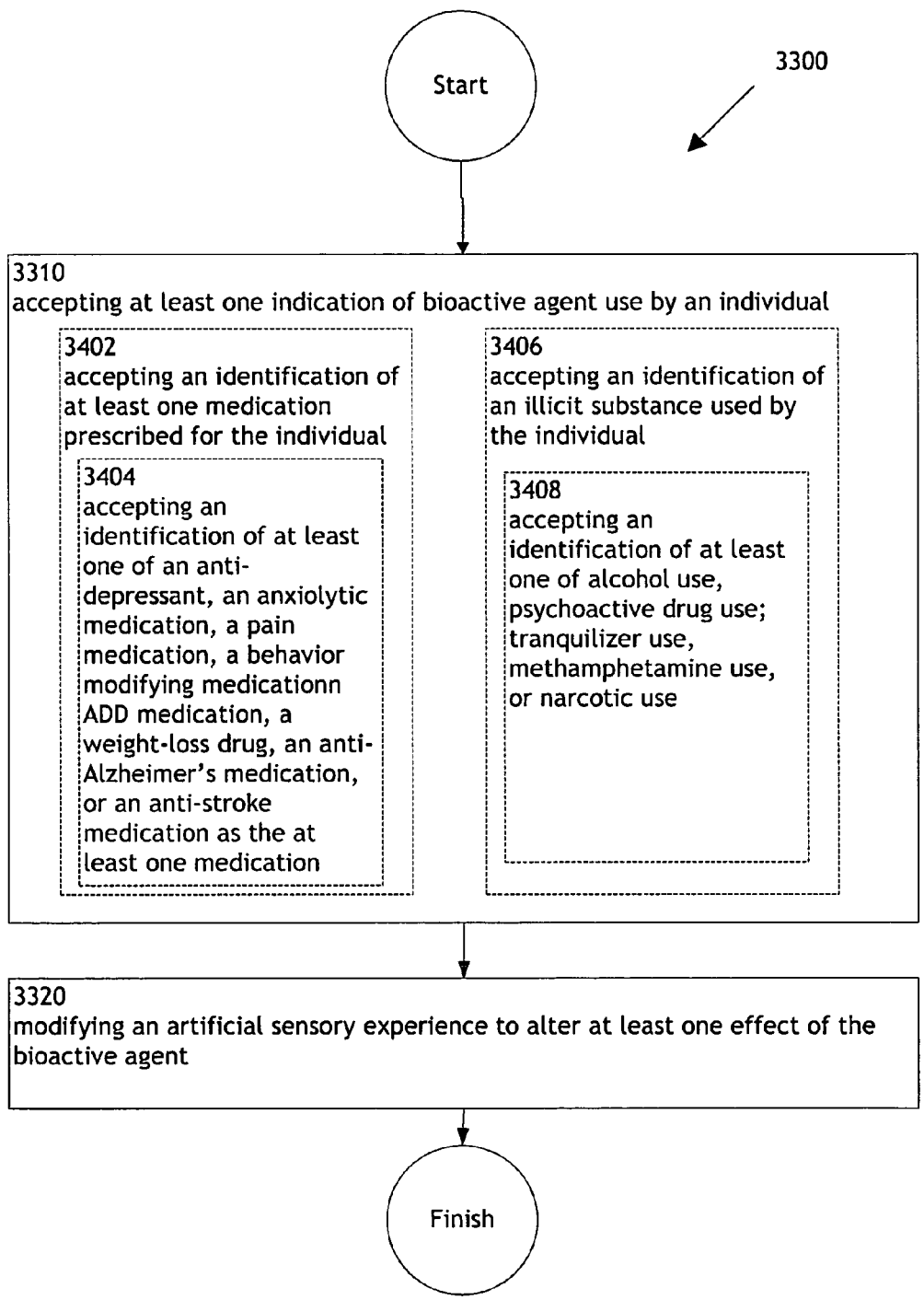
FIG. 34 illustrates an alternative embodiment of the operational flow of FIG. 33.

FIG. 34 illustrates alternative embodiments of the example operational flow 3300 of FIG. 33. FIG. 34 illustrates example embodiments where the operation 3310 may include at least one additional operation. Additional operations may include an operation 3402, an operation 3404, an operation 3406, and/or an operation 3408.

Operation 3402 illustrates accepting an identification of at least one medication prescribed for the individual. For example, as shown in FIG. 1, acceptor module 102 may accept an identification of at least one medication prescribed for the individual. In one instance and continuing with the example above, acceptor module 102 may accept from user 118 and user interface 116 an identification of a medication including codeine prescribed for the individual named Fred Johnson. In some instances, acceptor module 102 may include a computer processor. Further, the operation 3404 illustrates accepting an identification of at least one of an anti-depressant, an anxiolytic medication, a pain medication, a behavior modifying medication, a weight-loss drug, an anti-Alzheimer's medication, or an anti-stroke medication as the at least one medication. For example, as shown in FIG. 1, acceptor module 102 may accept an identification of at least one of an anti-depressant, an anxiolytic medication; a pain medication, a behavior modifying medication; a weight-loss drug, an anti-Alzheimer's medication, or an anti-stroke medication as the at least one medication. In one instance, acceptor module 102 may accept from user 118 and memory device 112 an identification of a pain medication. An anti-depressant may include a psychiatric medication or other substance, such as a nutrient or herb, used for alleviating depression or dysthymia. Some examples of an anti-depressant may include fluoxetine and/or sertraline. An anxiolytic medication may include a substance used for the treatment of anxiety, such as a benzodiazepine and/or a barbiturate. A pain medication may include any substance and/or drug used to relieve pain. Some examples of an analgesic may include narcotics such as morphine or oxycodone, non-narcotics, an NSAID such as aspirin or naproxen or ibuprofen, and/or acetaminophen. A behavior modifying medication may include a substance used for preventing or reducing behavior associated with attention-deficit disorder (ADD) and/or attention-deficit hyperactivity disorder (ADHD). Additional behavior modifying medications may include medications used to treat attention deficiency, hyperactivity, attachment disorders, associative disorders, oppositional defiant disorder, aggression, and/or autistic spectrum disorders. Some examples of a behavior modifying medication may include methylphenidate, dextroamphetamine, and/or mixed amphetamine salts. A weight-loss drug may include a drug and/or supplement used for decreasing appetite, blocking fat absorption, and/or decreasing stomach volume. Some examples of a weight-loss drug may include DHEA, pregnenolone, orlistat, sibutramine, and/or melatonin. An anti-Alzheimer's medication may include medication used for the prevention and/or management of Alzheimer's disease. Some examples of an anti-Alzheimer's medication may include memantine, donepezil, gatantamine, and/or rivastigmine. An anti-stroke medication may include medication used for preventing and/or treating stroke and/or symptoms of stroke. Some examples of anti-stroke medication may include aspirin, clopidogrel, and/or ticlopidine. In some instances, acceptor module 102 may include a computer processor.

Operation 3406 illustrates accepting an identification of an illicit substance used by the individual. For example, as shown in FIG. 1, acceptor module 102 may accept an identification of an illicit substance used by the individual. In one instance, acceptor module 102 may accept from user 118 and network storage 110 an identification of an illicit substance including cocaine used by an anonymous individual. An illicit substance may include a psychoactive drug or performance enhancing drug used for a non-therapeutic or non-medical effect. Some examples of an illicit substance may include alcohol, amphetamines, barbiturates, benzodiazepines, cocaine, methaqualone, and/or opium alkaloids. In some instances, acceptor module 102 may include a computer processor. Further, the operation 3408 illustrates accepting an identification of at least one of alcohol use, psychoactive drug use, tranquilizer use, methamphetamine use, or narcotic use. For example, as shown in FIG. 1, acceptor module 102 may accept an identification of at least one of alcohol use, psychoactive drug use; tranquilizer use, methamphetamine use, or narcotic use. In one instance, acceptor module 102 may accept an identification of alcohol use and methamphetamine use from health care provider 136 and user interface 116. Alcohol use may include alcohol abuse, alcohol dependence, alcoholism, and/or recreational alcohol consumption. Psychoactive drug use, tranquilizer use, methamphetamine use, and/or narcotic use may include recreational drug and/or substance use and/or drug abuse. In some instances, acceptor module 102 may include a computer processor.

Figure 35:
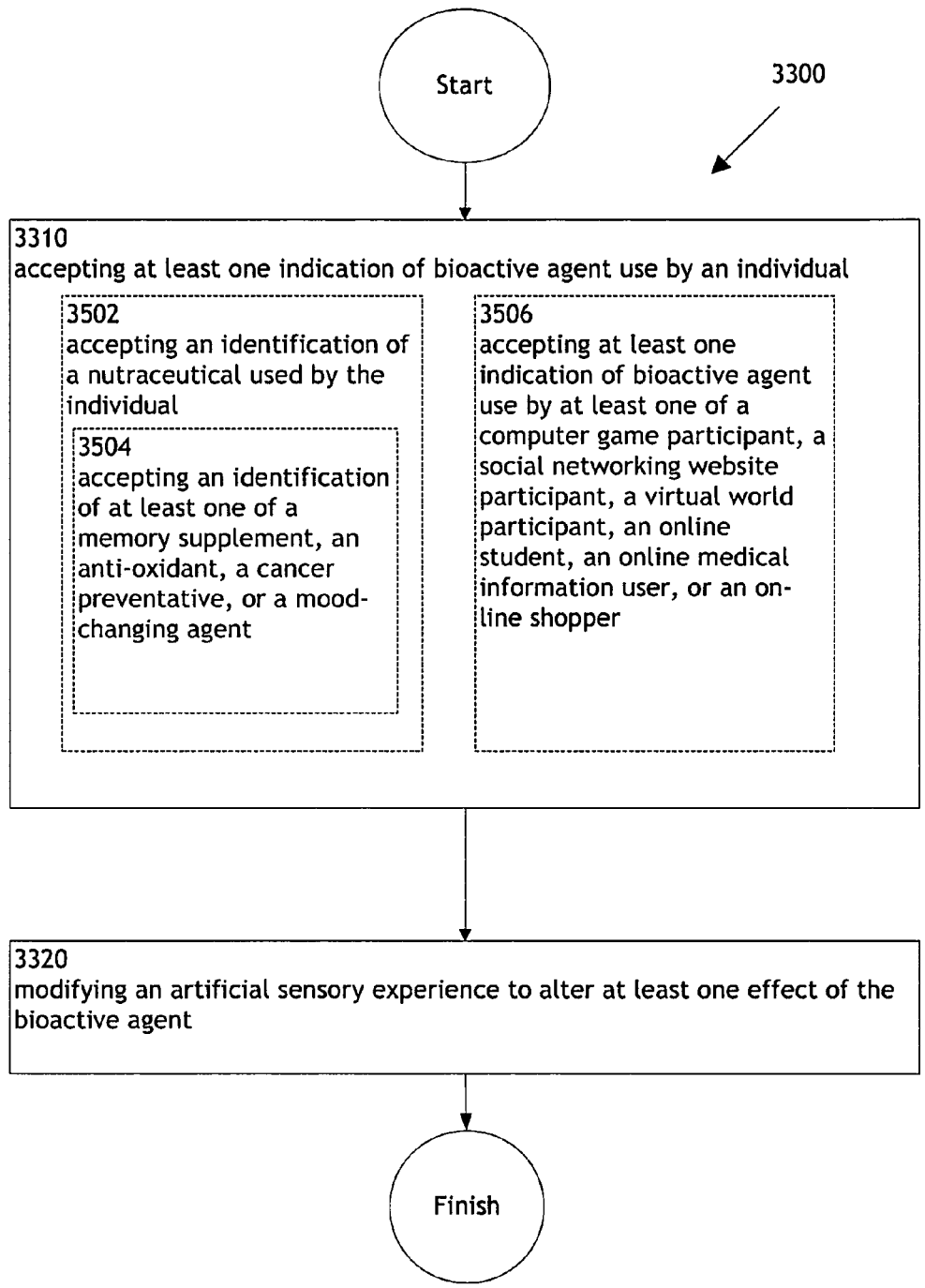
FIG. 35 illustrates an alternative embodiment of the operational flow of FIG. 33.

FIG. 35 illustrates alternative embodiments of the example operational flow 3300 of FIG. 33. FIG. 35 illustrates example embodiments where the operation 3310 may include at least one additional operation. Additional operations may include an operation 3502, an operation 3504, and/or an operation 3506.

Operation 3502 illustrates accepting an identification of a nutraceutical used by the individual. For example, as shown in FIG. 1, acceptor module 102 may accept an identification of a nutraceutical used by the individual. In one instance, acceptor module 102 may accept an identification of a nutraceutical including a soy-based isoflavonoid used by the individual. A nutraceutical may refer to a food extract claimed to have a medicinal effect on human health. Some examples of a nutraceutical may include flavonoid antioxidants, alpha-linolenic acid from flax seeds, beta-carotene from marigold petals, anthocyanins from berries, ginseng, and/or garlic oil. In some instances, acceptor module 102 may include a computer processor. Further, operation 3504 illustrates accepting an identification of at least one of a memory supplement, an anti-oxidant, a cancer preventative, or a mood-changing agent. For example, as shown in FIG. 1, acceptor module 102 may accept from health care provider 136 and user interface 116 an identification of at least one of an memory supplement, an anti-oxidant, a cancer preventative, or a mood-changing agent. In one instance, acceptor module 102 may accept an identification of an herbal memory supplement including ginkgo biloba. A memory supplement may include a substance obtained from an animal and/or a plant source for maintaining and/or improving memory, such as salvia lavandulaefolia and/or ginkgo biloba. An anti-oxidant may include a substance capable of slowing or preventing the oxidation of other molecules and is purported to neutralize hazardous free-radicals within the body. Some examples of an antioxidant may include ascorbic acid, glutathione, melatonin, and/or tocopherot. A cancer preventative may include a drug, a treatment, and/or substance utilized for preventing the occurrence of and/or the progression of cancer. Some examples of a cancer preventative may include acupuncture, all-trans retinoic acid, mistletoe derivatives, and/or lycopene. A mood-changing agent may include a psychiatric medication used to treat mood disorders characterized by intense and sustained mood shifts. Some examples of a mood-changing agent may include lithium carbonate and/or lamotrigine. In some instances, acceptor module 102 may include a computer processor.

Operation 3506 illustrates accepting at least one indication of bioactive agent use by at least one of a computer game participant, a social networking website participant, a virtual world participant, an online student, an online medical information user, or an on-line shopper. For example, as shown in FIG. 1, acceptor module 102 may accept at least one indication of bioactive agent use by at least one of a computer game participant, a social networking website participant, a virtual world participant, an online student, an online medical information user, or an on-line shopper. In one instance, acceptor module 102 may accept an indication of bioactive agent use by a virtual world participant. In another instance, acceptor module 102 may accept an indication of bioactive agent use by an online student enrolled in an online college course through a community college. In another instance, acceptor module 102 may accept an indication of bioactive agent use by an online medical information user using a secure connection. Online communications may include private and/or confidential communications using a secure method, such as a secure web browser and/or a secure internet connection, for ensuring the privacy of a user and/or participant. A computer game may include an online game, an online educational experience, a networked game, and/or a single-player game. Some examples of computer games may include World of Warcraft (WoW), solitaire, and/or RuneScape. A social networking website may include a website for observing and/or interacting with one or more personal and/or professional relationships between individuals. Some examples of a social networking website may include MySpace, GeoCities, Facebook, and/or LinkedIn. A virtual world may include a computer-based simulated environment intended for its users to inhabit and interact via avatars, such as Second Life. An online student may be enrolled in and/or learn from an online educational experience such as a tutorial, a lesson, and/or an online class. Some examples of an online educational experience may include a HTML tutorial, an online piano lesson, and/or an online degree program from the University of Phoenix. Online medical information may include a website and/or a database, such as http://www.ncbi.nim.gov/pubmed/, MEDLINE, MEDLARS, and/or www.webmd.com. An online shopper may shop at an internet marketplace, such as eBay.com, Amazon.com, and/or Froogle.com. In some instances, acceptor module 102 may include a computer processor.

Figure 36:
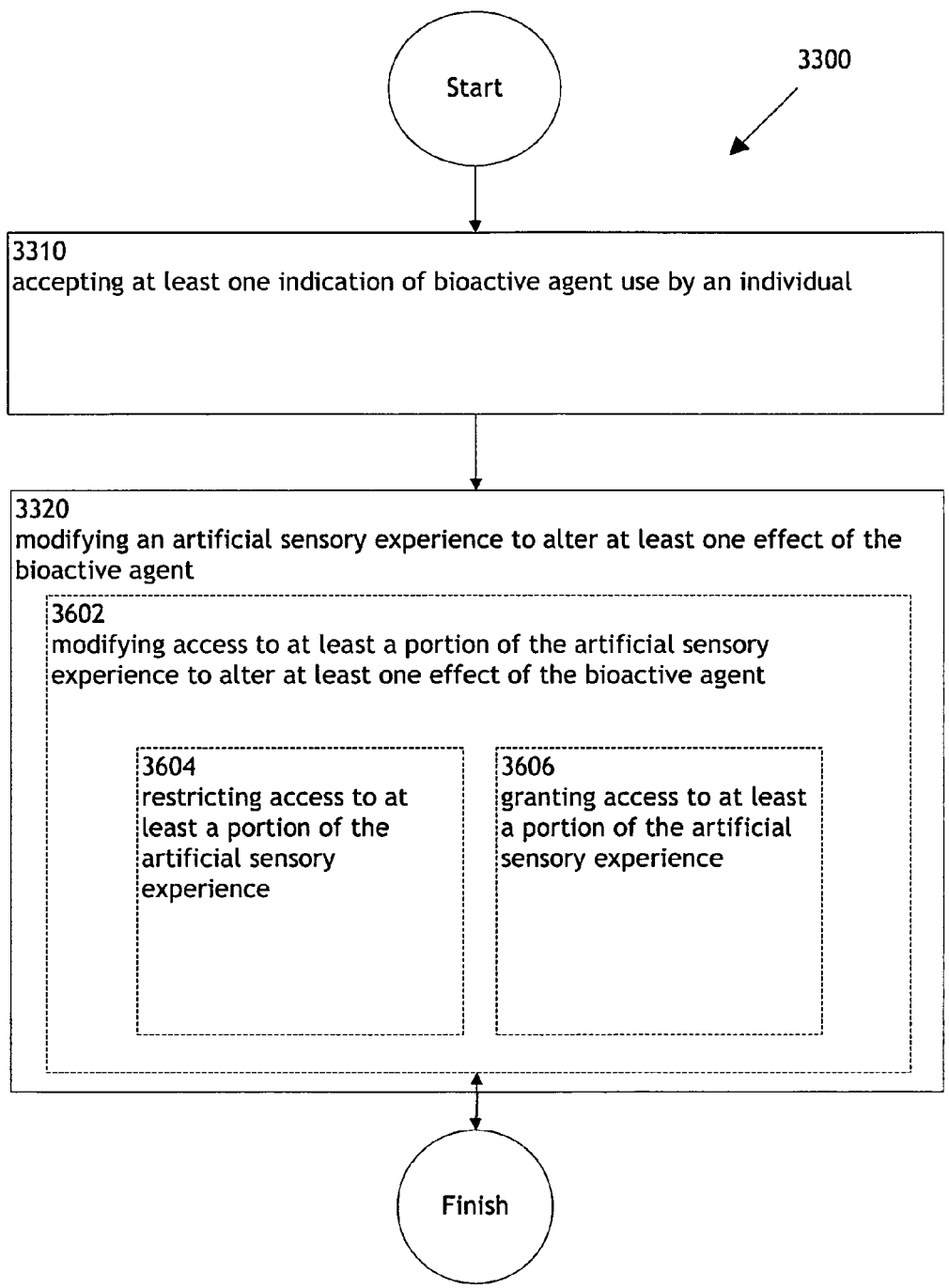
FIG. 36 illustrates an alternative embodiment of the operational flow of FIG. 33.

FIG. 36 illustrates alternative embodiments of the example operational flow 3300 of FIG. 33. FIG. 36 illustrates example embodiments where the operation 3320 may include at least one additional operation. Additional operations may include an operation 3602, an operation 3604, and/or an operation 3606.

The operation 3602 illustrates modifying access to at least a portion of the artificial sensory experience to alter at least one effect of the bioactive agent. For example, as shown in FIG. 1, modifier module 140 may modify access to at least a portion of the artificial sensory experience to alter at least one effect of the bioactive agent. In one instance, modifier module 140 may modify access to a portion of an artificial sensory experience including a photo gallery portion of a social networking website to alter at least one effect of the bioactive agent including an antidepressant. Such modified access may function therapeutically to prevent access of an individual to potentially depressing, stressful, or otherwise triggering sensory experiences, and/or the modified access may involve presentation of a sensory experience that affirmatively improves a condition (e.g., bright sunny images for a clinically depressed individual). In some instances, modifier module 140 may include a computer processor. Further, the operation 3604 illustrates restricting access to at least a portion of the artificial sensory experience. For example, as shown in FIG. 1, restrictor module 142 may restrict access to at least a portion of the artificial sensory experience. In one instance, restrictor module 142 may restrict access to a portion of an artificial sensory experience including a virtual world designed to overcome a flying phobia, where access to a portion of a simulated flying experience is restricted including a jet take-off portion. In some instances, restrictor module 142 may include a computer processor. Further, the operation 3606 illustrates granting access to at least a portion of the artificial sensory experience. For example, as shown in FIG. 1, granter module 144 may grant access to at least a portion of the artificial sensory experience. In one instance and continuing with the above example, granter module 144 may grant access to at least a portion of a virtual world designed to overcome a flying phobia, where access to a portion of a simulated flying experience is granted including a jet landing portion. Such a simulation with gradually increasing contact with the object of the fear may serve to provide conditioning for the individual to eventually overcome the phobia. In some instances, granter module 144 may include a computer processor.

Figure 37:
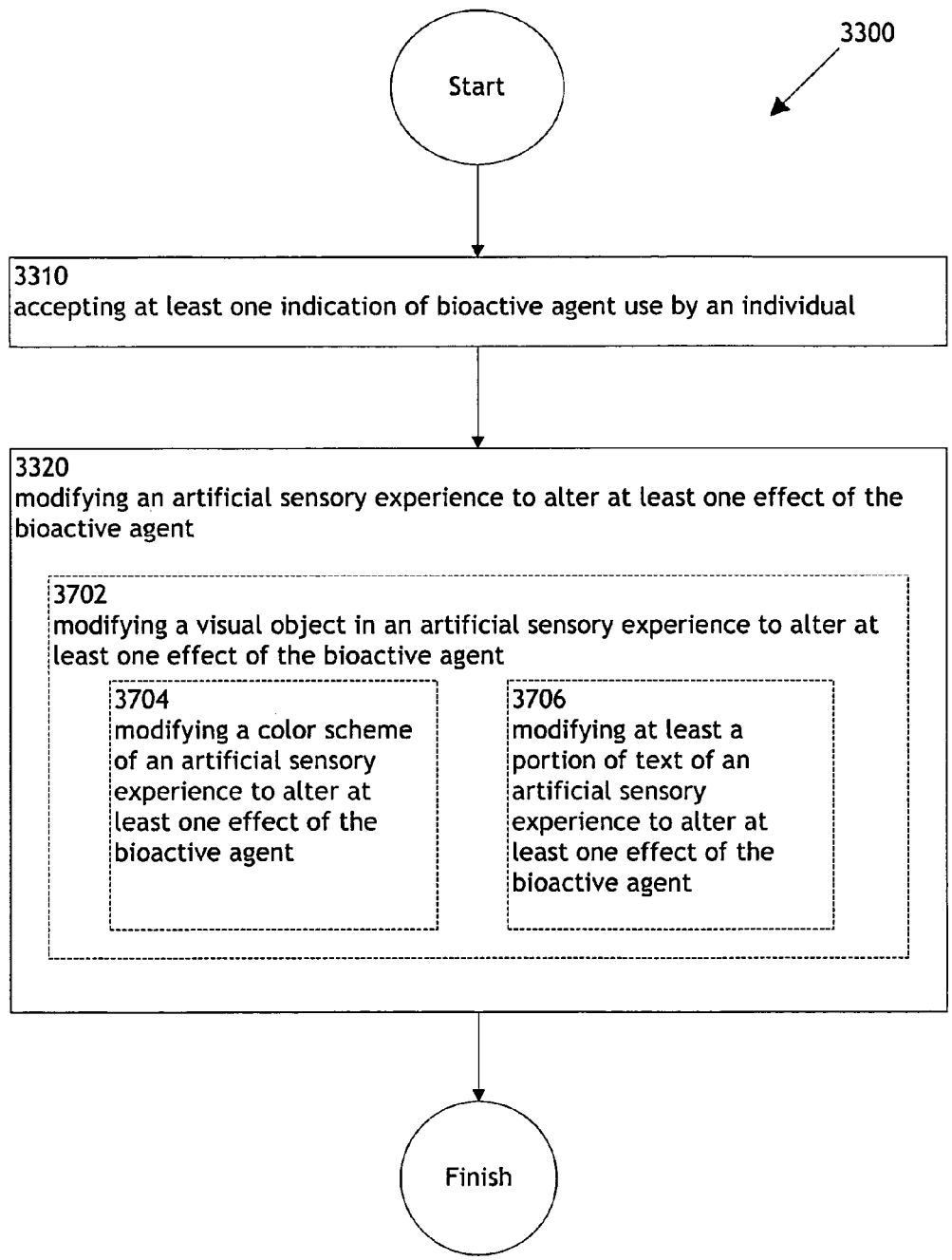
FIG. 37 illustrates an alternative embodiment of the operational flow of FIG. 33.

FIG. 37 illustrates alternative embodiments of the example operational flow 3300 of FIG. 33. FIG. 37 illustrates example embodiments where the operation 3320 may include at least one additional operation. Additional operations may include an operation 3702, an operation 3704, and/or an operation 3706.

Operation 3702 illustrates modifying a visual object in an artificial sensory experience to alter at least one effect of the bioactive agent. For example, as shown in FIG. 1, modifier module 140 may modify a visual object in an artificial sensory experience to alter at least one effect of the bioactive agent. In one instance and continuing with the above example, modifier module 140 may modify a visual object, such as adding window covers, in a virtual world designed to overcome a flying phobia to alter at least one effect of an anti-anxiety medication. In this example, the window covers may reduce anxiety experienced by the individual in addition to anxiety reduction mediated by the anti-anxiety medication. Additional examples of a visual object may include an avatar, a virtual character, an action performed by the avatar and/or virtual character, and/or character artifacts, such as weapons, clothing, and/or tools. In some instances, modifier module 140 may include a computer processor. Further, the operation 3704 illustrates modifying a color scheme of an artificial sensory experience to alter at least one effect of the bioactive agent. For example, as shown in FIG. 1, modifier module 140 may modify a color scheme of an artificial sensory experience to alter at least one effect of the bioactive agent. In one instance, modifier module 140 may modify a color scheme by adding brighter background lights and colors in a virtual world designed to overcome depression to alter an effect of an anti-depression medication. Such a color scheme modification may help to overcome depression, seasonal affective disorder, and/or other disorders because it has been purported that color and/or light may affect nonvisual psychological processes. Discussion regarding the effects of color and/or light on nonvisual psychological processes may be found in Knez, Effects of colour of light on nonvisual psychological processes, JOURNAL OF ENVIRONMENTAL PSYCHOLOGY, 21(2):201-208 (2001); M. R Basso Jr., Neurobiological relationships between ambient lighting and the startle response to acoustic stress in humans, INT J NEUROSCI., 110(3-4):147-57 (2001), and Lam et al., *The Can-SAD Study: a randomized controlled trial of the effectiveness of light therapy and fluoxetine in patients with winter seasonal affective disorder*, AMERICAN JOURNAL OF PSYCHIATRY, 163(5):805-12 (2006), each incorporated by reference. In some instances, modifier module 140 may include a computer processor. Further, the operation 3706 illustrates modifying at least a portion of text of an artificial sensory experience to alter at least one effect of the bioactive agent. For example, as shown in FIG. 1, modifier module 140 may modify at least a portion of text of an artificial sensory experience to alter at least one effect of the bioactive agent. In one instance, modifier module 140 may modify a portion of instructional text in a virtual world including a computer game to alter an effect of a bioactive agent including a prescribed herbal memory supplement. Text modification may improve memory by utilizing techniques such as underlining, highlighting, boldfacing, and/or mnemonics as discussed in Carney, R. N., & Levin, J. R., *Mnemonic instruction with a focus on transfer*, JOURNAL OF EDUCATIONAL PSYCHOLOGY, 92(4):783-90, incorporated herein by reference. Another example may include instructional text providing contextual or associative information, perhaps individualized, to aid in remembering during the rest of a module. Another example of text modification and memory may include modifying the use of interactive components, e.g. via a keyboard and/or speakers, to use multiple forms of memory input, including visual, auditory, motor, and contextual. For example, this may be used to aid memory and/or in learning disorders such as dysgraphia, and/or memory disorders, such as in conjunction with memory-enhancing medications, for example cholinesterase inhibitors or herbal memory supplements. Additionally, text messages may be added and/or altered based on cognitive therapy but individualized for the person, affliction, and/or medication (e.g. an antidepressant and instructions to work toward a goal within a game that will aid in refuting automatic negative thoughts). In some instances, modifier module 140 may include a computer processor.

Figure 38:
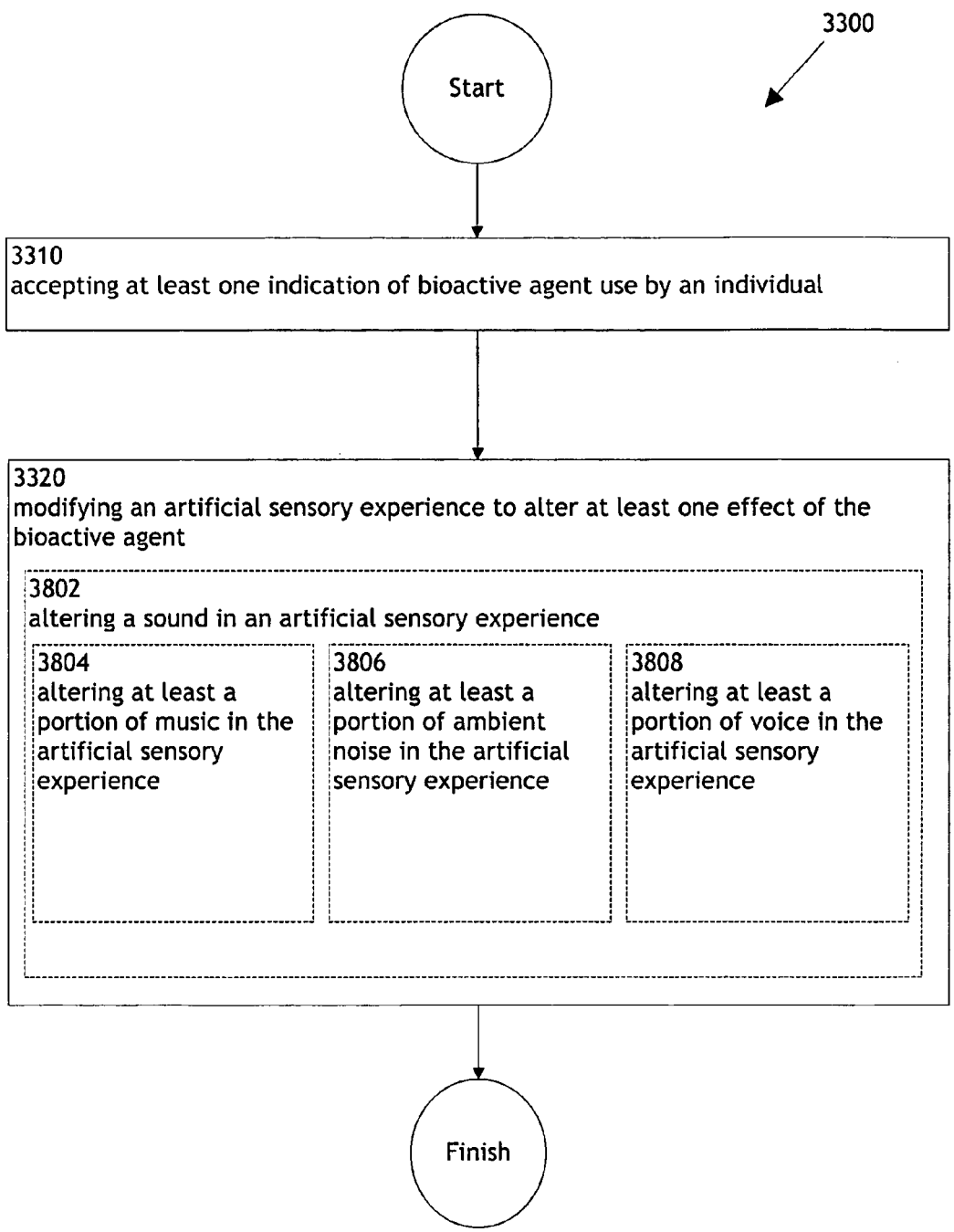
FIG. 38 illustrates an alternative embodiment of the operational flow of FIG. 33.

FIG. 38 illustrates alternative embodiments of the example operational flow 3300 of FIG. 33. FIG. 38 illustrates example embodiments where the operation 3320 may include at least one additional operation. Additional operations may include an operation 3802, an operation 3804, an operation 3806, and/or an operation 3808.

The operation 3802 illustrates altering a sound in an artificial sensory experience. For example, as shown in FIG. 1, alterer module 146 may alter a sound in an artificial sensory experience. In one instance, alterer module 146 may alter a sound in a virtual world including an instructor's voice tone in an instructional tutorial. This may be done as a custom-tailored feature. For example, various voice tones may be tested with an individual in order to find one that has the most significant benefit for the individual, in conjunction with the bioactive agent. In some instances, alterer module 146 may include a computer processor. Further, the operation 3804 illustrates altering at least a portion of music in the artificial sensory experience. For example, as shown in FIG. 1, alterer module 146 may alter at least a portion of music in the artificial sensory experience. In one instance, alterer module 146 may alter a portion of music including background music in an instructional tutorial. Music in the artificial sensory experience may include pitch, rhythm, tempo, meter, and articulation, dynamics, lyrics, timbre and texture. In one specific instance, alterer module 146 may alter a portion of uptempo music to soothing classical music in an artificial sensory experience coupled with administration of an anxiolytic. Such a music alteration may serve to provide a calming and/or relaxing environment where the effects of the anxiolytic may be facilitated. In another instance, a sound pitch may be altered to affect bone (as in healing fractures and/or promoting bone growth) and/or sinuses (including joints). Additionally, alterer module 146 may include providing another type of sound, such as a low frequency, to aid in healing, e.g. in conjunction with pain medication and/or an anti-inflammatory medication. In another example, the sound may originate from a natural source, for instance a purr of a cat, possibly provided at a particular pitch, to aid in relaxation, as in conjunction with a tranquilizer, and/or in healing tissue in conjunction with pain medication or anti-inflammatories. Further discussion regarding low frequency therapeutic biomechanical stimulation may be found in von Muggenthaler, E. K., *The Fetid purr: low frequency therapeutic biomechanical stimulation*, 12th International Conference on Low Frequency Noise and Vibration and its Control, Bristol, UK, Sep. 18-20, 2006, Abstract located at Fauna Communications Research Institute <http://animalvoice.com/catpurrP.htm#2pAB7.%20The%20felid%20purr:% 20A%20healing%20mechanism?%20Session:% 20Tuesday%20Afternoon,%20Dec%2004%20Time:% 203: 15>, and Simos et al., U.S. patent application Ser. No. 11/262, 884, each incorporated herein by reference. In some instances, alterer module 146 may include a computer processor. Further, the operation 3806 illustrates altering at least a portion of ambient noise in the artificial sensory experience. For example, as shown in FIG. 1, alterer module 146 may alter at least a portion of ambient noise in the artificial sensory experience. In one instance, alterer module 146 may alter the ambient noise in an artificial sensory experience including a level of white noise in the online virtual world Second Life. Ambient noise may include white noise, background noise, such as people talking or sounds naturally occurring in nature, and/or room noise. Changing the level of white noise may enhance the effect of an attention deficit drug such as Ritalin, or it may enhance the sedative properties of a sleep medication or tranquilizer. Further discussion of the effects of white noise may be found in Spencer, J. A. et al., White noise and sleep induction, ARCH DIS CHILD 65(1):135-7 (1990). In some instances, alterer module 146 may include a computer processor. Further, the operation 3808 illustrates altering at least a portion of voice in the artificial sensory experience. For example, as shown in FIG. 1, alterer module 146 may alter at least a portion of voice in the artificial sensory experience. In one instance, alterer module 146 may alter a voice rhythm in an online tutorial. Such alteration may enhance the effect of an attention deficit medication, for example by elimination or reduction of monotonic qualities in the voice rhythm of the online tutorial, for example. Some examples of a voice may include a voice recording, an artificially generated voice, and/or a human voice. In some instances, alterer module 146 may include a computer processor.

Figure 39:
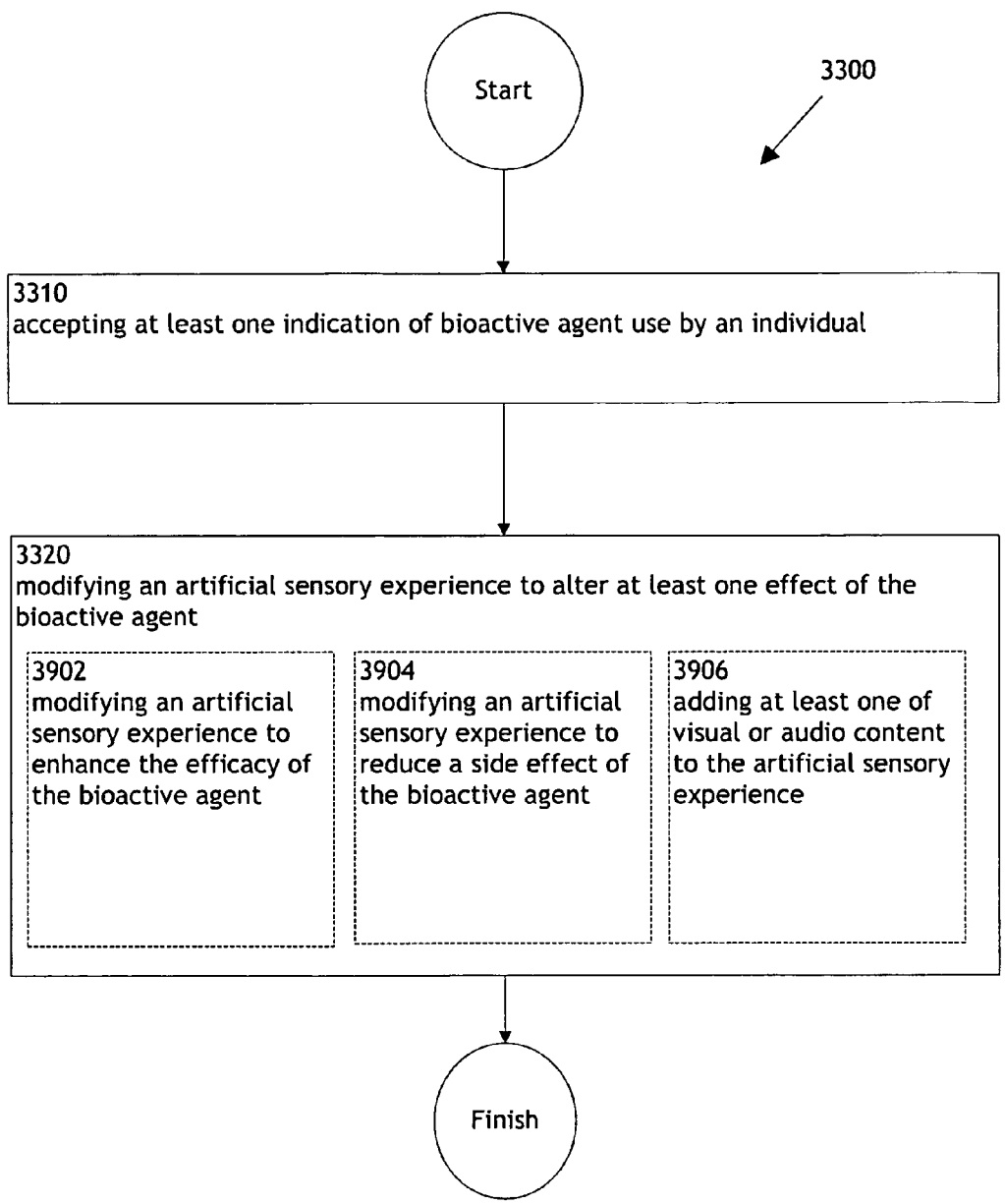
FIG. 39 illustrates an alternative embodiment of the operational flow of FIG. 33.

FIG. 39 illustrates alternative embodiments of the example operational flow 3300 of FIG. 33. FIG. 39 illustrates example embodiments where the operation 3320 may include at least one additional operation. Additional operations may include an operation 3902, an operation 3904, and/or an operation 3906.

The operation 3902 illustrates modifying an artificial sensory experience to enhance the efficacy of the bioactive agent. For example, as shown in FIG. 1, modifier module 140 may modify an artificial sensory experience to enhance the efficacy of the bioactive agent. In one instance, modifier module 140 may modify a virtual world by adding uptempo music to enhance the efficacy of an antidepressant. Further discussion of music effects may be found in Schellenberg, E. G. et al., *Exposure to music and cognitive performance: tests of children and adults*, PSYCHOLOGY OF MUSIC, Vol. 35, No. 1, 5-19 (2007), incorporated herein by reference. In some instances, modifier module 140 may include a computer processor.

The operation 3904 illustrates modifying an artificial sensory experience to reduce a side effect of the bioactive agent. For example, as shown in FIG. 1, modifier module 140 may modify an artificial sensory experience to reduce a side effect of the bioactive agent. In one instance, modifier module 140 may modify a virtual world by adding music and/or sounds occurring in nature for reducing a side effect including a headache due to an administration of penicillin. Further discussion of music effects upon a side effect may be found in Siedliecki, S. L. and Good, M., *Effect of music on power, pain, depression and disability*, JOURNAL OF ADVANCED NURSING 54(5):553-562 (2006), and *Natural' distractions reduce pain—study finds that sights and sounds of nature aid in pain reduction—Brief Article*, MEN'S FITNESS. October 2001, each incorporated by reference. In some instances, modifier module 140 may include a computer processor.

The operation 3906 illustrates adding at least one of visual or audio content to the artificial sensory experience. For example, as shown in FIG. 1, adder module 148 may add at least one of visual or audio content to the artificial sensory experience. In one instance, adder module 148 may add audio content including calming music to an artificial sensory experience including a virtual world for treating a phobia of heights. Adding may include increasing, creating, and/or combining content. Some examples of visual content may include visual objects, light amount and/or intensity, and or color schemes. Examples of audio content may include music, voices, artificial sounds, and/or white noise. In some instances, adder module 148 may include a computer processor.

Figure 40:
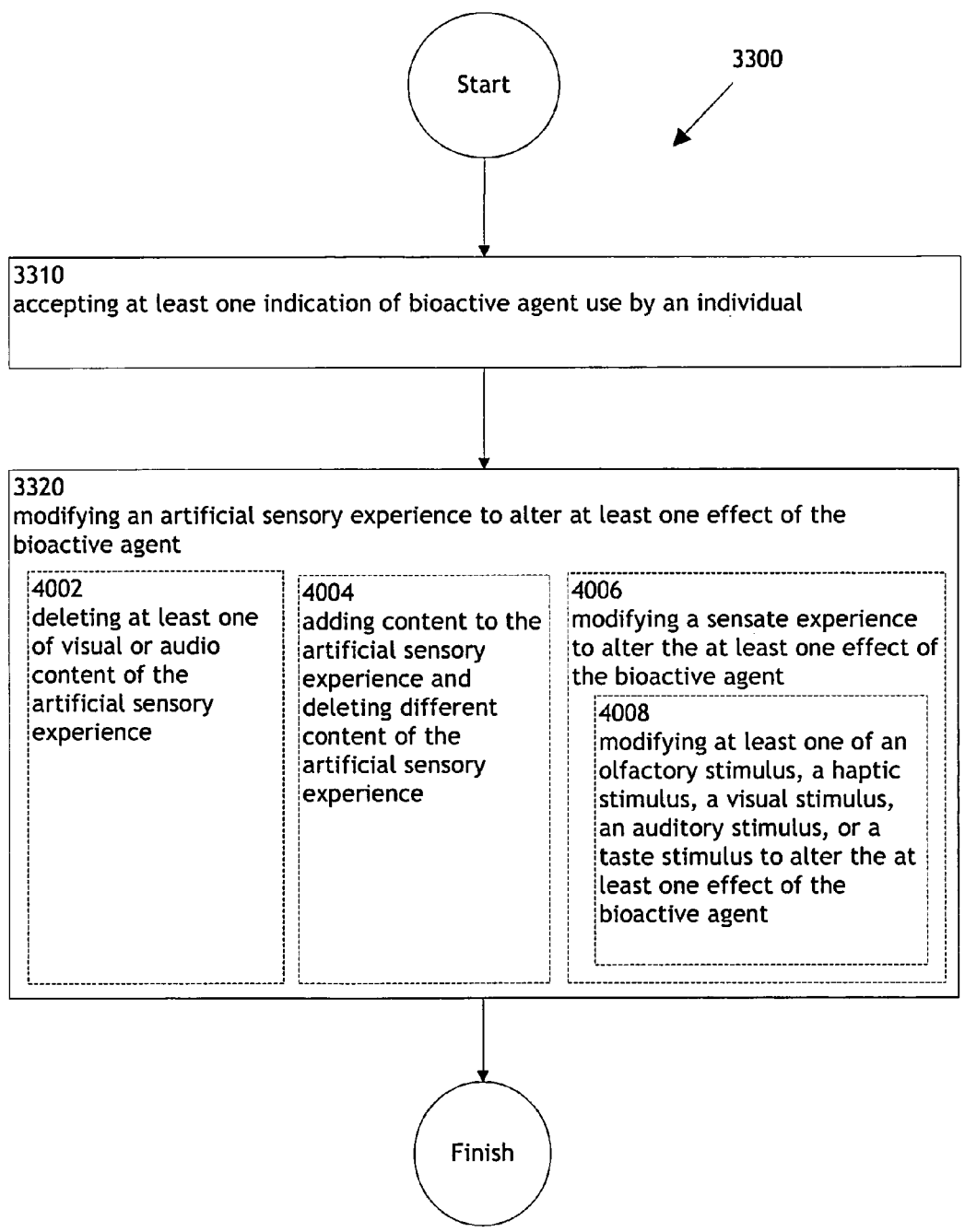
FIG. 40 illustrates an alternative embodiment of the operational flow of FIG. 33.

FIG. 40 illustrates alternative embodiments of the example operational flow 3300 of FIG. 33. FIG. 40 illustrates example embodiments where the operation 3320 may include at least one additional operation. Additional operations may include an operation 4002, an operation 4004, an operation 4006, and/or an operation 4008.

The operation 4002 illustrates deleting at least one of visual or audio content of the artificial sensory experience. For example, as shown in FIG. 1, deleter module 150 may delete at least one of visual or audio content of the artificial sensory experience. In one instance, deleter module 150 may delete visual content including a bright lighting environment in a virtual world for enhancing the effect of a medication for a migraine headache. Deleting may include reducing and/or eliminating visual and/or audio content. In some instances, deleter module 150 may include a computer processor.

The operation 4004 illustrates adding content to the artificial sensory experience and deleting different content of the artificial sensory experience. For example, as shown in FIG. 1, adder module 148 may add content to the artificial sensory experience and deleter module 150 may delete different content of the artificial sensory experience. In one instance, adder module 148 may add classical background music to a virtual world and delete ambient street noise, for example, using sound detection and/or noise-cancellation technology, to enhance the effect of a sedative or other similar bioactive agent. In some instances, adder module 148 and/or deleter module 150 may include a computer processor.

The operation 4006 illustrates modifying a sensate experience to alter the at least one effect of the bioactive agent. For example, as shown in FIG. 1, modifier module 140 may modify a sensate experience to alter the at least one effect of the bioactive agent. In one instance, modifier module 140 may modify a sensate experience including adding an aroma to enhance the effect of an anxiolytic drug or other similar bioactive agent. A sensate experience may include a thing perceived by the senses, such as an aroma, a sound, a feet, a taste, and/or a sight. In some instances, modifier module 140 may include a computer processor. Further, the operation 4008 illustrates modifying at least one of an olfactory stimulus, a haptic stimulus, a visual stimulus, an auditory stimulus, or a taste stimulus to alter the at least one effect of the bioactive agent. For example, as shown in FIG. 1, modifier module 140 may modify at least one of an olfactory stimulus, a haptic stimulus, a visual stimulus, an auditory stimulus, or a taste stimulus to alter the at least one effect of the bioactive agent. In one instance, modifier module 140 may modify an olfactory stimulus by adding a floral aroma and/or gentle vibration to enhance a relaxing effect of a sedative or other similar bioactive agent, such as an antianxiety medication. Further discussion of an olfactory stimulus may be found in Shaw, D. et al., *Anxiolytic effects of lavender oil inhalation on open-field behaviour in rats*, PHYTOMEDICINE, 14(9):613-20 (2007), incorporated by reference. In some instances, modifier module 140 may include a computer processor.

Figure 41:
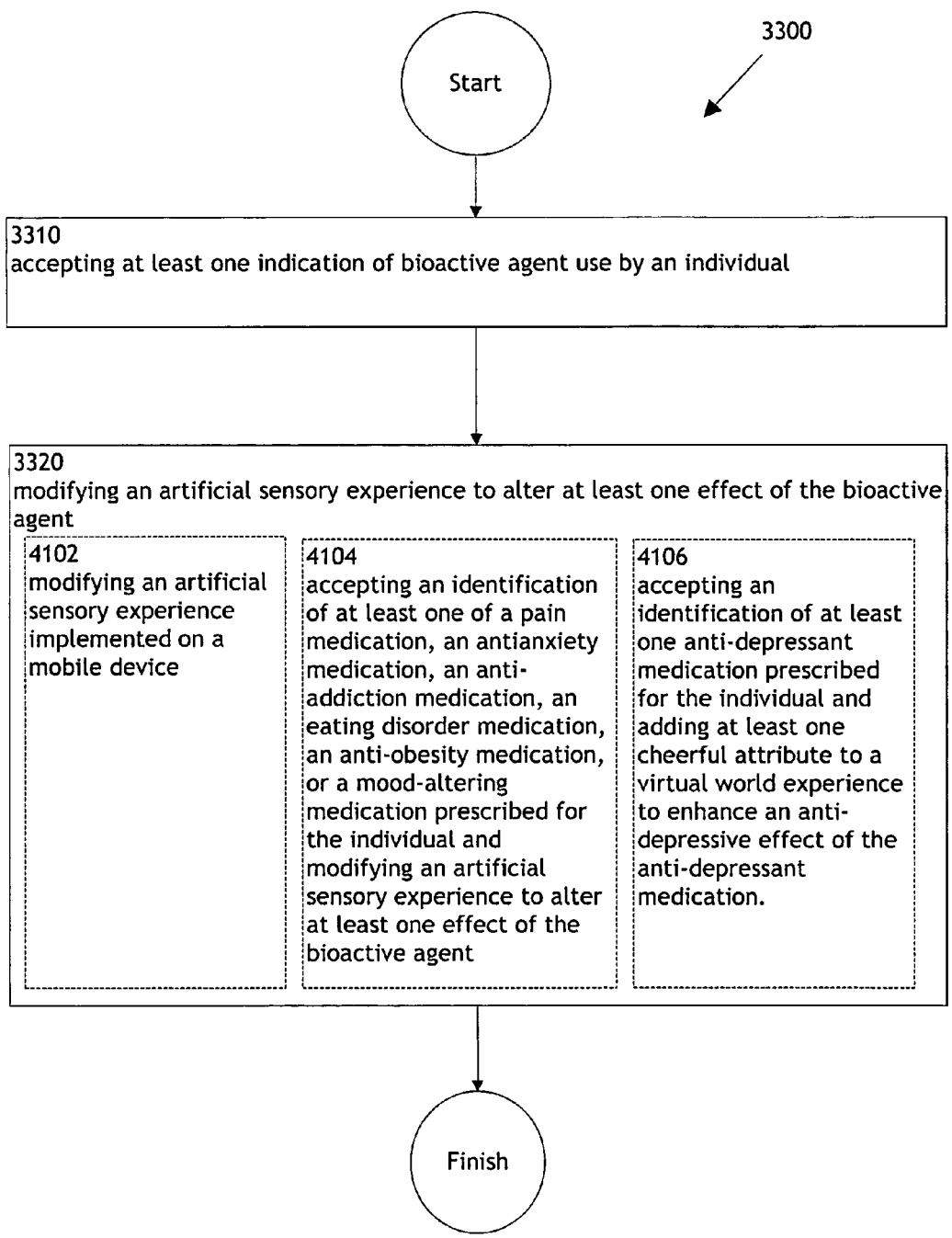
FIG. 41 illustrates an alternative embodiment of the operational flow of FIG. 33.

FIG. 41 illustrates alternative embodiments of the example operational flow 3300 of FIG. 33. FIG. 41 illustrates example embodiments where the operation 3320 may include at least one additional operation. Additional operations may include an operation 4102, 4104, and/or an operation 4106.

The operation 4102 illustrates modifying an artificial sensory experience implemented on a mobile device. For example, as shown in FIG. 1, modifier module 140 may modify an artificial sensory experience implemented on a mobile device. In one instance, modifier module 140 may modify a virtual world implemented in a web browser on a laptop computer having wireless capability and a battery by changing a background color theme to a brighter color theme in the virtual world. An artificial sensory experience modification, such as the color change in the above example, may enhance the effect of a bioactive agent. For example, modifying the color in the above example while an anti-depressant is bioavailable may create a more pleasant environment in the artificial sensory experience. Some examples of a mobile device may include a laptop or notebook computer, a personal digital assistant (PDA), an ipod, a smartphone, an Enterprise digital assistant (EDA), and/or a pager. In another example, modifier module 140 may modify a city image by providing a soothing image having fewer people in the same part of the city and combining the modified image with an anti-anxiety medicine for alleviating a phobia, such as agoraphobia. In another example, modifier module 140 may provide a stepwise procedure, with a gradually less specific procedure and/or less steps, for a compulsive patient to follow to achieve a goal for a particular outing while taking a selective serotonin reuptake inhibitor (SSRI). In some instances, modifier module 140 may include a computer processor.

The operation 4104 illustrates accepting an identification of at least one of a pain medication, an antianxiety medication, an anti-addiction medication, an eating disorder medication, an anti-obesity medication, or a mood-altering medication prescribed for the individual and modifying an artificial sensory experience to alter at least one effect of the bioactive agent. For example, as shown in FIG. 1, accepter module 152 may accept an identification of at least one of a pain medication, an antianxiety medication, an anti-addiction medication, an eating disorder medication, an anti-obesity medication, or a mood-altering medication prescribed for the individual and modifying an artificial sensory experience to alter at least one effect of the bioactive agent. In one instance, accepter module 152 may accept an identification of a pain medication. A pain medication, or an analgesic, may include a drug and/or other medication suitable for relieving pain. Additionally, an analgesic may be effective for relieving different degrees of pain. Some examples of an analgesic may include narcotics such as morphine or oxycodone, non-narcotics, an NSAID such as aspirin or naproxen or ibuprofen, and/or acetaminophen. An antianxiety drug may include a drug for suppressing anxiety and relaxing the muscles. An antianxiety drug may include a sedative, a tranquilizer, an anxiolytic, such as a benzodiazepine, alprazolam and/or diazepam, an antidepressant, a short-acting barbiturate, and/or an herbal treatment, such as chamomile, kava extract, Kratom, and/or valerian. An anti-addiction medication may include a substance used to replace another addictive substance, treat withdrawal, and/or decrease and/or eliminate craving. One example of an anti-addiction medication may include ibogaine. An eating disorder medication may include a pharmacological treatment used to eliminate or reduce an eating disorder, such as anorexia and/or bulimia. Some examples of an eating disorder medication may include a selective serotonin reuptake inhibitor (SSRI) and/or zinc. An anti-obesity medication may include a pharmacological treatment intended to reduce or control weight. Some examples of an anti-obesity medication may include ortistat, sibutramine, and/or pyruvate. A mood-altering medication may include a psychiatric medication used to treat mood disorders characterized by intense and sustained mood shifts. Some examples of a mood stabilizer may include lithium carbonate and/or lamotrigine. Additionally, modifying an artificial sensory experience may include a modification for enhancing positive aspects of behavior, such as improving information retention, reaction time, hearing acuity, attention span, and/or mental stamina. In some instances, accepter module 152 may include a computer processor.

The operation 4106 illustrates accepting an identification of at least one anti-depressant medication prescribed for the individual and adding at least one cheerful attribute to a virtual world experience to enhance an anti-depressive effect of the anti-depressant medication. For example, as shown in FIG. 1, accepter module 152 may accept an identification of at least one anti-depressant medication prescribed for the individual and adding at least one cheerful attribute to a virtual world experience to enhance an anti-depressive effect of the anti-depressant medication. For example, upon receipt of an indication that an individual is taking prozac, system 3300 and/or adder module 154 may place a filter over the graphics of the individual's facebook webpage that presents a bright color scheme that can enhance the anti-depressant effect of the prozac. In some instances, accepter module 152 and/or adder module 148 may include a computer processor.

Figure 42:
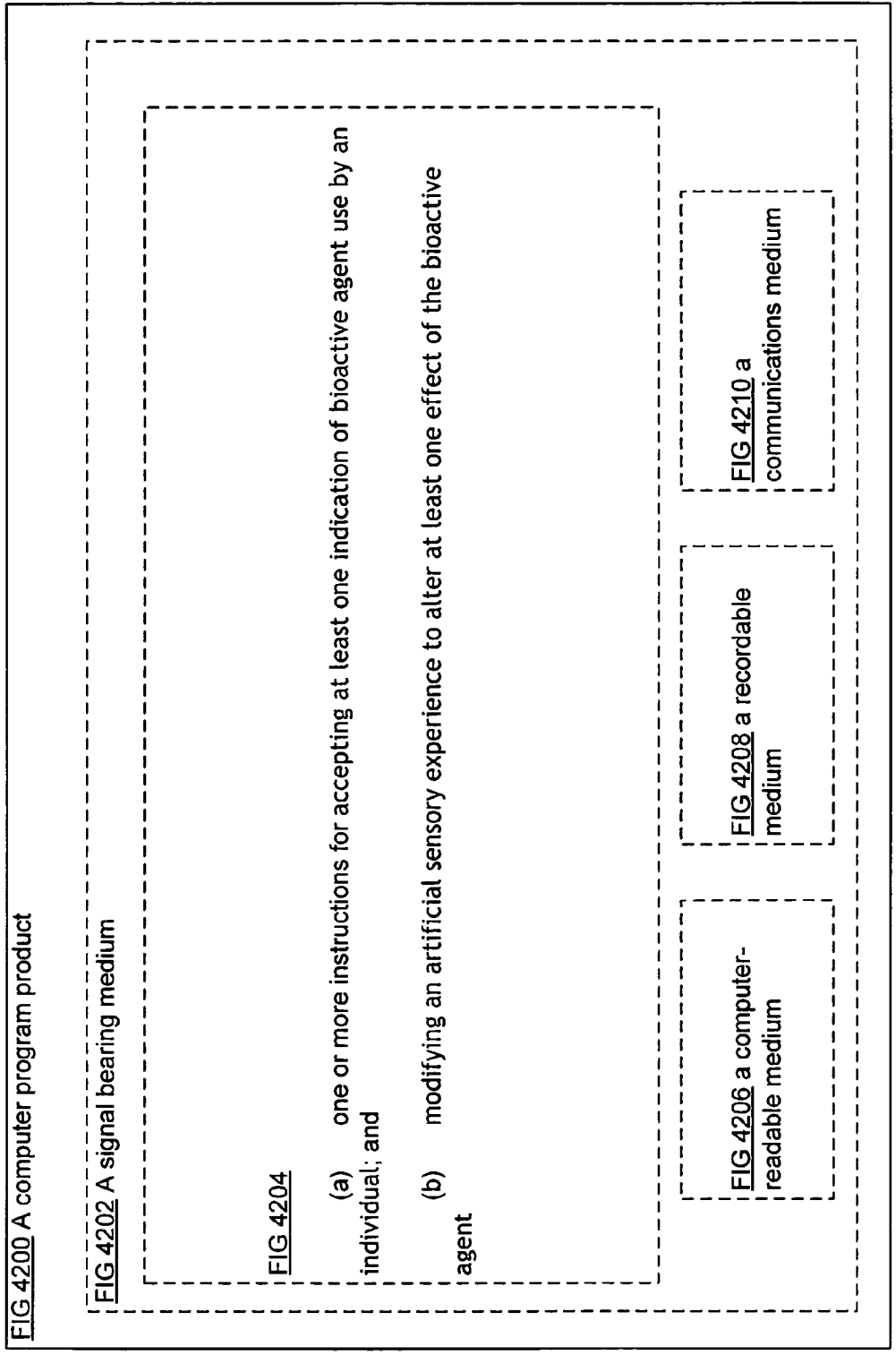
FIG. 42 illustrates a computer program product related to selecting a combination of at least one prescription medication and at least one artificial sensory experience.

FIG. 42 illustrates a partial view of an example computer program product 4200 that includes a computer program 4204 for executing a computer process on a computing device. An embodiment of the example computer program product 4200 is provided using a signal-bearing medium 4202, and may include one or more instructions for accepting at least one indication of bioactive agent use by an individual and one or more instructions for modifying an artificial sensory experience to alter at least one effect of the bioactive agent. The one or more instructions may be, for example, computer executable and/or logic-implemented instructions. In one implementation, the signal-bearing medium 4202 may include a computer-readable medium 4206. In one implementation, the signal bearing medium 4202 may include a recordable medium 4208. In one implementation, the signal bearing medium 4202 may include a communications medium 4210.

FIG. 43 illustrates an example system 4300 in which embodiments may be implemented. The system 4300 includes a computing system environment. The system 4300 also illustrates the user 118 using a device 4304, which is optionally shown as being in communication with a computing device 4302 by way of an optional coupling 4306. The optional coupling 4306 may represent a local, wide-area, or peer-to-peer network, or may represent a bus that is internal to a computing device (e.g., in example embodiments in which the computing device 4302 is contained in whole or in part within the device 4304). A storage medium 4308 may be any computer storage media.

The computing device 4302 includes computer-executable instructions 4310 that when executed on the computing device 4302 cause the computing device 4302 to accept at least one indication of bioactive agent use by an individual and modify an artificial sensory experience to alter at least one effect of the bioactive agent. As referenced above and as shown in FIG. 43, in some examples, the computing device 4302 may optionally be contained in whole or in part within the device 4304.

In FIG. 43, then, the system 4300 includes at least one computing device (e.g., 4302 and/or 4304). The computer-executable instructions 4310 may be executed on one or more of the at least one computing device. For example, the computing device 4302 may implement the computer-executable instructions 4310 and output a result to (and/or receive data from) the computing device 4304. Since the computing device 4302 may be wholly or partially contained within the computing device 4304, the device 4304 also may be said to execute some or all of the computer-executable instructions 4310, in order to be caused to perform or implement, for example, various ones of the techniques described herein, or other techniques.

The device 4304 may include, for example, a portable computing device, workstation, or desktop computing device. In another example embodiment, the computing device 4302 is operable to communicate with the device 4304 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art wilt recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art wilt also appreciate that examples of electromechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art wilt recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or togicalty interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it wilt be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent wilt be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
    accepting at least one attribute of at least one individual;
    querying at least one database based at least partially on the accepting at least one attribute;
    presenting at least one indication of at least one prescription medication and at least a first indication of at least one artificial sensory experience based at least partially on the querying at least one database; and
    presenting at least a second indication of the at least one artificial sensory experience based at least partially on at least one indication of use of the at least one prescription medication, including at least:

accepting the at least one indication of use of the at least one prescription medication by the at least one individual; and presenting the at least a second indication of the at least one artificial sensory experience based at least partially on the accepting at least one indication of use of the at least one prescription medication by the at least one individual, wherein at least one of the accepting at least one attribute, querying at least one database, presenting at least one indication of at least one prescription medication and at least a first indication of at least one artificial sensory experience, or presenting at least a second indication of the at least one artificial sensory experience is at least partially implemented using one or more processing devices.

2. The method of claim 1, wherein accepting the at least one indication of use of the at least one prescription medication by the at least one individual comprises:

accepting at least one indication of use of the at least one prescription medication based at least partially on at least one of one or more biochemical test results associated with the at least one individual or at least some user input associated with the at least one individual.

3. The method of claim 1, wherein accepting the at least one indication of use of the at least one prescription medication by the at least one individual and presenting at least a second indication of the at least one artificial sensory experience based at least partially on the accepting at least one indication of use of the at least one prescription medication by the at least one individual comprise:

determining whether the at least one individual has used the at least one prescription medication, and, if the at least one individual has used the at least one prescription medication, presenting at least a portion of the at least one artificial sensory experience via at least one user interface.

4. The method of claim 1, wherein presenting at least a second indication of the at least one artificial sensory experience based at least partially on at least one indication of use of the at least one prescription medication comprises:

modifying access to at least a portion of the at least one artificial sensory experience to alter at least one effect of the prescription medicine.

5. The method of claim 4, wherein modifying access to at least a portion of the at least one artificial sensory experience to alter at least one effect of the prescription medication comprises:

restricting access to at least a portion of the at least one artificial sensory experience.

6. The method of claim 4, wherein modifying access to at least a portion of the at least one artificial sensory experience to alter at least one effect of the prescription medication comprises:

granting access to at least a portion of the at least one artificial sensory experience.

7. The method of claim 1, wherein presenting at least a second indication of the at least one artificial sensory experience based at least partially on at least one indication of use of the at least one prescription medication comprises:

modifying the at least one artificial sensory experience to enhance at least one outcome associated with the efficacy of the prescription medication.

8. The method of claim 1, wherein presenting at least a second indication of the at least one artificial sensory experience based at least partially on at least one indication of use of the at least one prescription medication comprises:

modifying the at least one artificial sensory experience to alter at least one outcome associated with a side effect of the prescription medication.

9. The method of claim 1, wherein presenting at least a second indication of the at least one artificial sensory experience based at least partially on at least one indication of use of the at least one prescription medication comprises:

modifying a sensate experience to alter at least one presumed effect of the prescription medication.

10. The method of claim 9, wherein modifying a sensate experience to alter at least one presumed effect of the prescription medication comprises:

modifying at least one of an olfactory stimulus, a haptic stimulus, a visual stimulus, an auditory stimulus, or a taste stimulus to alter at least one presumed effect of the prescription medication.

11. The method of claim 1, wherein presenting at least a second indication of the at least one artificial sensory experience based at least partially on at least one indication of use of the at least one prescription medication comprises:

modifying at least one artificial sensory experience implemented on a mobile device.

12. The method of claim 1, wherein accepting at least one attribute of at least one individual comprises:

accepting at least one indication of post traumatic stress disorder associated with the at least one individual.

13. The method of claim 1, wherein accepting at least one attribute of at least one individual comprises:

accepting at least one indication of Alzheimer's disease associated with the at least one individual.

14. The method of claim 1, wherein accepting at least one attribute of at least one individual comprises:

accepting at least one indication of depression associated with the at least one individual.

15. The method of claim of 1, wherein accepting at least one attribute of at least one individual and querying at least one database based at least partially on the accepting at least one attribute comprise:

accepting at least one attribute of at least one individual, including at least accepting at least one mental enhancement goal associated with the at least one individual, the mental enhancement goal including at least one of reducing or eliminating a phobia; and querying at least one medication database and at least one artificial sensory experience database based at least partially on accepting at least one mental enhancement goal of reducing or eliminating a phobia, and selecting from at least one medication database at least one anti-anxiety medication for alleviating a phobia and selecting from at least one artificial sensory experience database at least one virtual world designed to overcome a phobia.

16. The method of claim 1, wherein accepting at least one attribute of at least one individual comprises:

accepting at least one indication of anxiety associated with the at least one individual.

17. The method of claim of 1, wherein accepting at least one attribute of at least one individual and querying at least one database based at least partially on the accepting at least one attribute comprise:

accepting at least one attribute of at least one individual, including at least accepting at least one mental enhancement goal associated with the at least one individual, the mental enhancement goal including at least one of reducing or eliminating a flying phobia; and querying at least one medication database and at least one artificial sensory experience database based at least partially on accepting at least one mental enhancement goal of reducing or eliminating a flying phobia, selecting from at least one medication database at least one anti-anxiety medication for alleviating a flying phobia, and selecting from at least one artificial sensory experience database at least one virtual world designed to overcome a flying phobia.

18. The method of claim 17, wherein querying at least one medication database and at least one artificial sensory experience database based at least partially on accepting at least one mental enhancement goal of reducing or eliminating a flying phobia, selecting from at least one medication database at least one anti-anxiety medication for alleviating a flying phobia, and selecting from at least one artificial sensory experience database at least one virtual world designed to overcome a flying phobia and presenting at least a second indication of the at least one artificial sensory experience based at least partially on at least one indication of use of the at least one prescription medication comprise:
 staggering a time associated with presentation of at least a portion of the at least one virtual world designed to overcome a flying phobia to provide conditioning for the at least one individual to reduce or eliminate the flying phobia, including at least:
  accepting at least one indication of use of the at least one anti-anxiety medication by the at least one individual;
  presenting at least a portion of the at least one virtual world designed to overcome a flying phobia based at least partially on the accepting at least one indication of use of the at least one anti-anxiety medication by the at least one individual;
  creating at least one history related to the at least one virtual world and the at least one individual, including at least storing one or more of at least one physiological measurement of the at least one individual or at least one indication of at least one level of anxiety accepted from the at least one individual via a user interface, the storing occurring at least one of during or subsequent to the presenting at least a portion of the at least one virtual world;
  modifying access to at least a portion of the at least one virtual world based at least partially on at least one history; and
  presenting at least a portion of the modified at least one virtual world.

19. The method of claim 1, wherein querying at least one database based at least partially on the accepting at least one attribute comprises:
 querying at least one medication database and at least one artificial sensory experience database based at least partially on the at least one attribute.

20. The method of claim 1, wherein querying at least one database based at least partially on the accepting at least one attribute comprises:
 querying at least one database based at least partially on the at least one attribute of the at least one individual; and
 selecting from the at least one database the at least one prescription medication and the at least one artificial sensory experience to at least partially address the at least one attribute of the at least one individual.

21. The method of claim 1, wherein presenting at least a second indication of the at least one artificial sensory experience based at least partially on at least one indication of use of the at least one prescription medication comprises:
 creating at least one history related to the at least one artificial sensory experience and the at least one individual.

22. The method of claim 21, further comprising:
 modifying access to at least a portion of the at least one artificial sensory experience based at least partially on the at least one history related to the at least one artificial sensory experience and the at least one individual.

23. The method of claim 22, further comprising:
 presenting at least one indication of the at least one modified artificial sensory experience at least partially based on the at least one history.

24. The method of claim 21, further comprising:
 presenting at least one indication of at least one modified artificial sensory experience at least partially based on the at least one history related to the at least one artificial sensory experience and the at least one individual.

25. The method of claim 1, wherein presenting at least a second indication of the at least one artificial sensory experience based at least partially on at least one indication of use of the at least one prescription medication comprises:
 creating at least one history related to the at least one artificial sensory experience and the at least one individual, the at least one history including one or more of at least one physiological measurement of the at least one individual or at least one indication of at least one level of anxiety accepted from the at least one individual via at least one user interface.

26. The method of claim 1, wherein presenting at least a second indication of the at least one artificial sensory experience based at least partially on at least one indication of use of the at least one prescription medication comprises:
 staggering a time associated with presentation of at least a portion of the at least one artificial sensory experience.

27. The method of claim 1, wherein presenting at least a second indication of the at least one artificial sensory experience based at least partially on at least one indication of use of the at least one prescription medication including at least accepting the at least one indication of use of the at least one prescription medication by the at least one individual and presenting the at least a second indication of the at least one artificial sensory experience based at least partially on the accepting at least one indication of use of the at least one prescription medication by the at least one individual comprise:
 staggering a time associated with presentation of at least a portion of the at least one artificial sensory experience, including at least:
  accepting at least one indication of use of the at least one prescription medication by the at least one individual;
  presenting at least a portion of the at least one artificial sensory experience via at least one user interface based at least partially on the accepting at least one indication of use of the at least one prescription medication by the at least one individual; and
  presenting at least a portion of a modified at least one artificial sensory experience, the modification based at least in part on one or more of at least one physiological measurement of the at least one individual or at least one indication of at least one level of anxiety accepted from the at least one individual, the one or more of at least one physiological measurement or at least one level of anxiety obtained at least one of during or subsequent to the presenting at least a portion of the at least one artificial sensory experience.

28. The method of claim 1, wherein presenting at least a second indication of the at least one artificial sensory experience based at least partially on at least one indication of use of the at least one prescription medication further comprises:

modifying the at least one artificial sensory experience based at least partially on one or more of at least one physiological measurement of the at least one individual or at least one indication of at least one level of anxiety accepted from the at least one individual via at least one user interface, the one or more of at least one physiological measurement or at least one level of anxiety obtained at least one of during or subsequent to the presenting of the at least one artificial sensory experience.

29. A system, comprising:
an acceptor module configured to accept at least one attribute of at least one individual;
a querier module configured to query at least one database based at least partially on the acceptor module configured to accept at least one attribute of at least one individual;
a first presenter module configured to present at least one indication of at least one prescription medication and at least a first indication of at least one artificial sensory experience based at least partially on the querier module configured to query at least one database; and
an implementer module configured to present at least a second indication of the at least one artificial sensory experience based at least partially on at least one indication of use of at least one prescription medication, including at least:
  a prescription acceptor module configured to accept at least one indication of use of at least one prescription medication by at least one individual; and
  a second presenter module configured to present at least another indication of at least one artificial sensory experience based at least partially on the prescription acceptor module configured to accept at least one indication of use of at least one prescription medication by at least one individual,
wherein at least one of the acceptor module, querier module, first presenter module, or implementer module is at least partially implemented using hardware.

30. A system, comprising:
circuitry configured for accepting at least one attribute of at least one individual;
circuitry configured for querying at least one database based at least partially on the circuitry configured for accepting at least one attribute;
circuitry configured for presenting at least one indication of at least one prescription medication and at least a first indication of at least one artificial sensory experience based at least partially on the circuitry configured for querying at least one database; and
circuitry configured for presenting at least a second indication of the at least one artificial sensory experience based at least partially on at least one indication of use of the at least one prescription medication, including at least:
  circuitry configured for accepting the at least one indication of use of the at least one prescription medication by the at least one individual; and
  circuitry configured for presenting the at least a second indication of the at least one artificial sensory experience based at least partially on the circuitry configured for accepting the at least one indication of use of the at least one prescription medication by the at least one individual.

31. A computer program product, comprising:
at least one non-transitory computer readable medium including at least one or more instructions that, when executed on at least one processing device, cause the at least one processing device to at least:
  accept at least one attribute of at least one individual;
  query at least one database based at least partially on the accepted at least one attribute;
  present at least one indication of at least one prescription medication and at least a first indication of at least one artificial sensory experience based at least partially on the at least one database query; and
  present at least a second indication of the at least one artificial sensory experience based at least partially on at least one indication of use of the at least one prescription medication, including at least:
    accepting the at least one indication of use of the at least one prescription medication by the at least one individual; and
    presenting the at least a second indication of the at least one artificial sensory experience based at least partially on the accepted at least one indication of use of the at least one prescription medication by the at least one individual.

32. A system, comprising:
a computing device; and
one or more instructions that when executed on the computing device cause the computing device to:
  accept at least one attribute of at least one individual;
  query at least one database based at least partially on the accepted at least one attribute;
  present at least one indication of at least one prescription medication and at least a first indication of at least one artificial sensory experience based at least partially on the at least one database query; and
  present at least a second indication of the at least one artificial sensory experience based at least partially on at least one indication of use of the at least one prescription medication, including at least:
    accepting the at least one indication of use of the at least one prescription medication by the at least one individual; and
    presenting the at least a second indication of the at least one artificial sensory experience based at least partially on the accepted at least one indication of use of the at least one prescription medication by the at least one individual.

33. The system of claim 32 wherein the computing device comprises:
one or more of a personal digital assistant (PDA), a personal entertainment device, a mobile phone, a laptop computer, a tablet personal computer, a networked computer, a computing system comprised of a cluster of processors, a computing system comprised of a cluster of servers, a workstation computer, or a desktop computer.

34. The system of claim 32, wherein the computing device is operable to accept at least the at least one attribute, query the at least one database, and present the at least one indication of at least one prescription medication and at least a first indication of at least one artificial sensory experience, and present the at least a second indication of the at least one artificial sensory experience from at least one memory.

* * * * *